US011707514B2

(12) United States Patent
Kensinger, Jr. et al.

(10) Patent No.: US 11,707,514 B2
(45) Date of Patent: Jul. 25, 2023

(54) NEISSERIA MENINGITIDIS VACCINE

(71) Applicant: Sanofi Pasteur Inc., Swiftwater, PA (US)

(72) Inventors: Richard David Kensinger, Jr., Henryville, PA (US); Steven L. Hauser, Easton, PA (US)

(73) Assignee: Sanofi Pasteur Inc., Swiftwater, PA (US)

( * ) Notice: Subject to any disclaimer, the term of this patent is extended or adjusted under 35 U.S.C. 154(b) by 120 days.

(21) Appl. No.: 17/468,989

(22) Filed: Sep. 8, 2021

(65) Prior Publication Data

US 2021/0401964 A1 Dec. 30, 2021

Related U.S. Application Data

(60) Division of application No. 16/282,080, filed on Feb. 21, 2019, now Pat. No. 11,147,866, which is a continuation of application No. PCT/US2017/049856, filed on Sep. 1, 2017.

(60) Provisional application No. 62/505,525, filed on May 12, 2017, provisional application No. 62/468,695, filed on Mar. 8, 2017, provisional application No. 62/383,279, filed on Sep. 2, 2016.

(51) Int. Cl.
| | |
|---|---|
| *A61K 39/095* | (2006.01) |
| *A61K 47/65* | (2017.01) |
| *A61K 47/64* | (2017.01) |
| *A61K 47/18* | (2017.01) |
| *A61K 47/36* | (2006.01) |
| *A61K 39/00* | (2006.01) |

(52) U.S. Cl.
CPC ............ *A61K 39/095* (2013.01); *A61K 47/18* (2013.01); *A61K 47/36* (2013.01); *A61K 47/6415* (2017.08); *A61K 47/65* (2017.08); *A61K 2039/55583* (2013.01); *A61K 2039/6037* (2013.01); *A61K 2039/70* (2013.01); *Y02A 50/30* (2018.01)

(58) Field of Classification Search
CPC .. A61K 39/095; A61K 47/65; A61K 47/6415; A61K 47/36; A61K 2039/55583; A61K 2039/6037; A61K 2039/70
See application file for complete search history.

(56) References Cited

U.S. PATENT DOCUMENTS

| | | | |
|---|---|---|---|
| 4,673,574 A | 6/1987 | Anderson | |
| 4,695,624 A | 9/1987 | Marburg et al. | |
| 4,882,317 A | 11/1989 | Marburg et al. | |
| 5,097,020 A | 3/1992 | Anderson et al. | |
| 5,371,197 A | 12/1994 | Marburg et al. | |
| 5,425,946 A | 6/1995 | Tai et al. | |
| 6,146,902 A | 11/2000 | McMaster | |
| 6,309,633 B1 | 10/2001 | Ekwuribe et al. | |
| 6,309,646 B1 | 10/2001 | Lees | |
| 6,645,503 B1 | 11/2003 | Arumugham et al. | |
| 6,656,472 B1 | 12/2003 | Chong et al. | |
| 6,673,905 B2 | 1/2004 | Pozsgay | |
| 6,933,137 B2 | 8/2005 | Egen et al. | |
| 7,018,637 B2 | 3/2006 | Chong et al. | |
| 7,491,517 B2 | 2/2009 | Reddy | |
| 7,588,765 B2 | 9/2009 | Porro | |
| 7,927,858 B2 | 4/2011 | Mayeresse | |
| 7,935,787 B2 | 5/2011 | Khandke et al. | |
| 7,972,608 B2 | 7/2011 | Kim et al. | |
| 8,007,807 B2 | 8/2011 | Borkowski | |
| 8,048,432 B2 | 11/2011 | Lee et al. | |
| 8,062,641 B2 | 11/2011 | Oscarson et al. | |
| 8,129,147 B2 | 3/2012 | Reddy | |
| 8,163,296 B2 | 4/2012 | Capannoli et al. | |
| 8,329,184 B2 | 12/2012 | Biemans et al. | |
| 8,361,477 B2 | 1/2013 | Borkowski | |
| 8,398,983 B2 | 3/2013 | Biemans et al. | |
| 8,398,985 B2 | 3/2013 | Kapre et al. | |
| 8,431,136 B2 | 4/2013 | Biemans et al. | |
| 8,444,992 B2 | 5/2013 | Borkowski | |
| 8,449,865 B2 | 5/2013 | Mayeresse | |
| 8,465,749 B2 | 6/2013 | Lee et al. | |
| 8,492,364 B2 | 7/2013 | Pier et al. | |
| 8,529,908 B2 | 9/2013 | Marshall | |
| 8,551,527 B2 | 10/2013 | Chouvenc et al. | |
| 8,562,999 B2 | 10/2013 | Khandke et al. | |
| 8,598,337 B2 | 12/2013 | Michon et al. | |
| 8,642,042 B2 | 2/2014 | Mekalanos | |
| 8,722,062 B2 | 5/2014 | Ryall | |
| 8,753,645 B2 | 6/2014 | Biemans et al. | |
| 8,753,649 B2 | 6/2014 | Lee et al. | |
| 8,753,651 B2 | 6/2014 | Costantino | |
| 8,765,135 B2 | 7/2014 | Contorni | |

(Continued)

FOREIGN PATENT DOCUMENTS

| | | | |
|---|---|---|---|
| CN | 1703241 A | 11/2005 | |
| CN | 1890261 A | 1/2007 | |

(Continued)

OTHER PUBLICATIONS

Broker et al. 2016 (Factors contributing to the immunogenicity of meningococcal conjugate vaccines; Human Vaccines and Immunotherapeutics 12(7) :1808-1824). (Year: 2016).*
Pichichero, Michael E., "Protein carriers of conjugate vaccines", Hum Vaccin Immunother, 9(12), pp. 2505-2523 (Dec. 1, 2013).
Yang et al., "New Advances in meningococcal vaccine research", China Tropical Medicine, 10, pp. 2064-2066 (2009) (with English translation provided).
Anderson, G.W., "N,N'-Carbonyldiimidazole, a new reagent for peptide synthesis", J. Am. Chem. Soc., 80, 4323 (1958).
Assaf-Casals et al., "Meningococcal quadrivalent tetanus toxoid conjugate vaccine (MenACWY-TT, Nimenrix™): A review of its immunogenicity, safety, co-administration, and antibody persistence", Human Vaccines and Immunotherapeutics, p. 1-13; 2016.

(Continued)

*Primary Examiner* — Mary Maille Lyons
(74) *Attorney, Agent, or Firm* — McNeill Baur, PLLC

(57) ABSTRACT

Provided herein are compounds, compositions, formulations, kits, uses, and methods for vaccinating a subject against *Neisseria meningitidis*.

25 Claims, 26 Drawing Sheets

(56) References Cited

U.S. PATENT DOCUMENTS

| | | |
|---|---|---|
| 8,784,826 B2 | 7/2014 | Borkowski |
| 8,846,049 B2 | 9/2014 | Biemans et al. |
| 8,852,606 B2 | 10/2014 | Costantino |
| 8,883,163 B2 | 11/2014 | Biemans et al. |
| 8,883,166 B2 | 11/2014 | Contorni et al. |
| 8,889,152 B2 | 11/2014 | Costantino |
| 8,986,710 B2 | 3/2015 | Anderson et al. |
| 8,999,354 B2 | 4/2015 | Ryall |
| 9,040,058 B2 | 5/2015 | Blackkolb et al. |
| 9,102,699 B2 | 8/2015 | Jain et al. |
| 9,120,848 B2 | 9/2015 | Kaplan |
| 9,173,931 B2 | 11/2015 | Jessouroun et al. |
| 9,173,954 B2 | 11/2015 | Costantino et al. |
| 9,173,955 B2 | 11/2015 | Ryall |
| 9,175,033 B2 | 11/2015 | Lee |
| 9,180,204 B2 | 11/2015 | Contorni |
| 9,198,976 B2 | 12/2015 | Lee et al. |
| 9,198,977 B2 | 12/2015 | Kapre et al. |
| 9,216,223 B2 | 12/2015 | Mekalanos |
| 9,283,270 B2 | 3/2016 | Kapre et al. |
| 9,333,247 B2 | 5/2016 | Moe et al. |
| 9,358,278 B2 | 6/2016 | Costantino |
| 9,358,279 B2 | 6/2016 | Biemans et al. |
| 9,358,302 B2 | 6/2016 | Avci et al. |
| 9,402,915 B2 | 8/2016 | Marshall |
| 9,427,476 B2 | 8/2016 | Lee et al. |
| 9,452,207 B2 | 9/2016 | Costantino |
| 9,452,224 B2 | 9/2016 | Jain et al. |
| 9,463,250 B2 | 10/2016 | Bigio et al. |
| 9,474,795 B2 | 10/2016 | Lee et al. |
| 9,486,515 B2 | 11/2016 | Biemans et al. |
| 9,492,558 B2 | 11/2016 | Costantino |
| 9,493,517 B2 | 11/2016 | Costantino et al. |
| 9,511,132 B2 | 12/2016 | Contorni |
| 9,517,274 B2 | 12/2016 | Gu et al. |
| 9,533,032 B2 | 1/2017 | Mekalanos |
| 9,580,734 B2 | 2/2017 | Shankar et al. |
| 9,636,393 B2 | 5/2017 | Giuliani et al. |
| 9,724,401 B2 | 8/2017 | Killeen et al. |
| 9,782,466 B2 | 10/2017 | Constantino |
| 9,782,467 B2 | 10/2017 | Costantino |
| 9,782,468 B2 | 10/2017 | Damotharan et al. |
| 9,789,179 B2 | 10/2017 | Biemans et al. |
| 9,803,030 B2 | 10/2017 | Bardotti et al. |
| 9,827,301 B2 | 11/2017 | Costantino et al. |
| 9,844,601 B2 | 12/2017 | Ryall |
| 9,931,397 B2 | 4/2018 | Biemans et al. |
| 10,011,662 B2 | 7/2018 | Gill et al. |
| 10,064,932 B2 | 9/2018 | Marshall |
| 2005/0002957 A1 | 1/2005 | Ryall |
| 2007/0020293 A1 | 1/2007 | Michon |
| 2007/0116714 A1 | 5/2007 | Slaoui et al. |
| 2008/0193476 A1 | 8/2008 | Biemans et al. |
| 2009/0041802 A1 | 2/2009 | Biemans et al. |
| 2009/0136541 A1 | 5/2009 | Biemans et al. |
| 2009/0252759 A1 | 10/2009 | Biemans et al. |
| 2010/0203137 A1 | 8/2010 | Contorni et al. |
| 2010/0285069 A1 | 11/2010 | Contorni et al. |
| 2012/0207780 A1 | 8/2012 | Boutriau et al. |
| 2013/0209503 A1 | 8/2013 | Kapre et al. |
| 2014/0234368 A1 | 8/2014 | Costantino et al. |
| 2015/0004191 A1 | 1/2015 | Contorni |
| 2015/0044253 A1 | 2/2015 | Biemans et al. |
| 2015/0093411 A1 | 4/2015 | Michon et al. |
| 2015/0104479 A1 | 4/2015 | Romano et al. |
| 2015/0165016 A1 | 6/2015 | Pier et al. |
| 2016/0101187 A1 | 4/2016 | Berti et al. |
| 2016/0175421 A1 | 6/2016 | Wong et al. |
| 2016/0228529 A1 | 8/2016 | Contorni et al. |
| 2016/0237116 A1 | 8/2016 | Usera et al. |
| 2016/0297895 A1 | 10/2016 | Saul et al. |
| 2017/0000874 A1 | 1/2017 | Jianhua |
| 2017/0037440 A1 | 2/2017 | Fiebig et al. |
| 2017/0066794 A1 | 3/2017 | Gill et al. |
| 2017/0080080 A1 | 3/2017 | Trent et al. |
| 2019/0175718 A1 | 6/2019 | Kensinger, Jr. et al. |

FOREIGN PATENT DOCUMENTS

| | | |
|---|---|---|
| CN | 100338218 C | 9/2007 |
| CN | 101048177 A | 10/2007 |
| CN | 101208102 A | 6/2008 |
| CN | 101448518 A | 6/2009 |
| CN | 101448522 A | 6/2009 |
| CN | 102596240 B | 7/2012 |
| CN | 101863998 B | 8/2012 |
| CN | 102809656 B | 12/2012 |
| CN | 102917730 A | 2/2013 |
| CN | 101374548 B | 5/2013 |
| CN | 101708333 B | 3/2014 |
| CN | 102755631 B | 11/2015 |
| CN | 104225587 B | 7/2017 |
| EP | 0562107 B1 | 9/1993 |
| EP | 0941738 B1 | 9/1999 |
| EP | 1109576 B1 | 6/2001 |
| EP | 1163008 B1 | 8/2003 |
| EP | 1124576 B1 | 12/2004 |
| EP | 1587537 B1 | 10/2005 |
| EP | 1651261 B1 | 5/2006 |
| EP | 1678212 B1 | 7/2006 |
| EP | 1140156 B1 | 12/2006 |
| EP | 1762245 B1 | 3/2007 |
| EP | 1778291 B1 | 5/2007 |
| EP | 1501542 B2 | 8/2007 |
| EP | 1896065 B1 | 3/2008 |
| EP | 1638601 B1 | 11/2008 |
| EP | 2004225 B1 | 12/2008 |
| EP | 2032160 B2 | 3/2009 |
| EP | 2056871 B1 | 5/2009 |
| EP | 1755662 B1 | 8/2009 |
| EP | 1409013 B1 | 11/2009 |
| EP | 1835939 B1 | 4/2010 |
| EP | 1741442 B1 | 7/2010 |
| EP | 2208999 B1 | 7/2010 |
| EP | 2229954 B1 | 9/2010 |
| EP | 2277536 B1 | 2/2011 |
| EP | 2170391 B1 | 7/2011 |
| EP | 2374473 B1 | 10/2011 |
| EP | 2376112 B1 | 10/2011 |
| EP | 2366404 B1 | 3/2012 |
| EP | 2263688 B1 | 5/2012 |
| EP | 1265633 B1 | 12/2012 |
| EP | 2172213 B1 | 4/2013 |
| EP | 2683408 B1 | 1/2014 |
| EP | 2180901 B1 | 12/2014 |
| EP | 2815762 B1 | 12/2014 |
| EP | 1885734 B1 | 1/2015 |
| EP | 1993604 B1 | 12/2015 |
| EP | 2950815 B1 | 12/2015 |
| EP | 2976101 A1 | 1/2016 |
| EP | 2184071 B1 | 8/2016 |
| EP | 1777236 B1 | 11/2016 |
| EP | 2351578 B1 | 1/2017 |
| EP | 2118145 B1 | 5/2017 |
| EP | 3006041 B1 | 11/2017 |
| EP | 2216044 B1 | 3/2018 |
| EP | 2878307 B1 | 7/2019 |
| JP | 2015134829 A | 7/2015 |
| WO | 9629094 A1 | 9/1996 |
| WO | 1999018121 A1 | 4/1999 |
| WO | 2000038711 A2 | 7/2000 |
| WO | 2002058737 A1 | 8/2002 |
| WO | 2002058737 A2 | 8/2002 |
| WO | 2004033623 A2 | 4/2004 |
| WO | 2004103400 A2 | 12/2004 |
| WO | 2006034320 A2 | 3/2006 |
| WO | 2007000314 A2 | 1/2007 |
| WO | 2007000322 A1 | 1/2007 |
| WO | 2007000327 A1 | 1/2007 |
| WO | 2007000341 A2 | 1/2007 |
| WO | 2007000343 A2 | 5/2007 |
| WO | 2007102797 A2 | 9/2007 |

(56) References Cited

FOREIGN PATENT DOCUMENTS

| WO | 2007000342 A2 | 7/2008 |
|---|---|---|
| WO | 2008081014 A2 | 7/2008 |
| WO | 2009150543 A2 | 12/2009 |
| WO | 2011110531 A2 | 9/2011 |
| WO | 2012119972 A1 | 9/2012 |
| WO | 2013114268 A1 | 8/2013 |
| WO | 2014009971 A2 | 1/2014 |
| WO | 2014097099 A2 | 6/2014 |
| WO | 2014147044 A1 | 9/2014 |
| WO | 2014188313 A1 | 11/2014 |
| WO | 2015052684 A1 | 4/2015 |
| WO | 2015084846 A1 | 6/2015 |
| WO | 2015052684 A2 | 7/2015 |
| WO | 2015121783 A1 | 8/2015 |
| WO | 2015181834 A2 | 1/2016 |
| WO | 2016055957 A1 | 4/2016 |
| WO | 2016132294 A1 | 8/2016 |
| WO | 2015175355 A1 | 11/2016 |
| WO | 2016174683 A1 | 11/2016 |
| WO | 2017006349 A1 | 1/2017 |
| WO | 2017036138 A1 | 3/2017 |
| WO | 2017085602 A1 | 5/2017 |
| WO | 2017158480 A1 | 9/2017 |
| WO | 2018045286 A1 | 3/2018 |
| WO | 2018156467 A1 | 8/2018 |

OTHER PUBLICATIONS

Baltzly et al, "The Aminolysis of Esters. A Preliminary Study", J. Am. Chem. Soc. 1950, v72, pp. 4149-4152.
Bartling et al., "Synthesis of a matrix-supported enzyme in non-aqueous conditions", Nature (London) 243, pp. 342-344 (1973).
Baxter et al., "Five-year Antibody Persistence and Booster Response to a Single Dose of Meningococcal A, C, W and Y Tetanus Toxoid Conjugate Vaccine in Adolescents and Young Adults", The Pediatric Infectious Disease Journal, 34(11), pp. 1236-1243 (Nov. 2015).
Baxter et al., "Immunogenicity and Safety of an Investigational Quadrivalent Meningococcal ACQY Tetanus Toxoid Conjugate Vaccine in Healthy Adolescents and Young Adults 10 to 25 years of Age", The Pediatric Infectious Disease Journal, 30(3), pp. e41-e48 (Mar. 2011).
Beresford et al., "Quality, immunogenicity and stability of meningococcal serogroup ACWY-CRM197, DT and TT glycoconjugate vaccines", Vaccine (2017), http://dx.doi.org/10.1016/j.vaccine.2017.03.066.
Bermal et al., "Safety and immunogenicity of a tetravalent meningococcal serogroups A, C, W-135 and Y conjugate vaccine in adolescents and adults", Human Vaccines, 7:2, pp. 239-247 (2011).
Berti et al., "Role of O-Acetylation in the Immunogenicity of Bacterial Polysaccharide Vaccines", Molecules, 2018, 23, 1340.
Bessi et al., "Science vs Conspiracy: Collective Narratives in the Age of Misinformation", Plos One, 10(2):e0118093 (Feb. 23, 2015).
Bethell, et al. "A novel method of activation of cross-linked agaroses with 1,1'-carbonyldiimidazole which gives a matrix for affinity chromatography devoid of additional charged groups", J. Biol. Chem., 254, pp. 2572-2574 (1979).
Borja-Tabora et al., "Long-term immunogenicity and safety after a single dose of the quadrivalent meningococcal serogroups A, C, W, and Y tetanus toxoid conjugate vaccine in adolescents and adults: 5-year follow-up of an open, randomized trial", BMC Infectious Diseases 15:409 (2015) (10 pages).
Borjo-Tabora et al., "Immune response, antibody persistence, and safety of a single dose of the quadrivalent meningococcal serogroups A, C, W-135, and Y tetanus toxoid conjugate vaccine in adolescents and adults: results of an open, randomised,controlled study", BMC Infectious Diseases, 13:116 (2013) (13 pages).
Broker et al., "Factors contributing to the immunogenicity of meningococcal conjugate vaccines", Human Vaccines & Immunotherapeutics, 12(7), pp. 1808-1824 (2016).

Cornish et al., "Safety and immunogenicity of an investigational quadrivalent meningococcal conjugate vaccine (MenACYW-TT) administered to infants and toddlers", 20th International Pathogenic Neisseria Conference, Manchester, United Kingdom, Abstract ID: 162 (Sep. 4-9, 2016) (1 page).
Cornish et al., "Safety and immunogenicity of an investigational quadrivalent meningococcal conjugate vaccine (MenACYW-TT) administered to infants and toddlers", 20th International Pathogenic Neisseria Conference, Manchester, United Kingdom, Poster # 162 (Sep. 4-9, 2016) (1 page).
Dbaibo et al. "Immunogenicity and Safety of a Quadrivalent Meningococcal Serogroups A, C, W-135 and Y Tetanus Toxoid Conjugate Vaccine (MenACQY-TT) Administered to Adults Aged 56 Years and Older: Results of an Open-Label, Randomized, Controlled Trial", Drugs Aging, 30, pp. 309-319 (2013).
Dbaibo et al., "The immunogenicity and safety of an investigational meningococcal serogroups A,C, W-135 and Y tetanus toxoid conjugate vaccine (ACWY-TT) compared with a licensed meningococcal tetravalent polysaccharide vaccine A randomized, controlled non-inferiority study", Human Vaccines & Immunotherapeutics 8:7, pp. 873-880 (Jul. 2012).
Dhillon et al: "Meningococcal Quadrivalent Tetanus Toxoid Conjugate Vaccine (MenACCWY-TT; Nimenrix): A review"; Drugs; vol. 77, No. 17, 2017, pp. 1881-1896.
Findlow et al., "The Global Meningococcal Initiative: Current Strategies for the Prevention of Meningococcal Disease and the Importance of Herd Protection", Global Meningococcal Initiative, International Pathogenic Neisseria Conference, Manchester, UK, Sep. 2016 (1 page).
Frasch, "Preparation of bacterial polysaccharide-protein conjugates: Analytical and manufacturing challenges", Vaccine, vol. 27, Issue 46, Oct. 30, 2009, pp. 6468-6470.
Ghanem et al., "Quadrivalent meningococcal serogroups A,C, W, and Y tetanus toxoid conjugate vaccine (MenACWY-TT): a review", Expert Opinion on Biological Therapy, 13(8), pp. 1197-1205 (Jul. 2, 2013).
Halperin et al., "Comparison of the Safety and Immunogenicity of a Novel Quadrivalent Meningococcal ACWY-Tetanus Toxoid Conjugate Vaccine and a Marketed Quadrivalent Meningococcal ACWY-Diphtheria Toxoid Conjugate Vaccine in Healthy Individuals 10-25 Years of Age", Journal of the Pediatric Infectious Diseases Society, 3(1), pp. 33-42 (2014).
Hearn et al., "Application of 1,1'-carbonyldiimidazole-activated agarose for the purification of proteins", J. Chromatogr, 185, pp. 463-470 (1979).
Hearn et al., "Preparative and analytical applications of CDI-mediated affinity chromatography", Affinity Chromatography and Biological Recognition, pp. 191-196. Academic Press, New York (1983).
Hedari et al., "Meningococcal serogroups A, C, W-135, and Y tetanus toxoid conjugate vaccine: a new conjugate vaccine against invasive meningococcal disease", Infection and Drug Resistance, 7, pp. 85-99 (2014).
Hermanson et al., "3. N,N'-Carbonyldiimidazole", Bioconjugate Techniques, pp. 183-185 (1996).
Hermanson, G.T., "1.4 CDA Activation and Coupling", Bioconjugate Techniques, pp. 615-617 (1996).
Hinman et al., "The Reactions of Methylhydrazine and unsym-Dimethylhydrazine with Esters and Anhydrides of Carboxylic Acids; the Application of Paper Chromatography to Problems in Synthetic Organic Chemistry,", J. Am. Chem. Soc. 1958, v80, pp. 1895-1900.
International Search Report and Written Opinion received in connection with international application No. PCT/US2017/049856, dated Dec. 21, 2017.
Kirstein et al., "Safety and immunogenicity of an investigational quadrivalent meningococcal conjugate vaccine (MenACYW-TT) administered to adults 56 years of age and older", 20th International Pathogenic Neisseria Conference, Manchester, United Kingdom, Abstract ID: 161, (Sep. 4-9, 2016) (1 page).
Kirstein et al., "Safety and immunogenicity of an investigational quadrivalent meningococcal conjugate vaccine (MenACYW-TT) administered to adults 56 years of age and older", 20th International

(56) References Cited

OTHER PUBLICATIONS

Pathogenic Neisseria Conference, Manchester, United Kingdom, Poster # 161 (Sep. 4-9, 2016) (1 page).
Klein et al., "Five-year Antibody Persistence and Booster Response After 1 or 2 Doses of Meningococcal A, C, W and Y Tetanus Toxoid Conjugate Vaccine in Healthy Children", The Pediatric Infectious Disease Journal, 35(6), pp. 362-672 (Jun. 2016).
Klein et al., "One or Two Doses of Quadrivalent Meningococcal Serogroups A, C, W-135 and Y Tetanus Toxoid Conjugate Vaccine Is Immunogenic in 9- to 12-Month-Old Children", The Pediatric Infectious Disease Journal, 32(7), pp. 760-767 (2013).
Knuf et al., "A dose-range study assessing immunogenicity and safety of one dose of a new candidate meningococcal serogroups A, C, W-135, Y tetanus toxoid conjugate (MenACWY-TT) vaccine administered in the second year of life and in young children", Vaccine, 28, pp. 744-753 (2010).
Knuf et al., "An investigational tetravalent meningococcal serogroups A, C, W-135 and Y-tetanus toxoid conjugate vaccine co-administered with Infanrix™ hexa is immunogenic, with an acceptable safety profile in 12-23-month-old children", Vaccine, 29, pp. 4264-4273 (2011).
Konadu et al., "Preparation, characterization, and immunological properties in mice of *Escherichia coli* O157 O-specific polysaccharide-protein conjugate vaccines", Infection and Immunity, Nov. 1994, 62 (11), pp. 5048-5054.
Lees et al., "Versatile and efficient synthesis of protein-polysaccharide conjugate vaccines using aminooxy reagents and oxime chemistry", Vaccine, vol. 24, Issue 6, Feb. 6, 2006, pp. 716-729.
Leonardi et al., "Immunogenicity and reactogenicity of Infanrix™ when co-administered with meningococcal MenACWY-TT conjugate vaccine in toddlers primed with MenHibrixTM and Pediarix™", Vaccine 33, pp. 924-932 (2015).
Leonardi et al., "Quadrivalent meningococcal (MenACWY-TT) conjugate vaccine or a fourth dose of H. influenzae-N. meningitidis C/Y conjugate vaccine (HibMenCY-TT) is immunogenic in toddlers who previously received three doses of HibMenCY-TT in infancy", Vaccine 33(7), pp. 933-941 (2015).
Lupisan et al., "Meningococcal Polysaccharide A O-Acetylation levels Do not Impact the Immunogenicity of the Quadrivalent Meningococcal Tenatus Toxoid Conjugate Vaccine: Results from a Randomized, Controlled Phase III Study of Healthy Adults aged 18 to 25 Years"; Clinical and Vaccine Immunology; vol. 20; No. 10 ; 2013; pp. 1499-1507.
McVernon et al., "A Randomized Trial to Assess Safety and Immunogenicity of Alternative Formulations of a Quadrivalent Meningococcal (A, C, Y, and W-135) Tetanus Protein Conjugate Vaccine in Toddlers", The Pediatric nfectious Disease Journal, vol. 31, No. 1, Jan. 2012.
Memish et al., "Immunogenicity of a Single Dose of Tetravalent Meningococcal Serogroups A, C, W-135, and Y Conjugate Vaccine Administered to 2- to 10-year-olds Is Noninferior to a Licensed-ACWY Polysaccharide Vaccine Nith an Acceptable Safety Profile", The Pediatric Infectious Disease Journal, 30(4), pp. e56-e62 (Apr. 2011).
Miller et al., "Conjugate Meningococcal Vaccines Development: GSK Biologicals Experience", Advances in Preventive Medicine, 2011, Article ID 846756, 17 pages.
Ostergaard et al., "Immunogenicity, reactogenicity and persistence of meningococcal A, C, W-135 and Y-tetanus toxoid candidate conjugate (MenACWY-TT) vaccine formulations in adolescents aged 15-25 year", Vaccine, 27, pp. 161-168 (2009).
Ostergaard et al., "Persistence of antibodies for 42 months following vaccination of adolescents with a meningococcal serogroups A, C, W-135, and Y tetanus toxoid conjugate vaccine (MenACWY-TT)", Int J Infect Dis, 17, pp. 173-176 (2013).
Papaevangeloo V. et al: "MenACWY-TT vaccine for active immunization against invasive meningogoccal disease"; Expert Review of Vaccines ; vol. 11, No. 5, 2012, pp. 523-537.
Paul et al., "N,N'-Carbonyldiimidazole, a new peptide forming reagent", J. Am. Chem. Soc . . . 82, pp. 4596-4600 (1960).
Reyes et al., "The investigational meningococcal serogroups A,C, W-135 and Y tetanus toxoid conjugate vaccine (ACWY-TT) and the seasonal influenza virus vaccine are immunogenic and well-tolerated when co-administered in adults", Human Vaccines & Immunotherapeutics, 8:7, pp. 881-887 (2012).
Sanderson et al., "A simple method for coupling proteins to insoluble polysaccharides", Immunology, 20, pp. 1061-1065 (1971).
Wilchek et al., "Labeling glycoconjugates with hydrazide reagents", Methods in Enzymology (V. Ginsburg, ed.), vol. 138, p. 429-442 (1987).
Tontini, Marta, "Characterization of carbohydrate based vaccines", PhD Thesis, The University of Cergy-Pontoise, Oct. 26, 2012.
Van Lenten et al., "Studies on the chemical and enzymatic modifications of glycoproteins. A general method for the tritiation of sialic acid-containing glycoproteins.", J. Biol. Chem, 246:1889-1894 (1971).
Vesikari et al., "A randomized study to assess the immunogenicity, antibody persistence and safety of a tetravalent meningococcal serogroups A, C, W-135 and Y tetanus toxoid conjugate vaccine in children aged 2-10 years", Human Vaccines & Immunotherapeutics, 8:12, pp. 1882-1891 (2012).
Vesikari et al., "Antibody persistence to meningococcal serogroups A, C, W and Y in toddlers two years after vaccination with a quadrivalent meningococcal ACWY-tetanus toxoid conjugate (MenACWY-TT) vaccine as measured by bactericidal antibody assays using rabbit or human complement", Trials in Vaccinology, 3, pp. 121-126 (2014).
Vesikari et al., "Antibody persistence up to 5 years after vaccination of toddlers and children between 12 months and 10 years of age with a quadrivalent meningococcal ACWY-tetanus toxoid conjugate vaccine", Human Vaccines & Immunotherapeutics, 12:1, 132-139 (2016).
Vesikari et al., "Immunogenicity, Safety and Antibody Persistence of a Booster Dose of Quadrivalent Meningococcal ACWY-tetanus Toxoid Conjugate Vaccine Compared with Monovalent Meningococcal Serogroup C Vaccine Administered Four Years After Primary Vaccination Using the Same Vaccines", The Pediatric Infectious Disease Journal, 34(12), pp. e298-e307 (2015).

* cited by examiner

Serogroup A Conjugate

Serogroup C Conjugate

Fig. 2B

Serogroup W135 or Y Conjugate

NEISSERIA MENINGITIDIS VACCINE

I. INTRODUCTION AND SUMMARY

This application is a divisional of U.S. application Ser. No. 16/282,080, filed Feb. 21, 2019, which is a continuation of International Patent Application No. PCT/US2017/049856, filed Sep. 1, 2017, which claims the benefit under 35 U.S.C. 119(e) of U.S. Provisional Application No. 62/383,279, filed Sep. 2, 2016; U.S. Provisional Application No. 62/468,695, filed Mar. 8, 2017; and U.S. Provisional Application No. 62/505,525, filed May 12, 2017, each of which is incorporated by reference herein in its entirety.

*Neisseria meningitidis* (*N. meningitidis*) is a leading cause of bacterial meningitis and sepsis throughout the world. Serogroups A, C, Y, and W-135 of *Neisseria meningitidis* (MenA, MenC, MenY, and MenW, respectively; collectively referred to as MenACYW) are responsible for a substantial portion of meningococcal diseases worldwide. There are currently six types of vaccines to protect against *N. meningitidis*—quadrivalent meningococcal conjugate vaccines such as Menactra® Nimenrix® and Menveo®; meningococcal polysaccharide vaccine such as Menomune, Serogroup C meningococcal vaccines such as Neisvac-C®, Menjugate® and Menitorix®, Serogroup A meningococcal vaccines such as MenAfriVac®, Serogroups C and Y meningococcal vaccines such as MenHibrix®, and Serogroup B meningococcal vaccines such as Bexsero® and Trumenba®.

The epidemiology of *N. meningitidis* can be described as complex, unpredictable, geographically variable and changing over time. As such, a need exists for development of improved *N. meningitidis* vaccines. In particular, existing polysaccharide conjugate vaccines may not be suitable for administration to one or more of infants, toddlers, adolescents, and/or older adults, or may result in a weak or undetectable seroresponse in some recipients.

In some embodiments, compositions, methods, and/or uses disclosed herein provide one or more benefits, or at least provide the public with a useful choice. Such benefits can include one or more of improved immunogenicity against one, two, three, or all four of MenA, MenC, MenY, and MenW; immunogenicity in two, three, or four of infants, toddlers, adolescents, and older adults; and sufficient stability to permit long-term storage as a liquid formulation, e.g., for multiple years under refrigeration (e.g., 2.5, 3, 3.5, 4, or 4.5 years) or multiple months at room temperature (e.g., 2, 3, 4, 5, or 6 months).

Accordingly, the following embodiments are provided. Embodiment 1 is a *Neisseria meningitidis* vaccine composition comprising: a) a first conjugate of MenA capsular polysaccharide to a carrier protein; b) a second conjugate of MenC capsular polysaccharide to a carrier protein; c) a third conjugate of MenW-135 capsular polysaccharide to a carrier protein; and d) a fourth conjugate of MenY capsular polysaccharide to a carrier protein; wherein the second conjugate is a population comprising double-end-linked conjugated polysaccharides and single-end-linked conjugated polysaccharides which both are attached to the carrier protein through a secondary amine, and the polysaccharides of the second conjugate have an O-acetylation level of 0.3 µmol/mg polysaccharide to 1.6 µmol/mg polysaccharide. The level of 0-acetylation can be greater than or equal to 0.4, 0.5, 0.6, 0.7, 0.8, 0.9, 1.0, 1.1, or 1.2 µmol/mg polysaccharide. The level of O-acetylation can be less than or equal to 0.7, 0.8, 0.9, 1.0, 1.1, 1.2, 1.3, 1.4, or 1.5 µmol/mg polysaccharide. For example, the level can range from 0.6 to 1.5 µmol/mg polysaccharide or 0.8 to 1.4 µmol/mg polysaccharide. O-acetyl content can be measured by the Hestrin method (Hestrin et. al., J. Biol. Chem. 1949, 180, p. 249).

Embodiment 2 is a *Neisseria meningitidis* vaccine composition comprising: a) a first conjugate of MenA capsular polysaccharide to a carrier protein; b) a second conjugate of MenC capsular polysaccharide to a carrier protein; c) a third conjugate of MenW-135 capsular polysaccharide to a carrier protein; and d) a fourth conjugate of MenY capsular polysaccharide to a carrier protein; wherein the second conjugate is a population comprising single-end-linked conjugated polysaccharides which are attached to the carrier protein through a secondary amine, wherein the single-end-linked conjugated polysaccharides have a terminal unlinked saccharide, wherein the terminal saccharide has a primary hydroxyl or secondary amine linkage at the 7 position, or wherein the reducing end is modified with a (2-hydroxy) ethoxy or secondary amine linkage. The second conjugate population can further comprise double-end-linked conjugates having carrier proteins linked to both ends of the polysaccharide, e.g., through a secondary amine.

Embodiment 3 is a *Neisseria meningitidis* vaccine composition comprising: a) a first conjugate of MenA capsular polysaccharide to a carrier protein; b) a second conjugate of MenC capsular polysaccharide to a carrier protein; c) a third conjugate of MenW-135 capsular polysaccharide to a carrier protein; and d) a fourth conjugate of MenY capsular polysaccharide to a carrier protein; wherein the MenA capsular polysaccharide is attached to the carrier protein through a linker comprising a carbamate, a spacer, and an amide, wherein the spacer is between the carbamate and the amide and comprises 2-10 linear carbons, and the first conjugate has a polysaccharide to carrier protein mass ratio of 0.3 to 1.5. The first conjugate can have a polysaccharide to carrier protein mass ratio of, e.g., 0.3 to 0.4, 0.4 to 0.5, 0.5 to 0.6, 0.6 to 0.7, 0.7 to 0.8, 0.8 to 0.9, 0.9 to 1.0, 1.0 to 1.1, 1.1 to 1.2, 1.2 to 1.3, 1.3 to 1.4, or 1.4 to 1.5.

Embodiment 4 is a *Neisseria meningitidis* vaccine composition comprising: a) a first conjugate of MenA capsular polysaccharide to a carrier protein; b) a second conjugate of MenC capsular polysaccharide to a carrier protein; c) a third conjugate of MenW-135 capsular polysaccharide to a carrier protein; and d) a fourth conjugate of MenY capsular polysaccharide to a carrier protein; wherein the MenA capsular polysaccharide is attached to the carrier protein through a linker comprising a carbamate, a spacer, and an amide, wherein the spacer is between the carbamate and the amide and comprises 2-10 linear carbons; and wherein the MenC, MenW-135, and MenY capsular polysaccharides are attached to the carrier protein through a secondary amine; and at least one of the conjugates has a weight average molecular weight ranging from 300 kDa to 1500 kDa.

Embodiment 5 is a *Neisseria meningitidis* vaccine composition comprising: a) a first conjugate of MenA capsular polysaccharide to a carrier protein; b) a second conjugate of MenC capsular polysaccharide to a carrier protein; c) a third conjugate of MenW-135 capsular polysaccharide to a carrier protein; and d) a fourth conjugate of MenY capsular polysaccharide to a carrier protein; wherein the carrier protein is tetanus toxoid; one or more of the first, second, third, and fourth conjugates has a weight average molecular weight ranging from 300 kDa to 1500 kDa; and the composition comprises less than 20% free polysaccharide by weight relative to total polysaccharide. At least one, two, three, or four of the conjugates in the composition can have a weight-average molecular weight ranging from 300 kDa to 1500 kDa. The weight-average molecular weight of at least one, two, three, or four of the conjugates in the composition can be greater than or equal to 400 kDa, 500 kDa, 600 kDa, 700 kDa, 800 kDa, 900 kDa, 1000 kDa, or 1100 kDa. The weight-average molecular weight of at least one, two, three, or four of the conjugates in the composition can be less than or equal to 600 kDa, 700 kDa, 800 kDa, 900 kDa, 1000 kDa, 1100 kDa, 1200 kDa, 1300 kDa, or 1400 kDa. At least one conjugate can have a molecular weight in the range of 700-800, 800-900, 900-1000, 1000-1100, 1100-1200, 1200-1300, 1300-1400, or 1400-1500 kDa. The MenA conjugate can have a molecular weight in the range of 700-800, 800-900, 900-1000, 1000-1100, 1100-1200, 1200-1300, 1300-1400, or 1400-1500 kDa. The MenC conjugate can have a molecular weight in the range of 700-800, 800-900, 900-1000, 1000-1100, 1100-1200, 1200-1300, 1300-1400, or 1400-1500 kDa. The MenY conjugate can have a molecular weight in the range of 700-800, 800-900, 900-1000, 1000-1100, 1100-1200, 1200-1300, 1300-1400, or 1400-1500 kDa. The MenW-135 conjugate can have a molecular weight in the range of 700-800, 800-900, 900-1000, 1000-1100, 1100-1200, 1200-1300, 1300-1400, or 1400-1500 kDa.

Embodiment 6 is a *Neisseria meningitidis* vaccine composition comprising: a) a first conjugate of MenA capsular polysaccharide to a carrier protein; b) a second conjugate of MenC capsular polysaccharide to a carrier protein; c) a third conjugate of MenW-135 capsular polysaccharide to a carrier protein; and d) a fourth conjugate of MenY capsular polysaccharide to a carrier protein; wherein the carrier protein is tetanus toxoid; one or more of the first, second, third, and fourth conjugates have a polysaccharide to carrier protein mass ratio of 0.3 to 1.5; and the composition comprises less than 20% free polysaccharide by weight relative to total polysaccharide. The first conjugate can have a polysaccharide to carrier protein mass ratio of, e.g., 0.3 to 0.4, 0.4 to 0.5, 0.5 to 0.6, 0.6 to 0.7, 0.7 to 0.8, 0.8 to 0.9, 0.9 to 1.0, 1.0 to 1.1, 1.1 to 1.2, 1.2 to 1.3, 1.3 to 1.4, or 1.4 to 1.5. The second conjugate can have a polysaccharide to carrier protein mass ratio of, e.g., 0.3 to 0.4, 0.4 to 0.5, 0.5 to 0.6, 0.6 to 0.7, 0.7 to 0.8, 0.8 to 0.9, 0.9 to 1.0, 1.0 to 1.1, 1.1 to 1.2, 1.2 to 1.3, 1.3 to 1.4, or 1.4 to 1.5. The third conjugate can have a polysaccharide to carrier protein mass ratio of, e.g., 0.3 to 0.4, 0.4 to 0.5, 0.5 to 0.6, 0.6 to 0.7, 0.7 to 0.8, 0.8 to 0.9, 0.9 to 1.0, 1.0 to 1.1, 1.1 to 1.2, 1.2 to 1.3, 1.3 to 1.4, or 1.4 to 1.5. The fourth conjugate can have a polysaccharide to carrier protein mass ratio of, e.g., 0.3 to 0.4, 0.4 to 0.5, 0.5 to 0.6, 0.6 to 0.7, 0.7 to 0.8, 0.8 to 0.9, 0.9 to 1.0, 1.0 to 1.1, 1.1 to 1.2, 1.2 to 1.3, 1.3 to 1.4, or 1.4 to 1.5.

Embodiment 7 is the vaccine composition of any one of the preceding embodiments, wherein the first, second, third, and/or fourth conjugates are a population comprising molecules with a molecular weight in the range of 700 kDa to 1400 kDa or 800 kDa to 1300 kDa. The first and second conjugates can be a population comprising molecules with a molecular weight in the range of 700 kDa to 1400 kDa or 800 kDa to 1300 kDa. The first and third conjugates can be a population comprising molecules with a molecular weight in the range of 700 kDa to 1400 kDa or 800 kDa to 1300 kDa. The first and fourth conjugates can be a population comprising molecules with a molecular weight in the range of 700 kDa to 1400 kDa or 800 kDa to 1300 kDa. The second and third conjugates can be a population comprising molecules with a molecular weight in the range of 700 kDa to 1400 kDa or 800 kDa to 1300 kDa. The second and fourth conjugates can be a population comprising molecules with a molecular weight in the range of 700 kDa to 1400 kDa or 800 kDa to 1300 kDa. The third and fourth can be a population comprising molecules with a molecular weight in the range of 700 kDa to 1400 kDa or 800 kDa to 1300 kDa.

Embodiment 8 is a *Neisseria meningitidis* vaccine composition comprising a conjugate of MenC capsular polysaccharide to a carrier protein, wherein the conjugate is a population comprising double-end-linked conjugated polysaccharides and single-end-linked conjugated polysaccharides which both are attached to the carrier protein through a secondary amine, and the polysaccharides of the conjugate of MenC capsular polysaccharide to the carrier protein have an O-acetylation level ranging from 0.3 μmol/mg polysaccharide to 1.6 μmol/mg polysaccharide. The level of O-acetylation can be greater than or equal to 0.4, 0.5, 0.6, 0.7, 0.8, 0.9, 1.0, 1.1, or 1.2 μmol/mg polysaccharide. The level of O-acetylation can be less than or equal to 0.7, 0.8, 0.9, 1.0, 1.1, 1.2, 1.3, 1.4, or 1.5 μmol/mg polysaccharide. E.g., the level can range from 0.6 to 1.5 μmol/mg polysaccharide or 0.8 to 1.4 μmol/mg polysaccharide. O-acetyl content can be measured by the Hestrin method (Hestrin et. al., J. Biol. Chem. 1949, 180, p. 249).

Embodiment 9 is the vaccine composition of embodiment 8, wherein the conjugate (a) has a weight average molecular weight ranging from 300 kDa to 1500 kDa; or (b) is a population comprising molecules having a molecular weight in the range of 700 kDa to 1400 kDa or 800 kDa to 1300 kDa.

Embodiment 10 is the vaccine composition of any one of embodiments 4, 5, 7, or 9, wherein molecular weight is determined by multi-angle light scattering (MALS).

Embodiment 11 is the vaccine composition of any one of the preceding embodiments, wherein the MenC polysaccharide has a degree of O-acetylation ranging from 0.6 to 1.5 μmol/mg polysaccharide or 0.8 to 1.4 μmol/mg polysaccharide.

Embodiment 12 is the vaccine composition of embodiment 11, wherein the degree of O-acetylation is greater than or equal to 0.7, 0.8, 0.9, 1.0, 1.1, or 1.2 μmol/mg polysaccharide.

Embodiment 13 is the vaccine composition of embodiment 11, wherein the degree of O-acetylation is less than or equal to 0.8, 0.9, 1.0, 1.1, 1.2, 1.3, or 1.4 μmol/mg polysaccharide.

Embodiment 14 is the vaccine composition of any one of the preceding embodiments, wherein the conjugate comprising MenC polysaccharide is a population comprising double-end-linked conjugated polysaccharides and single-end-linked conjugated polysaccharides.

Embodiment 15 is the vaccine composition of embodiment 14, wherein the single-end-linked polysaccharides of the second conjugate comprise a terminal unlinked saccharide, wherein the single-end-linked conjugated polysaccharides have a terminal unlinked saccharide, wherein the terminal saccharide has a primary hydroxyl at the 7 position, or wherein the reducing end is modified with a (2-hydroxy) ethoxy.

Embodiment 16 is the vaccine composition of any one of the preceding embodiments, wherein the conjugate comprising MenC polysaccharide comprises one or more modifications chosen from (i) a primary hydroxyl at the 7 position, (ii) a (2-hydroxy)ethoxy at the reducing end, and (iii) a conjugation to the carrier protein, wherein the modifications are present at no less than 25 nmol/mg polysaccharide.

Embodiment 17 is the vaccine composition of any one of the preceding embodiments, comprising a conjugate of MenW-135 and/or MenY polysaccharide which comprises one or more modifications chosen from (i) a primary hydroxyl at a position of a vicinal diol in a native MenW-135 or MenY polysaccharide and (ii) a conjugation to the carrier protein, wherein the modifications are present at no less than 60 nmol/mg polysaccharide.

Embodiment 18 is the vaccine composition of embodiment 16 or 17, wherein the modifications are present in an amount less than 200 nmol/mg polysaccharide, less than 150 nmol/mg polysaccharide, less than 100 nmol/mg polysaccharide, or less than 80 nmol/mg polysaccharide.

Embodiment 19 is the vaccine composition of any one of the preceding embodiments, wherein the MenC polysaccharide is reduced in size by 3×-8× relative to native MenC polysaccharide.

Embodiment 20 is the vaccine composition of any one of the preceding embodiments, comprising a conjugate of MenA capsular polysaccharide to a carrier protein having a polysaccharide to carrier protein mass ratio of 0.5 to 1.5. Embodiment 20A is the vaccine composition of embodiment 20, comprising a conjugate of MenA capsular polysaccharide to a carrier protein having a polysaccharide to carrier protein mass ratio of 0.7 to 1.4.

Embodiment 21 is the vaccine composition of embodiment 20, wherein the MenA conjugate has a polysaccharide to carrier protein mass ratio of 0.8 to 1.3.

Embodiment 22 is the vaccine composition of any one of the preceding embodiments, comprising a conjugate of MenC and/or MenY capsular polysaccharide to a carrier protein having a polysaccharide to carrier protein mass ratio of 0.3 to 1.1.

Embodiment 23 is the vaccine composition of embodiment 22, wherein the MenC conjugate has a polysaccharide to carrier protein mass ratio of 0.4 to 0.8.

Embodiment 24 is the vaccine composition of any one of the preceding embodiments, comprising a conjugate of MenW-135 capsular polysaccharide to a carrier protein having a polysaccharide to carrier protein mass ratio of 0.3 to 1.3.

Embodiment 25 is the vaccine composition of embodiment 24, wherein the MenW-135 conjugate has a polysaccharide to carrier protein mass ratio of 0.6 to 1.3.

Embodiment 26 is the vaccine composition any one of the preceding embodiments, comprising a conjugate of MenY capsular polysaccharide to a carrier protein having a polysaccharide to carrier protein mass ratio of 0.5 to 1.3.

Embodiment 27 is the vaccine composition of embodiment 26, wherein the MenY conjugate has a polysaccharide to carrier protein mass ratio of 0.5 to 0.9.

Embodiment 28 is the vaccine composition of any one of the preceding embodiments, wherein the composition comprises less than 20% free polysaccharide by weight.

Embodiment 29 is the vaccine composition of embodiment 28, wherein the composition comprises less than 10% free polysaccharide by weight, less than 5% free polysaccharide by weight, or substantially lacks free polysaccharide.

Embodiment 30 is the vaccine composition of any one of the preceding embodiments, wherein the polysaccharide of the MenA, MenC, MenW-135, or MenY conjugate is attached to the carrier protein through a linker.

Embodiment 31 is the vaccine composition of embodiment 30, wherein the linker comprises 2-10 linear carbons.

Embodiment 32 is the vaccine composition of embodiments 30 and 31, wherein the linker is present in the MenA, MenC, MenW-135, or MenY conjugate at a ratio of one linker per 10-100 saccharide repeat units.

Embodiment 33 is the vaccine composition of embodiments 30 and 31, wherein the linker is present in the MenA, MenC, MenW-135, or MenY conjugate at a ratio of one linker per 20-60 saccharide repeat units.

Embodiment 34 is the vaccine composition of embodiments 30 and 31, wherein the linker comprises a spacer between a first carbonyl and a second carbonyl, and the spacer comprises 4-8 carbons.

Embodiment 35 is the vaccine composition of any one of embodiments 30-34, wherein the linker of the MenA conjugate comprises a residue of a dihydrazide.

Embodiment 36 is the vaccine composition of embodiment 35, wherein the linker of the MenA conjugate comprises a residue of adipic acid dihydrazide.

Embodiment 37 is the vaccine composition of any one of the preceding embodiments, wherein the polysaccharide of the MenA, MenC, MenW-135, and/or MenY conjugate is attached to the carrier protein through a linker of formula I:

$$PS-O-\underset{O}{\overset{O}{C}}-\underset{H}{\overset{H}{N}}-\underset{H}{\overset{}{N}}-\underset{O}{\overset{O}{C}}-(CH_2)_4-\underset{O}{\overset{O}{C}}-\underset{H}{\overset{H}{N}}-\underset{H}{\overset{}{N}}-\underset{O}{\overset{O}{C}}-PR \quad (I)$$

wherein PS indicates attachment to the polysaccharide and PR indicates attachment to the carrier protein.

Embodiment 38 is the vaccine composition of any one of embodiments 30-37, wherein the linker is in the MenA conjugate.

Embodiment 39 is the vaccine composition of any one of embodiments 30-37, wherein the linker is in the MenC conjugate.

Embodiment 40 is the vaccine composition of any one of embodiments 30-37, wherein the linker is in the MenW-135 conjugate.

Embodiment 41 is the vaccine composition of any one of embodiments 30-37, wherein the linker is in the MenY conjugate.

Embodiment 42 is the vaccine composition of any one of the preceding embodiments, wherein the polysaccharide of the MenA, MenC, MenW-135, and/or MenY conjugate is attached to the carrier protein as shown in formula II: PR—NH—CH$_2$—PS (II) wherein PS indicates attachment to the polysaccharide and PR indicates attachment to the carrier protein.

Embodiment 43 is the vaccine composition of embodiment 42, wherein the polysaccharide of the MenA conjugate is attached to the carrier protein as shown in formula II.

Embodiment 44 is the vaccine composition of embodiment 42, wherein the polysaccharide of the MenC conjugate is attached to the carrier protein as shown in formula II.

Embodiment 45 is the vaccine composition of embodiment 42, wherein the polysaccharide of the MenW-135 conjugate is attached to the carrier protein as shown in formula II.

Embodiment 46 is the vaccine composition of embodiment 42, wherein the polysaccharide of the MenY conjugate is attached to the carrier protein as shown in formula II.

Embodiment 47 is the vaccine composition of any one of the preceding embodiments, wherein the carrier protein comprises or consists of recombinant exoprotein A (rEPA), diphtheria toxoid or a B-fragment of diphtheria toxin, CRM197, tetanus toxoid or a C-fragment of tetanus toxin.

Embodiment 48 is the vaccine composition of any one of the preceding embodiments, wherein the carrier protein is tetanus toxoid.

Embodiment 49 is a method of producing a conjugate of a *Neisseria meningitidis* capsular polysaccharide to a carrier protein, comprising: a) activating the polysaccharide with an activating agent that can form a carbamate linkage wherein the activating agent is present in a molar excess over the polysaccharide of 20-fold to 50-fold; b) partially quenching the activated polysaccharide and derivatizing the activated polysaccharide with a dihydrazide linker added at a mole ratio of 0.3 to 1.0 relative to polysaccharide repeat units, wherein the polysaccharide is derivatized at a ratio of one dihydrazide linker per 10-100 saccharide repeat units; c) conjugating the derivatized polysaccharide to the carrier protein by carbodiimide chemistry, wherein the polysaccharide is present at the beginning of the conjugation reaction at a weight-to-weight ratio of 3:1 to 5:1 relative to the carrier protein, thereby forming the conjugate.

Embodiment 50 is the method of embodiment 49, wherein the dihydrazide linker is added at a mole ratio of 0.4 to 0.6 relative to polysaccharide repeat units.

Embodiment 51 is the method of embodiment 49, comprising a further step of quenching the reaction with glycerol.

Embodiment 52 is the method of any one of embodiments 49 to 51, wherein the dihydrazide linker is adipic acid dihydrazide.

Embodiment 53 is the method of any one of embodiments 49 to 51, wherein the derivatized polysaccharide is at a starting concentration of 10 g/L to 20 g/L in the conjugation reaction.

Embodiment 54 is the method of any one of embodiments 49 to 51, wherein the activating agent comprises a carbonyl bound to two N-linked heteroaryls such as CDI (1,1'-Carbonyldiimidazole) and CDT (1,1'-Carbonyl-di-(1,2,4-triazole), or other appropriate leaving groups.

Embodiment 55 is the method of embodiment 54, wherein the activating agent is carbonyl diimidazole.

Embodiment 56 is the method of any one of embodiments 49 to 51, wherein the activating agent is present in the activating step in a molar excess over the polysaccharide of 35-fold to 45-fold.

Embodiment 57 is the method of any one of embodiments 49 to 51, wherein the conjugating step comprises reacting the carrier protein with N-Ethyl-N'-(3-dimethylaminopropyl) carbodiimide.

Embodiment 58 is the method of any one of embodiments 49 to 51, wherein the polysaccharide is MenA capsular polysaccharide.

Embodiment 59 is the method of any one of embodiments 49 to 51, wherein the polysaccharide is MenC capsular polysaccharide.

Embodiment 60 is the method of any one of embodiments 49 to 51, wherein the polysaccharide is MenW-135 or MenY capsular polysaccharide.

Embodiment 61 is a method of producing a conjugate of a *Neisseria meningitidis* capsular polysaccharide to a carrier protein, comprising: a) partially de-O-acetylating the polysaccharide by alkaline hydrolysis; b) activating the polysaccharide by periodate treatment, thereby converting diols to aldehydes to an extent of at least 20 nmol aldehyde per mg polysaccharide; c) conjugating the activated polysaccharide to the carrier protein by reductive amination, wherein the polysaccharide is present in the conjugation reaction at a weight-to-weight ratio of 1:1 to 5:1 relative to the carrier protein, thereby forming the conjugate.

Embodiment 62 is the method of embodiment 61, wherein the polysaccharide is present in the conjugation reaction at a weight-to-weight ratio of 1.5 to 3:1 relative to the carrier protein.

Embodiment 63 is the method of embodiment 61, wherein the de-O-acetylation reduces the initial amount of O-acetylation in the polysaccharide by 40% to 70%, or 50% to 60%.

Embodiment 64 is the method of any one of embodiments 61 to 63, wherein following de-O-acetylation, the polysaccharide has a degree of O-acetylation from 0.6 µmol/mg polysaccharide to 1.5 µmol/mg polysaccharide or 0.8 to 1.4 µmol/mg polysaccharide.

Embodiment 65 is the method of embodiment 64, wherein the degree of O-acetylation is greater than or equal to 0.7, 0.8, 0.9, 1.0, 1.1, or 1.2 µmol/mg polysaccharide.

Embodiment 66 is the method of embodiment 64, wherein the degree of O-acetylation is less than or equal to 0.8, 0.9, 1.0, 1.1, 1.2, 1.3, or 1.4 µmol/mg polysaccharide.

Embodiment 67 is the method of any one of embodiments 61 to 66, wherein the activated polysaccharide is at a starting concentration of 20 g/L to 50 g/L in the conjugation reaction.

Embodiment 68 is the method of any one of embodiments 61 to 66, wherein the polysaccharide is MenC capsular polysaccharide.

Embodiment 69 is the method of any one of embodiments 61 to 66, wherein the polysaccharide is MenA capsular polysaccharide.

Embodiment 70 is the method of any one of embodiments 61 to 66, wherein the polysaccharide is MenW-135 or MenY capsular polysaccharide.

Embodiment 71 is the method of any one of embodiments 61 to 66, wherein the polysaccharide is reduced in size to 30 to 150 kDa or to 50 to 100 kDa before the conjugation reaction.

Embodiment 72 is a method of producing a conjugate of a *Neisseria meningitidis* capsular polysaccharide to a carrier protein, comprising: a) activating the polysaccharide by periodate treatment, thereby converting diols to aldehydes to an extent of at least 50 nmol aldehyde per mg polysaccharide; b) conjugating the activated polysaccharide to the carrier protein by reductive amination, wherein the polysaccharide is present in the conjugation reaction at a weight-to-weight ratio of 1:1 to 5:1 relative to the carrier protein, thereby forming the conjugate.

Embodiment 73 is the method of embodiment 72, wherein the polysaccharide is present in the conjugation reaction at a weight-to-weight ratio of 1.5 to 3:1 relative to the carrier protein.

Embodiment 74 is the method of any one of embodiments 72 and 73, wherein the polysaccharide is MenW-135 or MenY capsular polysaccharide.

Embodiment 75 is the method of any one of embodiments 72 and 73, wherein the polysaccharide is MenC capsular polysaccharide.

Embodiment 76 is the method of any one of embodiments 72 and 73, wherein the polysaccharide is MenA capsular polysaccharide.

Embodiment 77 is the method of any one of embodiments 72 to 76, wherein the polysaccharide is reduced in size to 100 to 200 kDa or to 125 to 175 kDa before the conjugation reaction.

Embodiment 78 is the method of any one of embodiments 49, 61, and 72, wherein the polysaccharide is reduced in size by acid hydrolysis and/or heat.

Embodiment 79 is the method of any one of embodiments 49, 61, and 72, wherein the polysaccharide is reduced in size by oxidative cleavage.

Embodiment 80 is the method of any one of embodiments 72 to 79, wherein reductive amination comprises reducing imines to amines using a cyanoborohydride, or other reducing reagents such as pyridine borane ($C_5H_8BN$) and picoline borane complex ($C_6H_7N.BH_3$).

Embodiment 81 is the method of any one of embodiments 72 to 79, further comprising converting unreacted aldehydes in the conjugate to alcohols with a reducing reagent.

Embodiment 82 is the method of embodiment 81, wherein the reducing reagent is a borohydride.

Embodiment 83 is the method of any one of embodiments 72 to 79, wherein periodate is added to a concentration of 1 mM to 4 mM or 1.5 mM to 3 mM to activate the polysaccharide.

Embodiment 84 is the method of any one of embodiments 49 to 83, further comprising purifying the conjugate by hydrophobic interaction chromatography.

Embodiment 85 is the method of any one of embodiments 49 to 83, further comprising purifying the conjugate by mixed mode resin chromatography.

Embodiment 86 is a method of purifying a conjugate of a *Neisseria meningitidis* capsular polysaccharide to a carrier protein from a mixture containing the conjugate, a salt, and free polysaccharide, comprising: a) contacting a hydrophobic interaction chromatography resin with the mixture, wherein the conjugate binds the resin; b) eluting free polysaccharide from the resin; and c) eluting the conjugate from the resin with an aqueous liquid, wherein the aqueous liquid is free of salt or contains less salt than the mixture, thereby obtaining a composition comprising purified conjugate.

Embodiment 87 is the method of embodiment 86, wherein the salt comprises ammonium sulfate.

Embodiment 88 is the method of embodiment 86 or embodiment 87, wherein the mixture comprises salt in an amount ranging from 0.5 to 1.5 M or 0.8 to 1.2 M.

Embodiment 89 is the method of any one of embodiments 86 to 88, wherein the aqueous liquid comprises less than 0.2, 0.1, or 0.05 M salt.

Embodiment 90 is the method of any one of embodiments 86 to 89, wherein the aqueous liquid is water.

Embodiment 91 is the method of any one of embodiments 86 to 90, wherein the composition comprises less than 20% free polysaccharide by weight, less than 10% free polysaccharide by weight, less than 5% free polysaccharide by weight, or substantially lacks free polysaccharide.

Embodiment 92 is the method of any one of embodiments 86 to 91, wherein the hydrophobic interaction chromatography resin is a phenyl, propyl, or butyl resin.

Embodiment 93 is the method of any one of embodiments 49 to 92, wherein the carrier protein is tetanus toxoid.

Embodiment 94 is a conjugate produced according to the method of any one of embodiments 49 to 85.

Embodiment 95 is a vaccine composition comprising: a) a first conjugate of MenA capsular polysaccharide to a carrier protein; b) a second conjugate of MenC capsular polysaccharide to a carrier protein; c) a third conjugate of MenW-135 capsular polysaccharide to a carrier protein; and d) a fourth conjugate of MenY capsular polysaccharide to a carrier protein; wherein one, two, three, or all of the first, second, third, and fourth conjugates was produced according to the method of any one of embodiments 49 to 85.

Embodiment 96 is the vaccine composition of any one of embodiments 1-48 or 95, which is free of adjuvant.

Embodiment 97 is the vaccine composition of any one of embodiments 1-48 or 95-96, further comprising a pharmaceutically acceptable buffer.

Embodiment 98 is the vaccine composition of embodiment 97, comprising acetate buffer with a pH of 5.5 to 6.5.

Embodiment 99 is the vaccine composition of any one of embodiments 1-48 or 95-98, further comprising a pharmaceutically acceptable salt.

Embodiment 100 is the vaccine composition of embodiment 99, wherein the pharmaceutically acceptable salt is sodium chloride.

Embodiment 101 is the vaccine composition of embodiment 99 or 100, wherein the pharmaceutically acceptable salt is present at 0.45% to 0.9% w/v, or 0.5% w/v to 0.85% w/v.

Embodiment 102 is the vaccine composition of any one of embodiments 1-48 or 95-101, wherein at least one, two, three, or all four of the first, second, third, and fourth conjugates comprise multiple points of attachment between the polysaccharides and the carrier proteins.

Embodiment 103 is the vaccine composition of any one of embodiments 1-48 or 95-102, formulated for intramuscular administration.

Embodiment 104 is a single unit dose of the vaccine composition of any one of embodiments 1-48 or 95-103, comprising from 6 µg to 15 µg of each of the MenA, MenC, MenW-135, and MenY polysaccharides.

Embodiment 105 is the single unit dose of embodiment 104, wherein the carrier protein is present in an amount from 50 µg to 80 µg.

Embodiment 106 is the single unit dose of embodiment 104 or 105, which is contained in a syringe.

Embodiment 107 is the single unit dose of embodiment 106, wherein the syringe is silicone-free.

Embodiment 108 is the single unit dose of embodiment 106 or 107, wherein the syringe is packaged for commercial sale or distribution.

Embodiment 109 is a method of vaccinating a subject against *Neisseria meningitidis* comprising administering a dose of the vaccine composition of any one of embodiments 1-48 or 95-103 to the subject. Embodiment 109A is the vaccine composition of any one of embodiments 1-48 or 95-103 for use in a method of vaccinating a subject against *Neisseria meningitidis* comprising administering a dose of the vaccine composition to the subject.

Embodiment 110 is use of the vaccine composition of any one of embodiments 1-48 or 95-103 or the single unit dose of any one of embodiments 104-108 to immunize a subject against *Neisseria meningitidis*. Embodiment 110A is the vaccine composition of any one of embodiments 1-48 or 95-103 or the single unit dose of any one of embodiments 104-108 for use in immunizing a subject against *Neisseria meningitidis*.

Embodiment 111 is use of the vaccine composition of any one of embodiments 1-48 or 95-103 or the single unit dose of any one of embodiments 104-108 for the manufacture of a medicament for immunizing a subject against *Neisseria meningitidis*. Embodiment 111A is the vaccine composition of any one of embodiments 1-48 or 95-103 or the single unit dose of any one of embodiments 104-108 for use as a medicament for immunizing a subject against *Neisseria meningitidis*.

Embodiment 112 is the method, use, or composition of any one of embodiments 109-111A, wherein the vaccine is administered intramuscularly.

Embodiment 113 is the method, use, or composition of any one of embodiments 109-112, wherein the subject is age 6 weeks to 3 years.

Embodiment 114 is the method, use, or composition of embodiment 113, wherein the subject is 2 months, 6 months, 12 months, or 15 months of age.

Embodiment 115 is the method, use, or composition of any one of embodiments 109-112, wherein the subject is age 50 years or more, 55 years or more, 60 years or more, or 65 years or more.

Embodiment 116 is the method, use, or composition of any of embodiments 109-115, wherein the vaccine is administered as a 0.5 mL dose.

Embodiment 117 is the method, use, or composition of embodiment 116, wherein the vaccine comprises 4-10 μg each of serogroups A, C, Y, and W-135.

Embodiment 118 is the method, use, or composition of embodiment 116, wherein the vaccine comprises 50-80 μg of tetanus toxoid protein.

Embodiment 119 is the method, use, or composition of embodiment 116, wherein the vaccine comprises 4-10 μg each of serogroups A, C, Y, and W-135, and 50-80 μg of tetanus toxoid protein.

Embodiment 120 is the method, use, or composition of any of embodiments 109-119, further comprising administering a vaccine that is not directed to *Neisseria meningitidis* at the same time as, but not in the same injection as, the MenACYW-TT vaccine.

Embodiment 121 is the method, use, or composition of embodiment 120, wherein non-*Neisseria meningitidis* vaccine is directed to preventing varicella, diphtheria, Hib, hepatitis b, measles, mumps, pertussis, polio, pneumococcus, rotavirus, rubella, or tetanus infections.

Embodiment 122 is the method, use, or composition of embodiment 120, wherein the non-*Neisseria meningitidis* vaccine is DTaP5, Hib, HepB, DTap5-IPV/Hib, DTap5-IPV/Hib, HepB, MMR, IPV, PCV7, PCV13, RV1 or RV5.

Embodiment 123 is the method, use, or composition of any one of embodiments 109-122, wherein the subject previously received a *Neisseria meningitidis* capsular saccharide conjugate vaccine.

Embodiment 124 is the method, use, or composition of embodiment 123, wherein the subject received the *Neisseria meningitidis* capsular saccharide conjugate vaccine four months to ten years earlier. Embodiment 124A is the method, use, or composition of embodiment 123, wherein the subject received the *Neisseria meningitidis* capsular saccharide conjugate vaccine two months to ten years earlier.

Embodiment 125 is the method, use, or composition of any one of embodiments 109-122, wherein the subject did not previously receive a *Neisseria meningitidis* capsular saccharide conjugate vaccine.

II. BRIEF DESCRIPTION OF THE FIGURES

FIG. 1A shows a schematic of a Serogroup A Polysaccharide-ADH linked protein Conjugate. Serogroup A polysaccharides 10 with reactive site residues 11 formed by activation with carbonyl diimidazole (CDI) and optionally derivatization with adipic acid dihydrazide (ADH) at hydroxyl groups of the polysaccharide and reaction with a protein (e.g., Tetanus Toxoid (TT)). Activated/derivatized polysaccharide is crosslinked to the protein 13 through a linkage 12 directly or indirectly at groups 14. For example, direct linkages can use primary amines of the protein, e.g., by forming a carbamate linkage (e.g., derived from CDI). Indirect linkages can be derived from ADH and N-Ethyl-N-(3-dimethylaminopropyl)carbodiimide (EDAC), which activates carboxyls of the protein.

FIG. 1B illustrates preparation of an active O-acylisourea intermediate of a carrier protein (e.g., TT) using N-Ethyl-N-(3-dimethylaminopropyl)carbodiimide (EDAC), which reacts with carboxyl groups (e.g., on aspartic acid or glutamic acid side chains, or the C-terminus) of the protein. This intermediate is suitable for coupling to amine groups of an activated derivatized polysaccharide (not shown).

FIG. 1C illustrates a general scheme for producing activated derivatized Serogroup A polysaccharide, which can be used to produce a Serogroup A Polysaccharide-ADH Conjugate linked to a carrier protein (e.g., TT). In this embodiment, polysaccharides are activated at hydroxyl groups with CDI, forming an imidazole carbamate active intermediate, which is further derivatized with ADH. The ADH-derivatized Serogroup A polysaccharide is suitable for covalent attachment to the carrier protein via amine coupling of the primary amine groups on the ADH linker to an active O-acylisourea intermediate of the carrier protein (not shown).

FIG. 1D shows a general scheme for producing a Serogroup A Polysaccharide linked to Tetanus Toxoid Conjugate via a carbamate. Polysaccharides (PS) are activated at hydroxyl groups with CDI, forming an imidazole carbamate active intermediate. The active intermediate is then reacted with a protein carrier (PR). A carbamate linkage is formed through a nucleophilic substitution reaction in which a primary amine of the protein attacks the carbamate carbon, resulting in loss of imidazole and formation of a carbamate linkage between the polysaccharide and protein.

FIGS. 1E-F show the structure of a Serogroup A polysaccharide (E) following CDI-activation and (F) following CDI-activation and derivatization with ADH.

FIG. 1G illustrates producing a Serogroup A Polysaccharide-ADH Conjugate linked to a carrier protein (e.g., TT) from activated derivatized polysaccharide and an active O-acylisourea intermediate formed from Tetanus Toxoid carrier protein and N-Ethyl-N-(3-dimethylaminopropyl)carbodiimide (EDAC). The primary amine of the activated derivatized polysaccharide substitutes for the isourea, which serves as a leaving group, giving a product in which the protein is linked to the polysaccharide through an amide bond, the residue of ADH, and a carbamate linkage, in which the carbonyl is derived from CDI. The eliminated urea by-product is not shown.

Figures 2A, 2B:
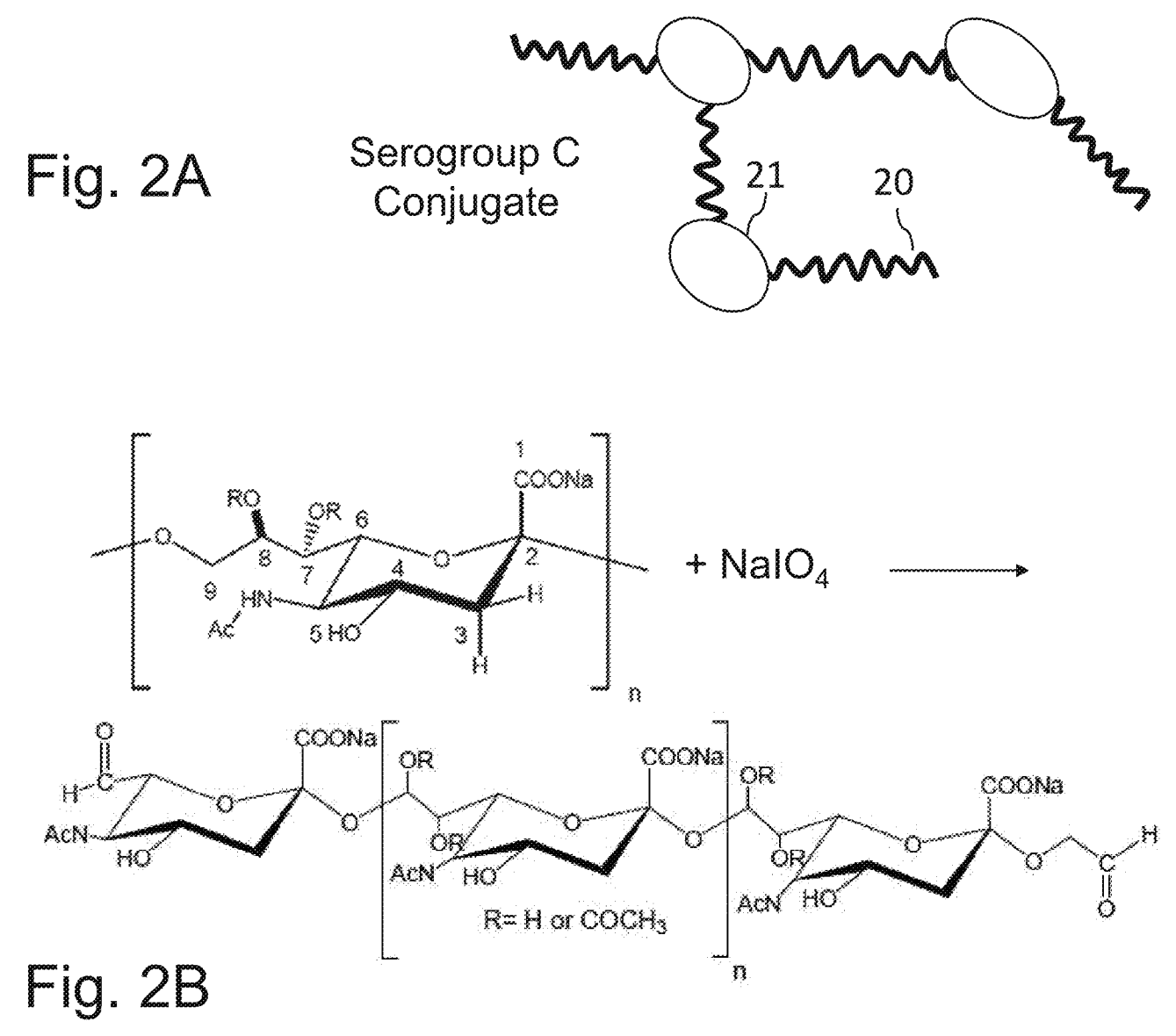
Figure 2C:
FIG. 2A shows a schematic of a Serogroup C Polysaccharide-Protein Conjugate. Serogroup C polysaccharides 20 are bonded to a protein (e.g., Tetanus Toxoid) 21 at their termini.
FIG. 2B illustrates activation of Serogroup C Polysaccharide (shown with conventional numbering of the carbons in the polysaccharide repeat unit) using sodium metaperiodate. Sodium metaperiodate treatment results in cleavage between the 7 and 8 carbons, oxidatively depolymerizing the polysaccharide into corresponding terminal aldehydes.

FIG. 2C illustrates formation of a Serogroup C Polysaccharide-protein (e.g., TT) conjugate via reductive amination. A primary amine of the protein (PR) (e.g., lysine side chain or N-terminus) reacts with a terminal aldehyde of a depolymerized, activated Serogroup C Polysaccharide (PS) to form a Schiff base intermediate (not shown), which is reduced (e.g., using pyridine borane, picoline borane, or a cyanoborohydride) to give a secondary amine linkage. The polysaccharide moiety is end-linked to the protein. Individual protein molecules may react with more than one polysaccharide and some polysaccharide termini may be unreacted (not shown; see illustration in FIG. 2A). Unreacted aldehydes can be capped, i.e., reduced to alcohols, using a suitable reducing agent such as sodium borohydride after reduction of the Schiff base (not shown).

Figure 2D:
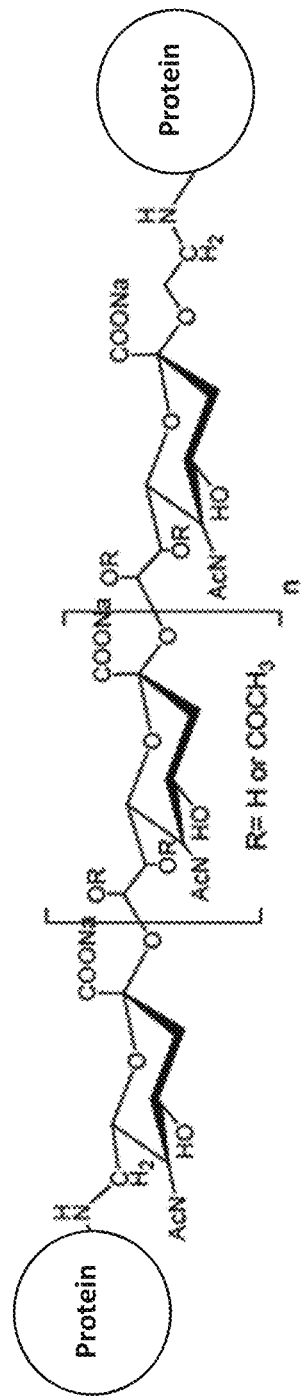

FIG. 2D shows the product of the reaction in FIG. 2C with the structure of the linked polysaccharide repeat unit drawn out. Linkage of the protein to additional polysaccharides is possible (not shown).

Figure 3:
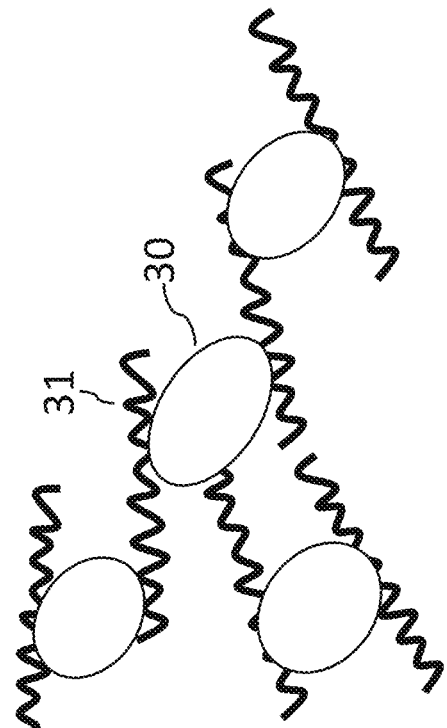

FIG. 3 shows a schematic of a Serogroup W-135 or Serogroup Y Polysaccharide-Protein Conjugate. Serogroup W-135 or Serogroup Y polysaccharides 31 are bonded to one or more proteins (e.g., Tetanus Toxoid) 30 at one or more positions.

Figure 4A:
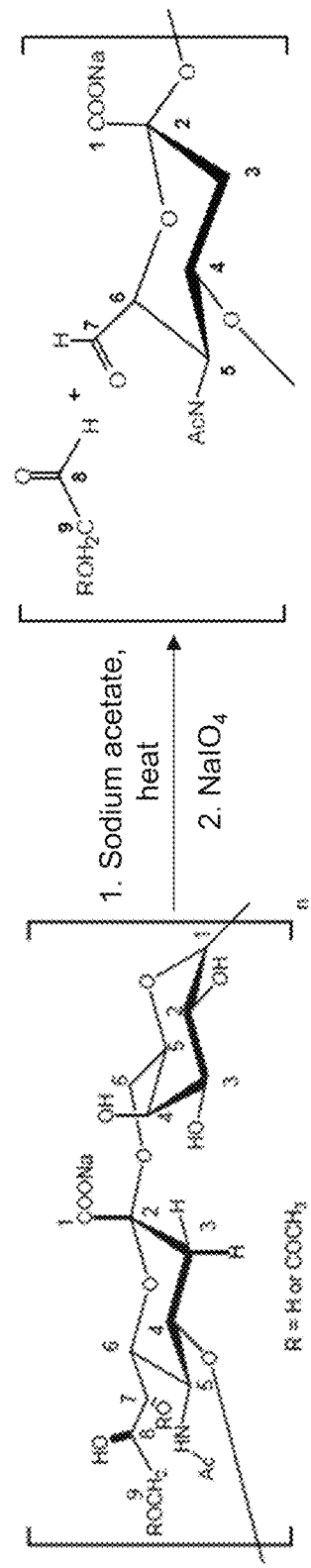

FIG. 4A illustrates depolymerization and activation of Serogroup W-135 Polysaccharide. The polysaccharide is depolymerized using, e.g., elevated temperature and then activated by treatment with sodium metaperiodate, which cleaves vicinal diols such as, for example, between carbon 7 and 8 of the sialic acid moiety and oxidizes them to aldehydes.

Figure 4B:

FIG. 4B illustrates formation of a Serogroup W-135 Polysaccharide-protein (e.g., TT) conjugate via reductive amination. A primary amine of the protein (PR) (e.g., lysine side chain or N-terminus) reacts with an aldehyde of a depolymerized, activated Serogroup W-135 Polysaccharide (PS) to form a Schiff base intermediate (not shown). The intermediate is reduced by sodium cyanoborohydride to give a secondary amine linkage. Individual protein molecules may react with more than one polysaccharide and vice versa (not shown; see illustration in FIG. 3). Unreacted aldehydes can be capped, i.e., reduced to alcohols, using a suitable reducing agent such as sodium borohydride after reduction of the Schiff base (not shown).

Figure 4C:
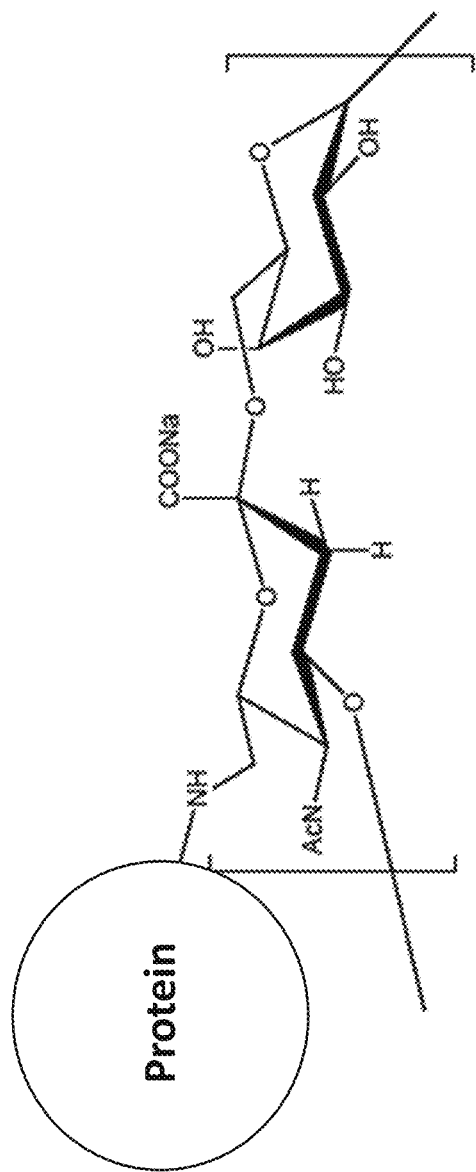

FIG. 4C shows a product of the reaction in FIG. 4B with one possible structure of the linked polysaccharide repeat unit drawn out. Linkage of the protein to additional polysaccharides or vice versa are possible (not shown; see illustration in FIG. 3).

Figure 5A:
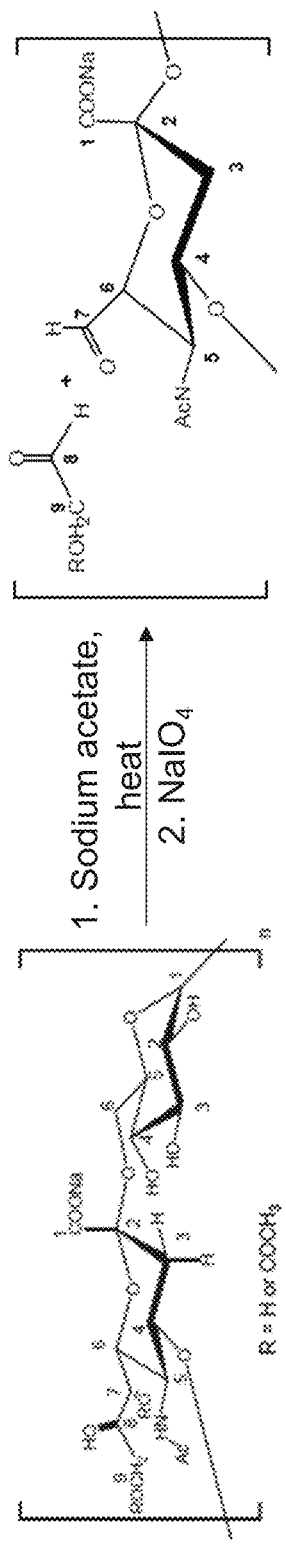

FIG. 5A illustrates depolymerization and activation of Serogroup Y Polysaccharide. The polysaccharide is depolymerized using, e.g., elevated temperature and then activated by treatment with sodium metaperiodate, which cleaves vicinal diols such as, for example, between carbon 7 and 8 of the sialic acid moiety and oxidizes them to aldehydes.

Figure 5B:

FIG. 5B illustrates formation of a Serogroup Y Polysaccharide-protein (e.g., TT) conjugate via reductive amination. A primary amine of the protein (PR) (e.g., lysine side chain or N-terminus) reacts with an aldehyde of a depolymerized, activated Serogroup Y Polysaccharide (PS) to form a Schiff base intermediate (not shown). The intermediate is reduced (e.g., using pyridine borane, picoline borane, or a cyanoborohydride) to give a secondary amine linkage. Individual protein molecules may react with more than one polysaccharide and vice versa (not shown; see illustration in FIG. 3). Unreacted aldehydes can be capped, i.e., reduced to alcohols, using a suitable reducing agent such as sodium borohydride after reduction of the Schiff base (not shown).

Figure 5C:
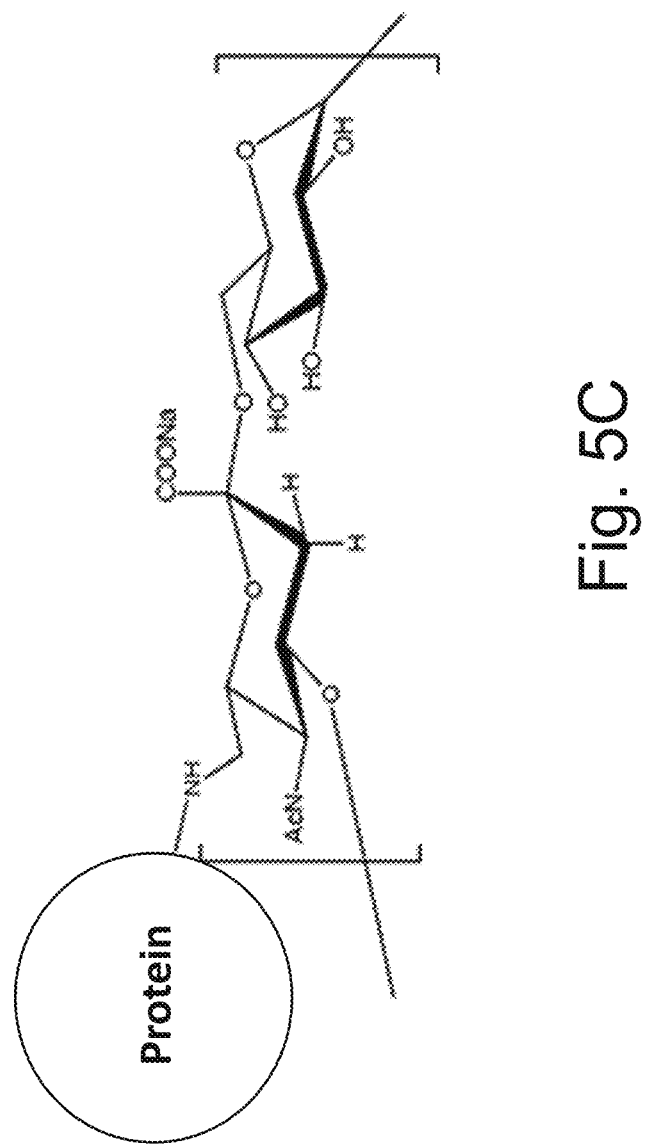

FIG. 5C shows a product of the reaction in FIG. 5B with one possible structure of the linked polysaccharide repeat unit drawn out. Linkage of the protein to additional polysaccharides or vice versa are possible (not shown; see illustration in FIG. 3).

Figure 6:
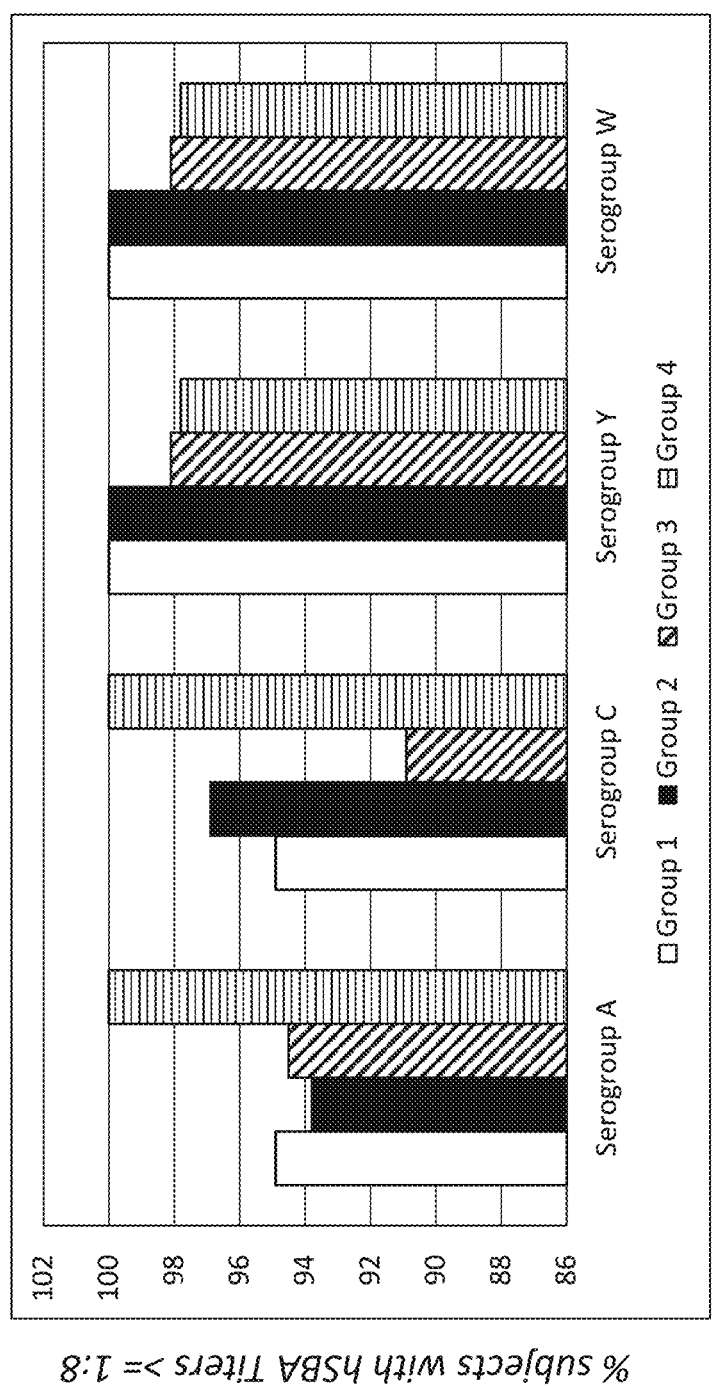

FIG. 6 shows the percentage of subjects in Groups 1-4 who achieved hSBA titers greater than or equal to 1:8 for serogroups A, C, Y, and W at 30 days (D30) after last vaccine administration.

Figure 7:
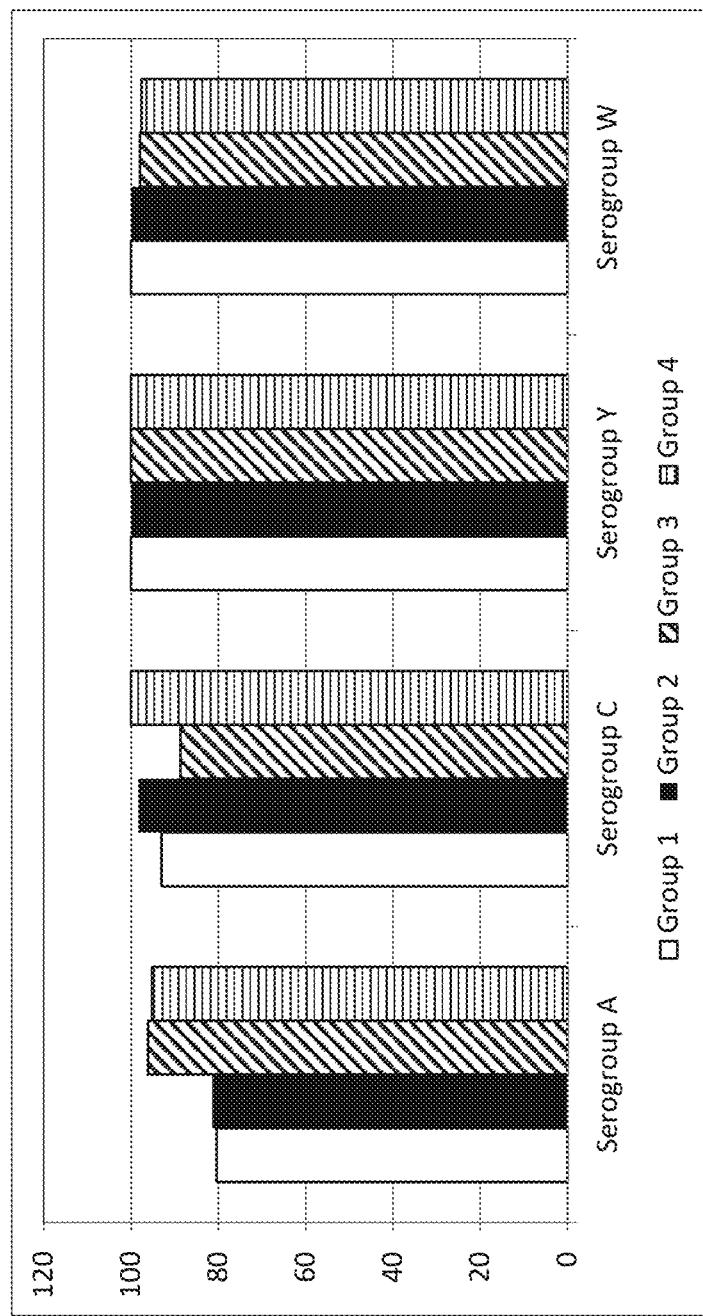

FIG. 7 shows the percentage of subjects in Groups 1-4 who achieved rSBA titers greater or equal to 1:8 for serogroups A, C, Y, and W at D30 after last vaccine administration.

Figure 8:
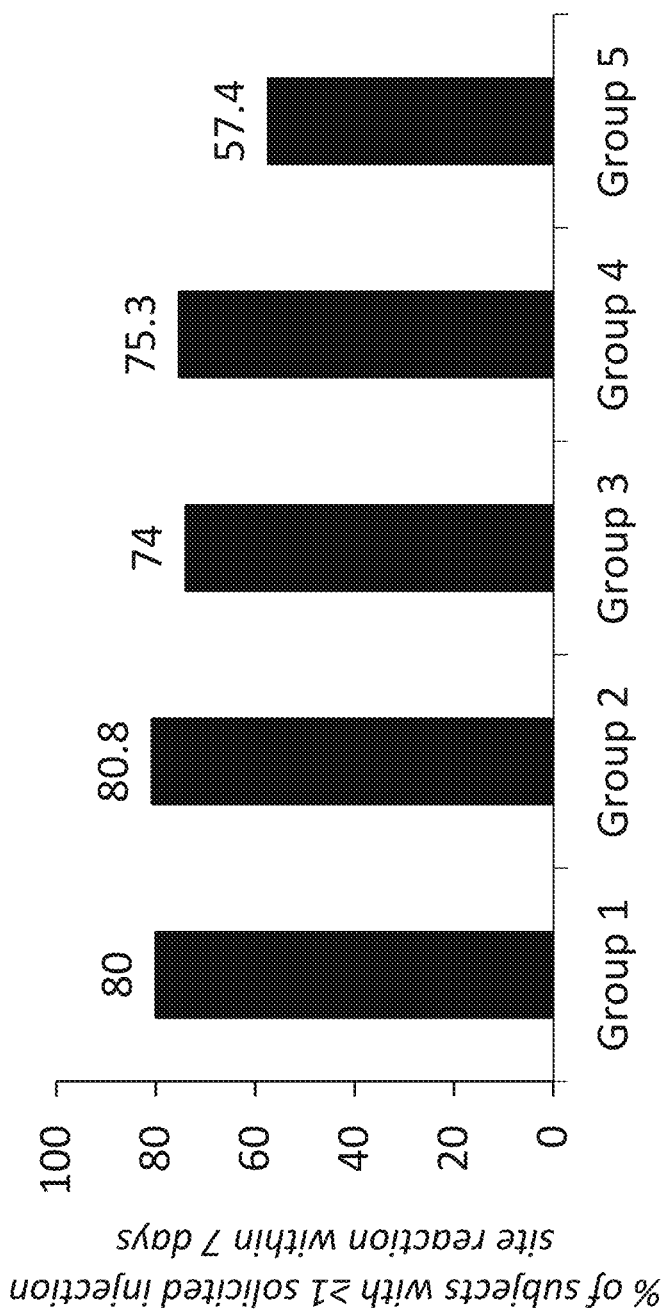

FIG. 8 shows the cumulative percentage of participants who reported one or more solicited injections site reaction within 7 days following administration of the MenACYW-TT vaccine.

Figure 9:
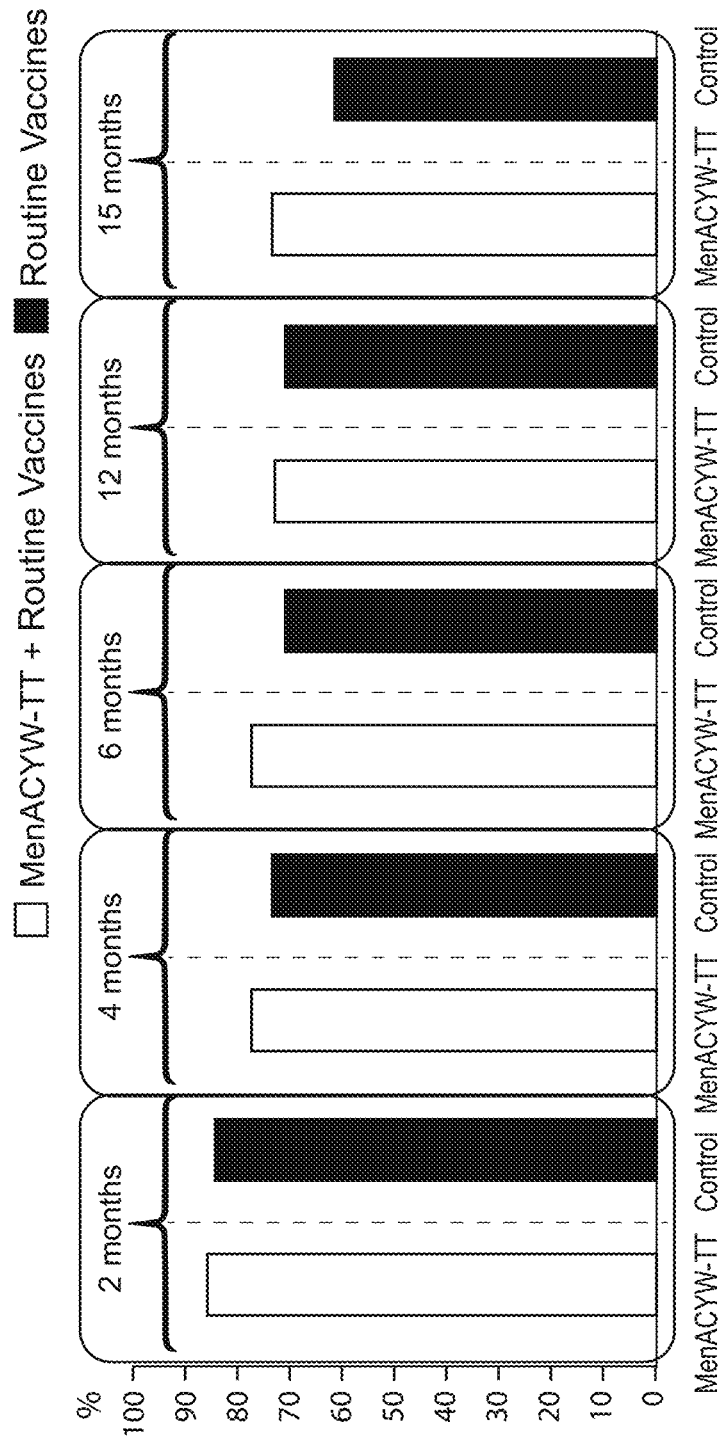

FIG. 9 shows the percentage of subjects with solicited systemic reactions within 7 days of administration of either MenACYW-TT vaccine plus routine vaccines or routine vaccines alone.

Figure 10:
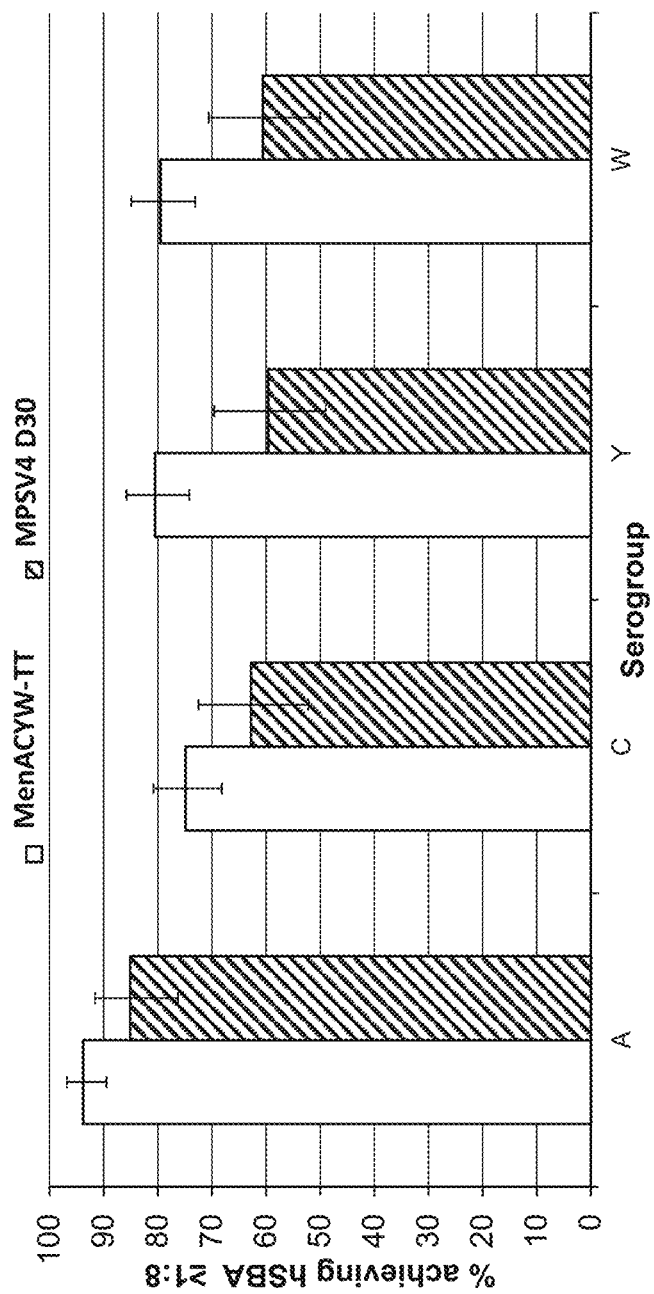

FIG. 10 shows the percentage of subjects achieving hSBA titers of ≥1:8 for different serogroups at D30 after administration of either MenACYW-TT or Menomune®-A/C/Y/W-135 (MPSV4) vaccine.

Figure 11:
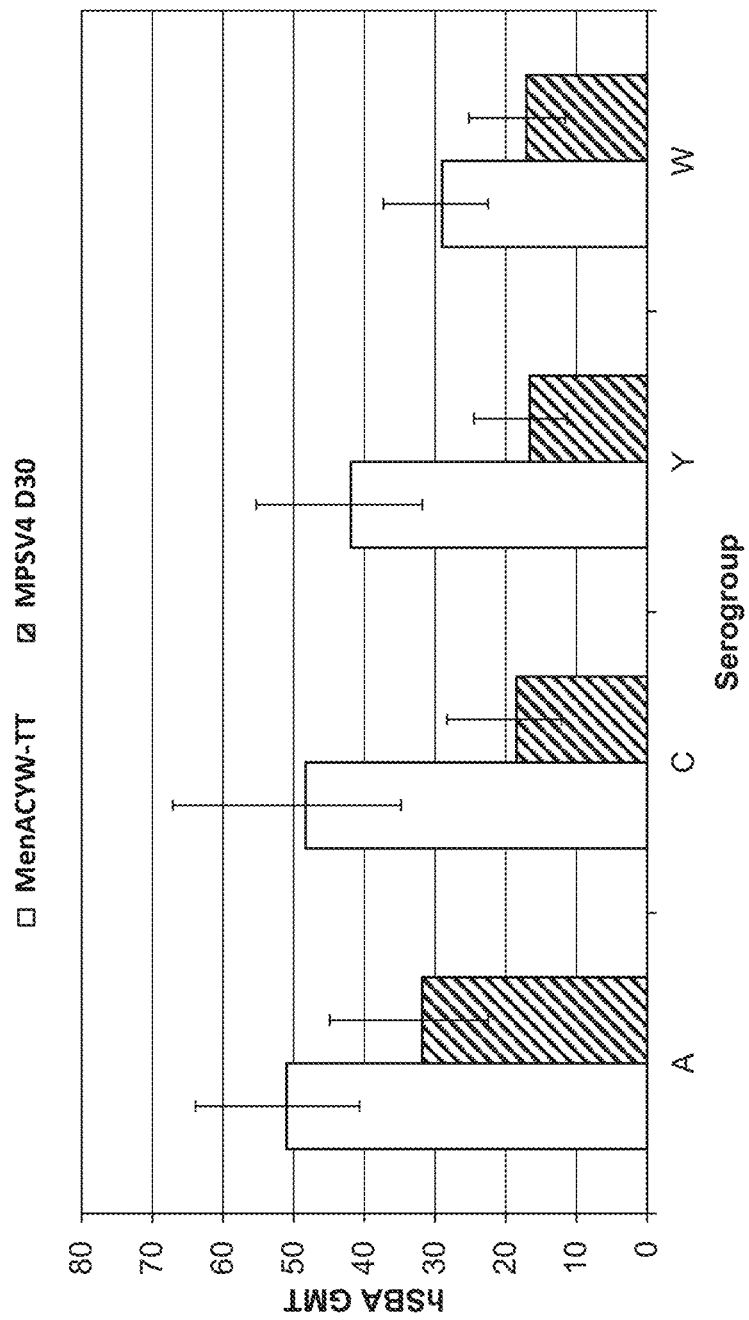

FIG. 11 shows a summary of hSBA geometric mean titers (GMTs) at D30 after administration of either MenACYW-TT or MPSV4 vaccine.

Figure 12:
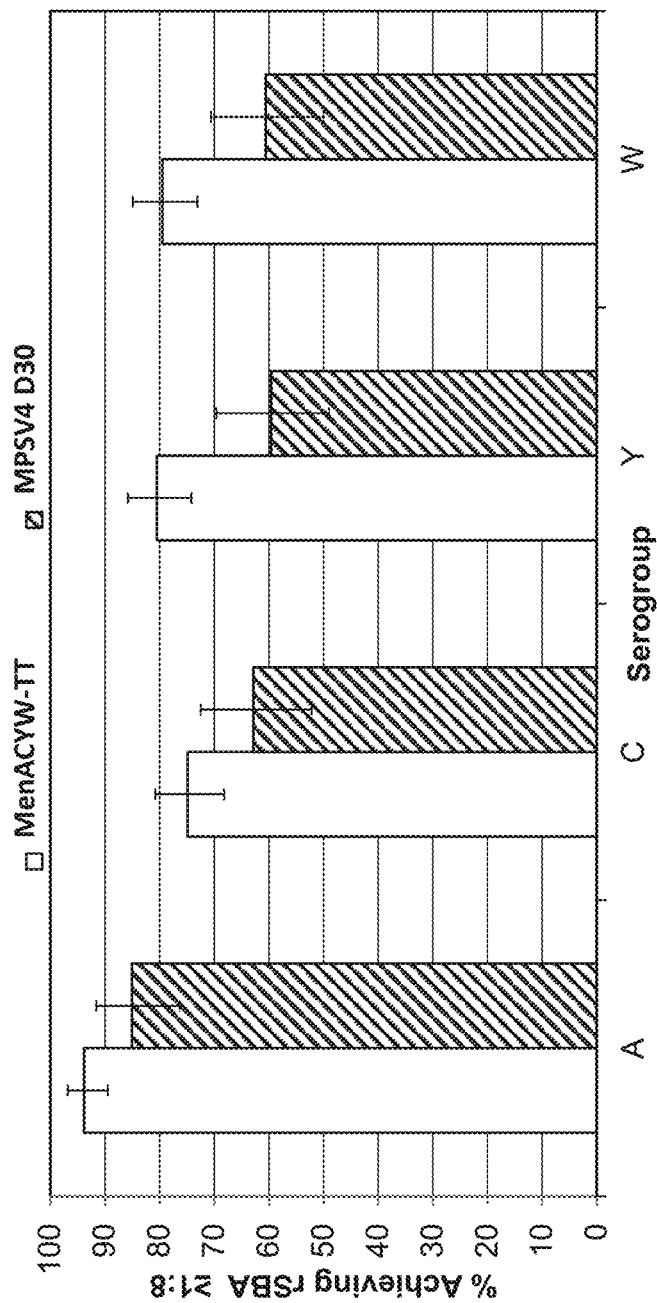

FIG. 12 shows the percentage of subjects achieving rSBA titers of ≥1:8 for different serogroups at D30 after administration of either MenACYW-TT or MPSV4 vaccine.

Figure 13:
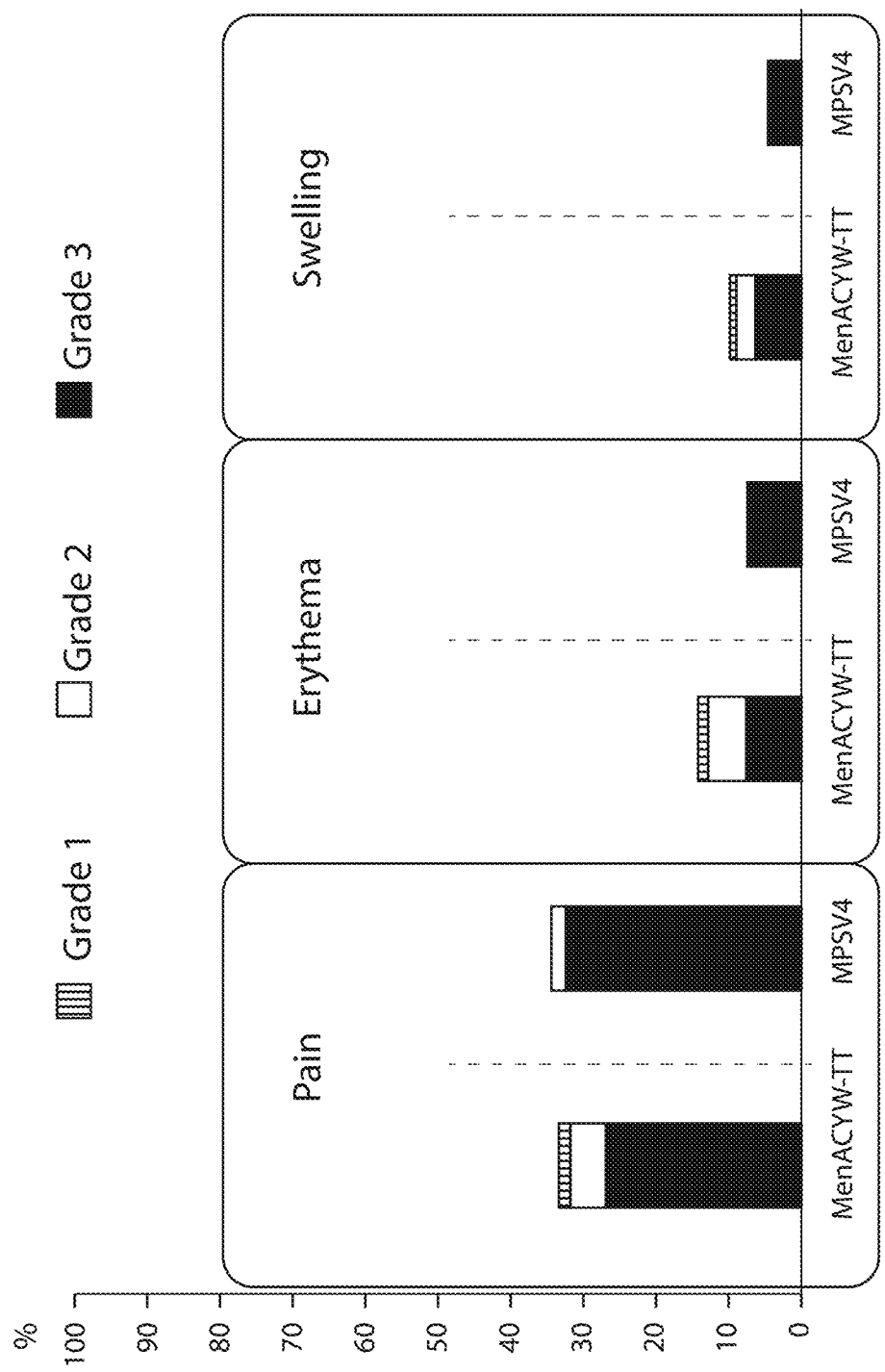

FIG. 13 shows the percentage of subjects with solicited injection site reactions by type and grade after administration of either MenACYW-TT or MPSV4 vaccine.

Figure 14:
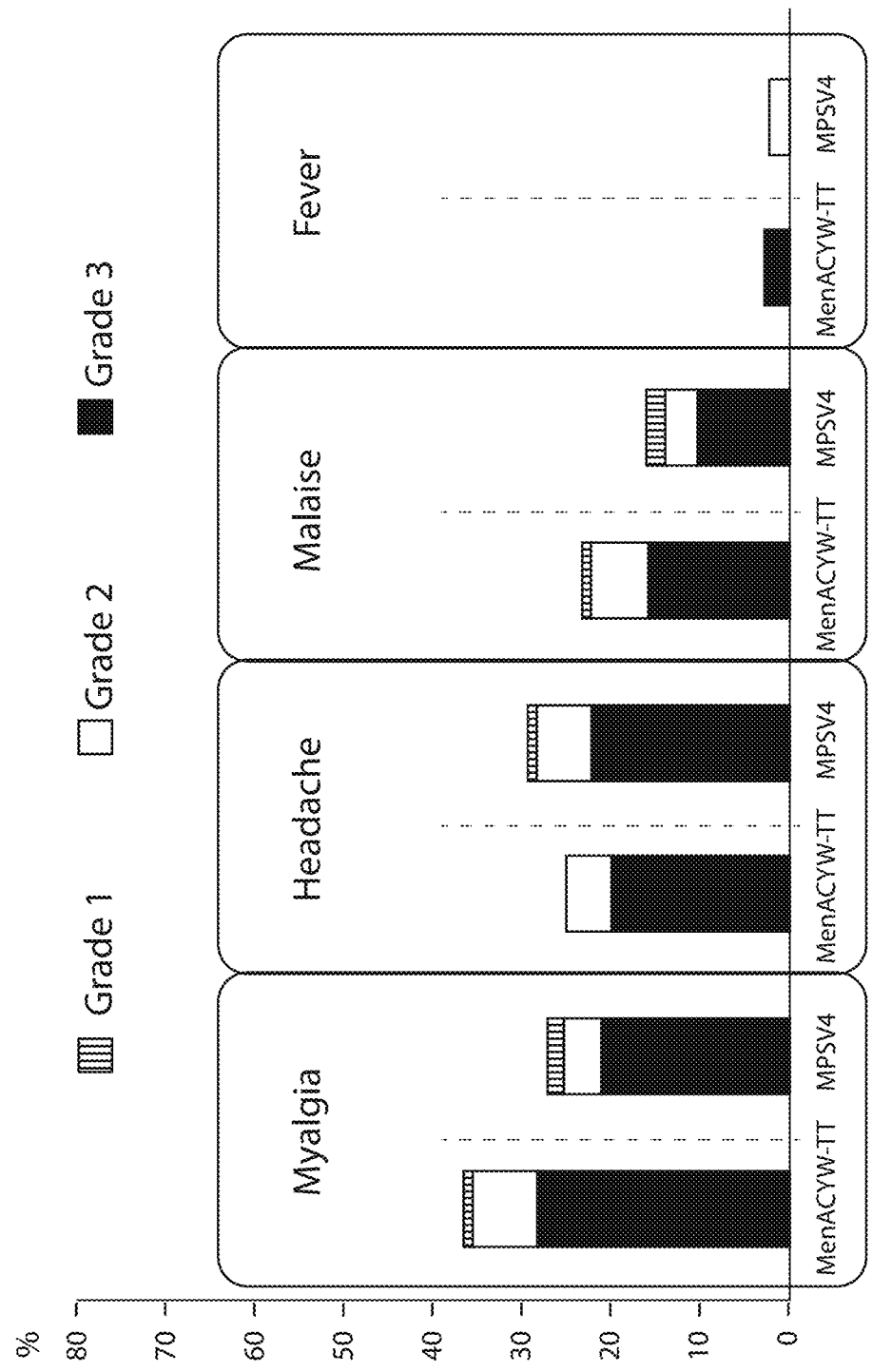

FIG. 14 shows the percentage of subjects with solicited systemic reactions by type and grade after administration of either the MenACYW-TT or MPSV4 vaccine.

Figure 15:
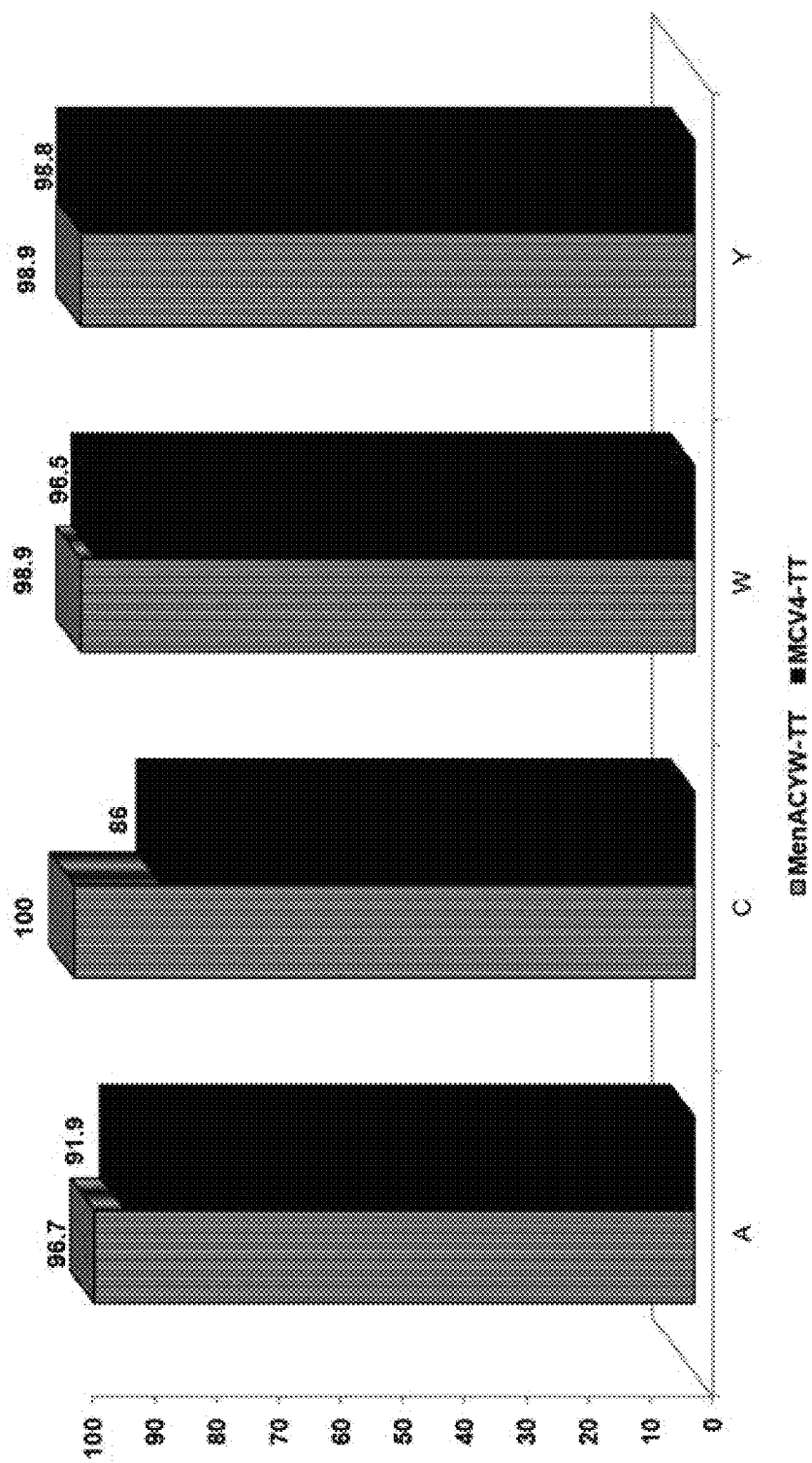

FIG. 15 shows the percentage of subjects achieving hSBA vaccine seroresponse at D30 after administration of either MenACYW-TT or MCV4-TT vaccine.

Figure 16:
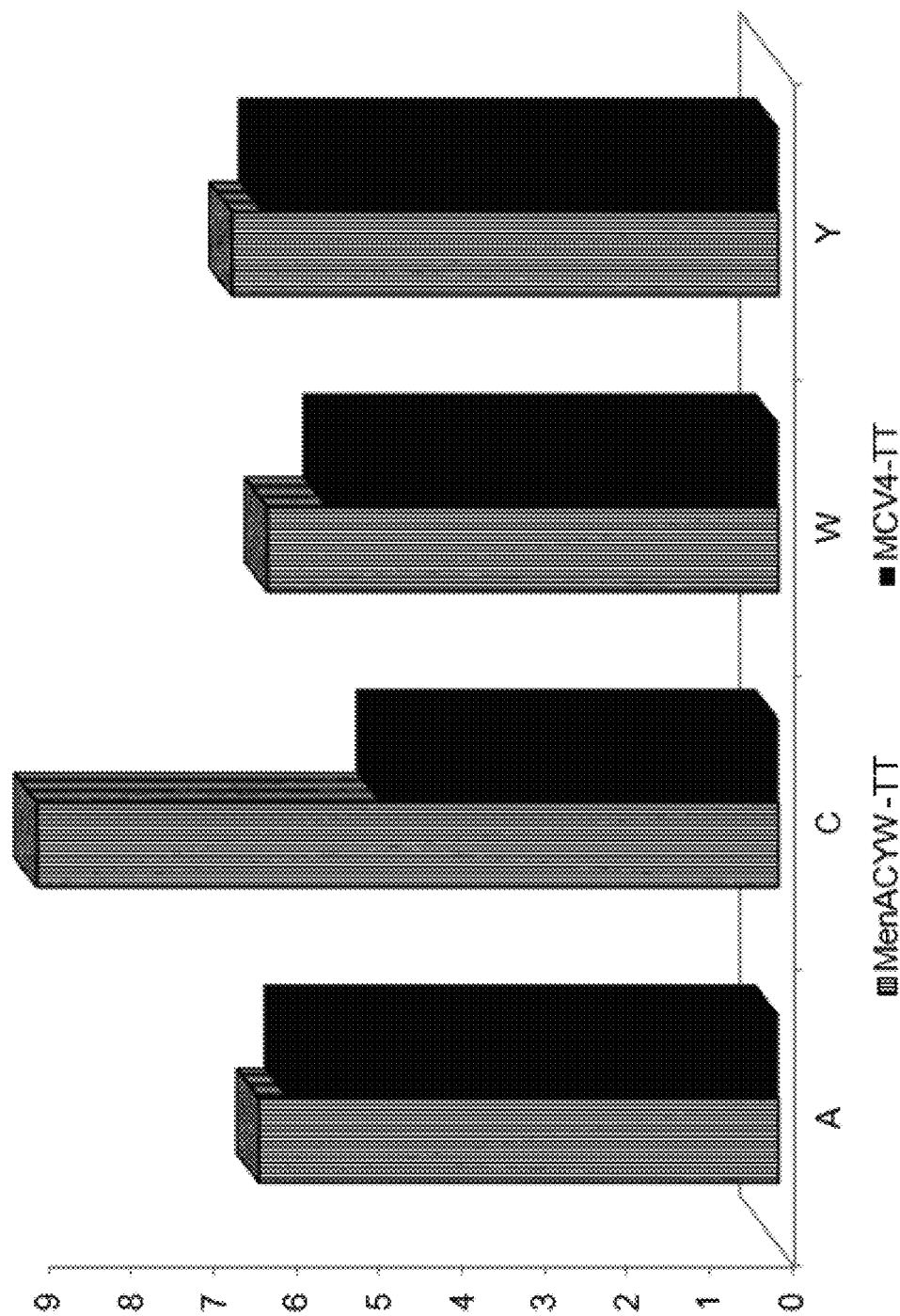

FIG. 16 shows post-vaccination hSBA geometric means after administration of either MenACYW-TT or MCV4-TT vaccine.

Figure 17:
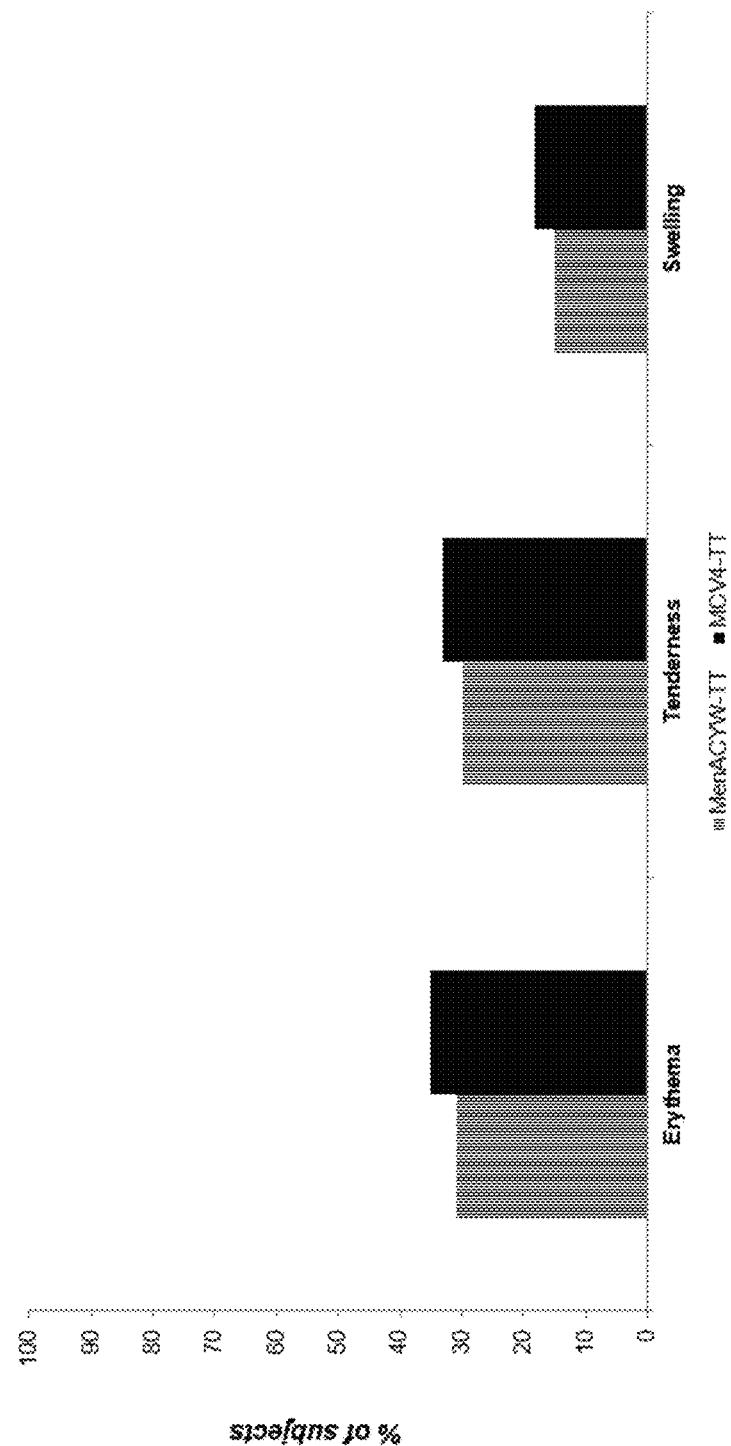

FIG. 17 shows solicited injection site reactions at D0-D7 following administration of either MenACYW-TT or MCV4-TT vaccine.

Figure 18:
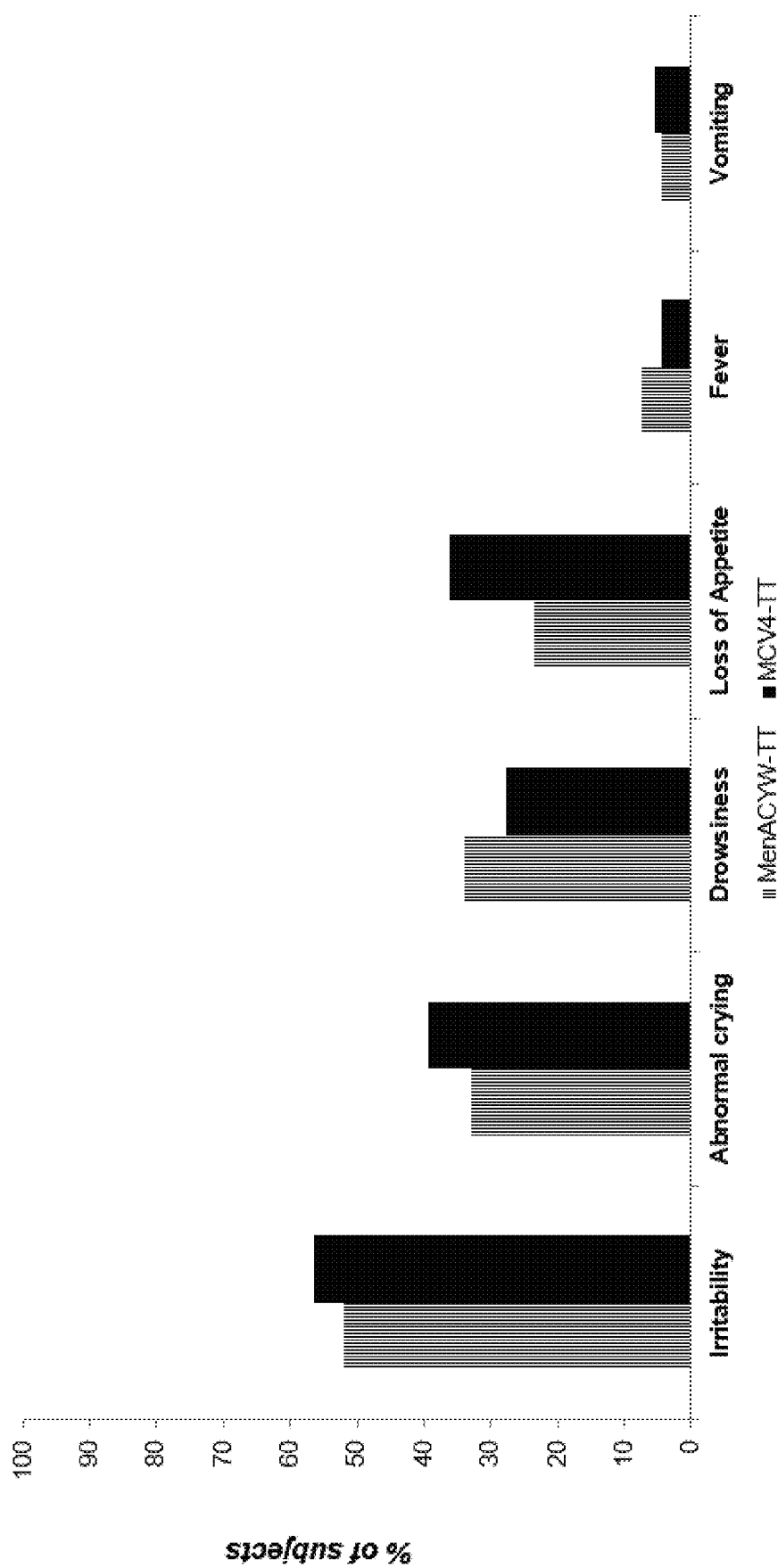

FIG. 18 shows solicited systemic reactions at D0-D7 following administration of either MenACYW-TT or MCV4-TT vaccine.

I. DETAILED DESCRIPTION OF EMBODIMENTS OF THE INVENTION

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a conjugate" includes a plurality of conjugates and reference to "a cell" includes a plurality of cells and the like.

Numeric ranges are inclusive of the numbers defining the range. Measured and measureable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The section headings used herein are for organizational purposes only and are not to be construed as limiting the desired subject matter in any way. In the event that any literature incorporated by reference contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

A. Definitions

Unless stated otherwise, the following terms and phrases as used herein are intended to have the following meanings:

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "kit" refers to a packaged set of related components, such as one or more compounds or compositions and one or more related materials such as solvents, solutions, buffers, instructions, or desiccants.

"Or" is used in the inclusive sense, i.e., equivalent to "and/or," unless the context requires otherwise.

The terms "linker" and "linkage" are used interchangeably and mean a chemical moiety comprising a chain of atoms that covalently attaches, or is attached to, items such as a carrier protein or a polysaccharide.

"Linking moiety" means a chemically reactive group, substituent or moiety, e.g. a nucleophile or electrophile, capable of reacting with another molecule to form a linkage by a covalent bond.

"Alkyl" means a saturated or unsaturated, branched, straight-chain, branched, or cyclic hydrocarbon radical derived by the removal of one hydrogen atom from a single carbon atom of a parent alkane, alkene, or alkyne. Typical alkyl groups consist of 1 to 12 saturated and/or unsaturated carbons, including, but not limited to, methyl, ethyl, propyl, butyl, and the like.

A "repeat unit" is the mono- or oligosaccharide residue that is polymerized in a polysaccharide. The repeat units of MenA and MenC are monosaccharides (N-acetyl mannosamine and sialic acid, respectively) and the repeat units of MenW-135 and MenY are disaccharides (of sialic acid and glucose for MenY, or sialic acid and galactose for MenW-135). Repeat units may vary from one to the next with respect to side chains (e.g., O-acetylation) and/or modifications such as those disclosed herein.

MenA, MenC, MenW-135, and MenY are used as shorthand for *Neisseria meningitidis* of serogroup A, C, W-135, or Y, respectively, or the capsular polysaccharide thereof (as in the case of, e.g., a "MenC conjugate" which means a conjugate of the capsular polysaccharide of *Neisseria meningitidis* of serogroup C to a carrier protein).

B. Exemplary Vaccine Compositions

In some embodiments, a vaccine composition is provided. In some embodiments, the vaccine composition comprises a conjugate of MenC capsular polysaccharide to a carrier protein. In some embodiments, the vaccine composition comprises a conjugate of MenA capsular polysaccharide to a carrier protein. In some embodiments, the vaccine composition comprises a conjugate of MenW-135 capsular polysaccharide to a carrier protein. In some embodiments, the vaccine composition comprises a conjugate of MenY capsular polysaccharide to a carrier protein. In some embodiments, the vaccine composition comprises at least two, at least three, or at least four conjugates of a capsular polysaccharide to a carrier protein. The at least two, at least three, or at least four conjugates of a capsular polysaccharide to a carrier protein can be conjugates of capsular polysaccharides from different serogroups of *Neisseria meningitidis*, for example, conjugates of MenA, MenC, MenY, and MenW capsular polysaccharides to a carrier protein, e.g., tetanus toxoid.

Capsular polysaccharides may be prepared according to the method described in US 2003/0068336 Example 1. Capsular polysaccharides may also be prepared using the medium and methods described in U.S. Pat. No. 6,933,137, for example.

Disclosed herein are conjugates comprising carrier proteins. Examples of protein carriers are discussed in, e.g., Pichichero M E. Protein carriers of conjugate vaccines: Characteristics, development, and clinical trials. Human Vaccines & Immunotherapeutics. 2013; 9(12):2505-2523. doi:10.4161/hv.26109, which is incorporated herein by reference. In some embodiments, the carrier protein comprises or consists of recombinant exoprotein alpha (REPA), diphtheria toxoid, CRM197, tetanus toxoid or a C-fragment of tetanus toxin. In some embodiments, the protein carrier is tetanus toxoid.

In some embodiments, the tetanus toxoid (I) is prepared by extraction, ammonium sulfate purification, and formalin inactivation of the toxin from cultures of *Clostridium tetani* (Harvard Strain) grown in a Mueller and Miller medium or a modified Mueller and Miller medium. In some embodiments, the TT is processed to reduce residual formaldehyde, is concentrated in sodium chloride and is filter sterilized. In some embodiments, the TT is purified by chromatography rather than ammonium sulfate purification. In some embodiments, the modified Mueller and Miller medium does not contain beef heart infusion. In some embodiments, the *Clostridium tetani* is grown in the medium described in WO2006/042542 at Table 3, page 16.

Certain embodiments discussed below involve a feature, such as a chemical moiety (e.g., a hydroxyl or O-acetylation) or a conjugation to a carrier protein, which is present in a given amount per unit mass of polysaccharide. For example, a certain feature or combination of features may be present at a level such as no less than 25 nmol/mg polysaccharide. This means that in 1 mg of polysaccharide, the feature or combination of features occurs at least $15\times10^{15}$ times (where 25 nmol=25×10 mole×($6.02\times10^{23}$ items/mole)=$15\times10^{15}$ items.

In some embodiments, the polysaccharides of the conjugate of MenC capsular polysaccharide to the carrier protein have an O-acetylation level ranging from 0.3 μmol/mg polysaccharide to 1.6 μmol/mg polysaccharide. In some embodiments, the level of O-acetylation is greater than or equal to 0.4, 0.5, 0.6, 0.7, 0.8, 0.9, 1.0, 1.1, or 1.2 mol/mg polysaccharide. In some embodiments, the level of O-acetylation is less than or equal to 0.7, 0.8, 0.9, 1.0, 1.1, 1.2, 1.3, 1.4, or 1.5 μmol/mg polysaccharide. E.g., the level can range from 0.6 to 1.5 μmol/mg polysaccharide or 0.8 to 1.4 μmol/mg polysaccharide. O-acetyl content can be measured by the Hestrin method (Hestrin et. al., J. Biol. Chem. 1949, 180, p. 249).

In some embodiments, at least one of the conjugates in the composition has a weight-average molecular weight ranging from 300 kDa to 1500 kDa. In some such embodiments, the weight-average molecular weight is greater than or equal to 400 kDa, 500 kDa, 600 kDa, 700 kDa, 800 kDa, 900 kDa, 1000 kDa, or 1100 kDa. In some such embodiments, the weight-average molecular weight is less than or equal to 600 kDa, 700 kDa, 800 kDa, 900 kDa, 1000 kDa, 1100 kDa, 1200 kDa, 1300 kDa, or 1400 kDa. Weight-average molecular weight can be determined by methods known in the art, e.g., multi-angle light scattering (MALS). In some embodiments, at least one conjugate in the composition comprises (i.e., is a population of molecules comprising) molecules having a molecular weight in the range of 700 kDa to 1400 kDa. It should be noted that some molecules of the population can have a weight in the range regardless of whether the weight-average or number-average molecular weight is in the range or not. For example, a population of molecules with a weight-average molecular weight of 600 kDa or 1500 kDa will likely contain molecules having a molecular weight in the range of 700 kDa to 1400 kDa. In some embodiments, at least one conjugate in the composition comprises molecules having a molecular weight in the range of 800 kDa to 1300 kDa. In some embodiments, at least one conjugate in the composition comprises molecules having a molecular weight in the range of 700-800, 800-900, 900-1000, 1000-1100, 1100-1200, 1200-1300, 1300-1400, or 1400-1500 kDa. In some embodiments, a MenA conjugate has a molecular weight as described above. In some embodiments, a MenC conjugate has a molecular weight as described above. In some embodiments, a MenW-135 conjugate has a molecular weight as described above. In some embodiments, a MenY conjugate has a molecular weight as described above. In some embodiments, a molecular weight is determined using multi-angle light scattering (MALS). In some embodiments, a molecular weight is determined using high-performance size-exclusion chromatography (HPSEC).

In some embodiments, a conjugate, such as a conjugate of MenC, is a population comprising single-end-linked conjugated polysaccharides, double-end-linked polysaccharides, or a combination thereof. A single-end-linked conjugated polysaccharide is attached at one end to a carrier protein. A double-end-linked conjugated polysaccharide is attached at both ends to a carrier protein. End-linked conjugated polysaccharides can be formed, e.g., by cleaving and activating vicinal diols in the polysaccharide backbone to expose activated ends, such as by periodate treatment. For example, the MenC polysaccharide has a 7,8 vicinal diol in its sialic acid repeat unit to the extent that the 7 and 8 positions are not O-acetylated in the same repeat unit. This vicinal diol is in the backbone of the polysaccharide because cleaving it separates one saccharide from the next, i.e., the vicinal diol is not part of a side chain. Following activation, the activated ends can then react with a carrier protein (or to a linker which will then be or is already attached to a carrier protein), to form an end-linked polysaccharide conjugate. A conjugate is single-end linked if only one of the ends (terminal saccharide residues) of the polysaccharide is linked to a carrier protein (including through a linker if applicable). A double-end-linked conjugate has carrier proteins linked to both ends of the polysaccharide. In general, using a higher stoichiometry of polysaccharide relative to carrier protein or a lower overall reactant concentration will bias a conjugation reaction toward single-end-linked products. In contrast, a lower stoichiometry of polysaccharide relative to carrier protein or a higher overall reactant concentration will bias a conjugation reaction toward double-end-linked products.

In some embodiments, the single-end-linked conjugated polysaccharides (e.g., MenC conjugates) have a terminal unlinked saccharide in which there is a primary hydroxyl at the 7 position, or wherein the reducing end is modified with a (2-hydroxy)ethoxy. This can result from activation of a polysaccharide comprising 7,8 vicinal diols with periodate (which gives terminal aldehydes), conjugation at one end, and reduction of the unreacted aldehyde at the other end, e.g., with a borohydride reagent. The primary hydroxyl at the 7 position can be considered the end of a truncated sialic acid residue. The reducing end that is modified with a (2-hydroxy)ethoxy can be considered a sialic acid residue attached at its reducing end to a fragment of the 9 and 8 carbons of another residue and their associated oxygens.

In some embodiments, the conjugate is a MenW-135 and/or MenY polysaccharide that comprises one or more modifications chosen from (i) a primary hydroxyl at a position of a vicinal diol in a native MenW-135 or MenY polysaccharide and (ii) a conjugation to the carrier protein, wherein the modifications are present at no less than 60 nmol/mg polysaccharide. The modifications can be formed by periodate oxidation followed by conjugation to the carrier protein and reduction of unreacted aldehydes. Periodate-driven cleavage of the saccharide residues can occur at vicinal diol positions such as the 7,8 or 8,9 positions of the sialic acid and also potentially in the hexose ring of the repeat unit, particularly where the diols are in a cis arrangement. In some embodiments, the modifications are present in an amount less than 200 nmol/mg polysaccharide, less than 150 nmol/mg polysaccharide, less than 100 nmol/mg polysaccharide, or less than 80 nmol/mg polysaccharide.

In some embodiments, a polysaccharide is linked to a carrier protein through a secondary amine. In some embodiments, a polysaccharide is attached to the carrier protein as shown in formula II:

$$PR—NH—CH_2—PS \quad (II)$$

wherein PS indicates attachment to the polysaccharide and PR indicates attachment to the carrier protein. Such a secondary amine linkage can be formed, for example, through reductive amination in which a primary amine on a protein (e.g., N-terminus or amino group of a lysine side chain) attacks an activated group (e.g., aldehyde) on a polysaccharide, forming a Schiff base which is then reduced to form the secondary amine. Reduction can be performed using a suitable reducing reagent such as a cyanoborohydride (e.g., sodium cyanoborohydride) or a borane (e.g., pyridine borane or picoline borane).

In some embodiments, a conjugate of a MenC polysaccharide is reduced in size by 3x-8x relative to native MenC polysaccharide, e.g., 3x-4x, 4x-5x, 5x-6x, 6x-7x, or 7x-8x. Periodate cleavage separates adjacent repeat units and thus provides for reduction in size of the polysaccharide. Size may be further reduced by a treatment such as heat and/or acid, e.g., before the periodate treatment. Other known treatments for reducing size may also be used, such as sonication or microfludization.

In some embodiments, a conjugate of a MenA polysaccharide has a polysaccharide to carrier protein mass ratio of 0.3 to 1.5, e.g., 0.3 to 0.4, 0.4 to 0.5, 0.5 to 0.6, 0.6 to 0.7, 0.7 to 0.8, 0.8 to 0.9, 0.9 to 1.0, 1.0 to 1.1, 1.1 to 1.2, 1.2 to 1.3, 1.3 to 1.4, or 1.4 to 1.5. In some embodiments, a conjugate of a MenA polysaccharide has a polysaccharide to carrier protein mass ratio of 0.5 to 1.5.

In some embodiments, a conjugate of a MenC polysaccharide has a polysaccharide to carrier protein mass ratio of 0.3 to 1.1, e.g., 0.3 to 0.4, 0.4 to 0.5, 0.5 to 0.6, 0.6 to 0.7, 0.7 to 0.8, 0.8 to 0.9, 0.9 to 1.0, or 1.0 to 1.1.

In some embodiments, a conjugate of a MenW-135 polysaccharide has a polysaccharide to carrier protein mass ratio of 0.3 to 1.3, e.g., 0.3 to 0.4, 0.4 to 0.5, 0.5 to 0.6, 0.6 to 0.7, 0.7 to 0.8, 0.8 to 0.9, 0.9 to 1.0, 1.0 to 1.1, 1.1 to 1.2, or 1.2 to 1.3.

In some embodiments, a conjugate of a MenY polysaccharide has a polysaccharide to carrier protein mass ratio of 0.5 to 1.3, e.g., 0.3 to 0.4, 0.4 to 0.5, 0.5 to 0.6, 0.6 to 0.7, 0.7 to 0.8, 0.8 to 0.9, 0.9 to 1.0, 1.0 to 1.1, 1.1 to 1.2, or 1.2 to 1.3.

In some embodiments, a vaccine composition provided herein comprises less than 20% free polysaccharide by weight, e.g., comprises less than 10% free polysaccharide by weight, less than 5% free polysaccharide by weight, or substantially lacks free polysaccharide. "Substantially lacks free polysaccharide" means that the level of free polysaccharide is below the detection limit of a deoxycholate precipitation assay in which protein-conjugated polysaccharide is precipitated with deoxycholate and polysaccharide remaining in solution is assayed, e.g., as described in Lei et al., "Quantification of free polysaccharide in meningococcal polysaccharide-diphtheria toxoid conjugate vaccines," Dev Biol (Basel). 2000; 103:259-64 (PMID: 11214246).

In some embodiments, a polysaccharide is attached to the carrier protein through a linker comprising 2-10 linear carbons, e.g., 2, 3, 4, 5, 6, 7, 8, 9, or 10 carbons. "Linear carbons" are carbons along the chain leading from the polysaccharide to the carrier protein and do not include carbons on a branch from this chain. In some embodiments, the linker comprises a spacer between a first carbonyl and a second carbonyl, and the spacer comprises 4-8 carbons (e.g., 4, 5, 6, 7, or 8 carbons), which may be linear carbons. The first carbonyl can be part of a carbamate. The second carbonyl can be part of an amide. The first carbonyl can be proximal to the polysaccharide and distal to the carrier protein. The second carbonyl can be proximal to the carrier protein and distal to the polysaccharide. The linker can comprise a residue of a dihydrazide, such as adipic acid dihydrazide (ADH). In some embodiments, the polysaccharide is attached to the carrier protein through a linker of formula I:

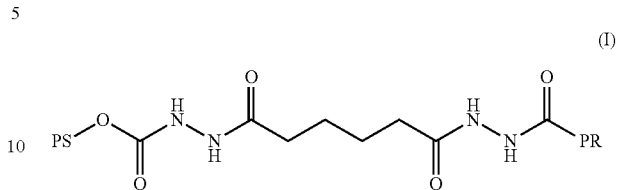

wherein PS indicates attachment to the polysaccharide and PR indicates attachment to the carrier protein. An individual polysaccharide can be attached to one or more than one carrier protein (at different positions), and vice versa.

In some embodiments, a linker is present in a conjugate at a ratio of one linker per 10-100 saccharide repeat units, e.g., 20-60. This includes linkers to which both a carrier protein and a polysaccharide are attached and also linkers attached only to the polysaccharide, i.e., which did not form an attachment to a carrier protein.

In some embodiments, a conjugate of a *Neisseria meningitidis* capsular polysaccharide to a carrier protein through a linker is provided in which the linker is present in an amount of 1 linker per 10-100 repeat units of the polysaccharide, e.g., 1 linker per 10-20 repeat units, 1 linker per 20-30 repeat units, 1 linker per 30-40 repeat units, 1 linker per 40-50 repeat units, 1 linker per 50-60 repeat units, or 1 linker per 60-70 repeat units. In some embodiments, a MenA polysaccharide is attached to the carrier protein through a linker as described above. In some embodiments, a MenC polysaccharide is attached to the carrier protein through a linker as described above.

In some embodiments, a polysaccharide conjugate composition according to the disclosure has improved stability relative to existing formulations. In some embodiments, stability is tested in terms of whether the free polysaccharide levels corresponding to each conjugated polysaccharide remain below 40% after a period of storage at 2° C.-8° C., e.g., 2.5, 3, 3.5, 4, or 4.5 years. In some embodiments, stability is tested in terms of whether the free polysaccharide levels corresponding to each conjugated polysaccharide remain below 40% after a period of storage at 23° C.-27° C., e.g., 2, 3, 4, 5, or 6 months. Certain quadrivalent MenA-CYW polysaccharide conjugate vaccines require lyophilization or other preservative measures at least in part as a result of low stability as liquid formulations with respect to one or more of the constituent conjugates. Lyophilization complicates both manufacturing and administration relative to a single liquid formulation. In some embodiments, a polysaccharide is attached to the carrier protein at multiple points. Multiple point attachment is generally a consequence of conjugation chemistry, e.g., periodate activation followed by reductive amination, or carbonyl diimidazole-based coupling (optionally with a linker) that can form a lattice of carrier protein and polysaccharide, together with appropriate polysaccharide size and loading ratio. For detailed discussion of such exemplary chemistry, see the Examples below. Exemplary polysaccharide sizes and loading ratios compatible with formation of a protein-polysaccharide lattice involving multiple points of attachment are at least 30 kDa (and exemplary size ranges discussed above) and polysaccharide/protein ratios of 0.3 to 1.5 (and exemplary loading ratio ranges discussed above). Without wishing to be bound by a particular theory, providing conjugates with multiple points of attachment between the polysaccharide and carrier protein may contribute to long-term stability of the conjugate in that multiple cleavage (e.g., hydrolytic) events would be needed to liberate polysaccharide fragments from the carrier protein. This contribution to long-term stability may be especially relevant to the MenA polysaccharide, which has phosphodiester linkages that may be more labile during storage in liquid than glycosidic bonds. In some embodiments, a composition comprises a MenA polysaccharide with multiple points of attachment to the carrier protein. In some embodiments, a composition comprises a MenC polysaccharide with multiple points of attachment to the carrier protein. In some embodiments, a composition comprises a MenY polysaccharide with multiple points of attachment to the carrier protein. In some embodiments, a composition comprises a MenW-135 polysaccharide with multiple points of attachment to the carrier protein. In some embodiments, a composition comprises MenA, MenC, MenY, and MenW-135 polysaccharides wherein each have multiple points of attachment to the carrier protein.

In some embodiments, a vaccine composition described herein is provided as a liquid formulation in a syringe, e.g., a pre-filled and/or silicone-free syringe. In some embodiments, such a syringe is commercially packaged for sale and/or distribution.

C. Exemplary Methods of Producing Conjugates and Vaccines

Provided herein are methods for producing and/or purifying conjugates of a capsular polysaccharide to a carrier protein.

A reagent (such as an activating agent) is considered to be present in a given amount in a step (e.g., an activating step) if it is present in such amount at any time during the relevant step or reaction (e.g., when the reaction is started).

In some embodiments, a method of producing a conjugate of a polysaccharide to a carrier protein is provided. In some embodiments, a polysaccharide is de-O-acetylated, e.g., by alkaline hydrolysis. For example, a hydroxide such as NaOH or KOH can be used, e.g., at a concentration of between 50-150, 60-140, 70-130, 80-120, 90-110, or 95-100 mM. In some embodiments, the hydroxide is at a concentration of 50, 60, 70, 80, 90, or 100 mM. In some embodiments, the hydroxide is at a concentration of 100 mM. The de-O-acetylation can be performed at a time and temperature sufficient to de-O-acetylate the polysaccharide by 40% to 70%, or 50% to 60% compared to the starting amount. In some embodiments, the de-O-acetylation can be performed at a time and temperature sufficient to de-O-acetylate the polysaccharide by 30, 40, 50, 60, 70, 80, 90, or 100% as compared to the starting amount. In certain embodiments, following de-O-acetylation, the polysaccharide has a degree of O-acetylation from 0.6 µmol/mg polysaccharide to 1.5 µmol/mg polysaccharide or 0.8 to 1.4 µmol/mg polysaccharide. In some embodiments, the degree of O-acetylation is greater than or equal to 0.5, 0.6, 0.7, 0.8, 0.9, 1.0, 1.1, 1.2, 1.3, 1.4, 1.5, 1.6, 1.7, 1.8, 1.9, or 2.0 µmol/mg polysaccharide.

In some embodiments, the degree of O-acetylation is less than or equal to 0.8, 0.9, 1.0, 1.1, 1.2, 1.3, or 1.4 µmol/mg polysaccharide.

In some embodiments, a polysaccharide is depolymerized, e.g., by heat, acid treatment, sonication, microfluidization, or a combination thereof, such as heat and acid. E.g., the polysaccharide can be heated to 40° C.-80° C. (e.g., 45° C., 50, 55, 60, 65, 70, or 75) and/or exposed to a mildly acidic pH such as 5, 5.5, 6, or 6.5 or higher. The polysaccharide can be depolymerized down to a weight-average molecular weight, e.g., of 50 kDa to 200 kDa, such as 50, 75, 100, 125, 150, 175 or 200.

Some methods use an activating agent that can form a carbamate linkage, examples of which are known in the art. An activating agent that can form a carbamate linkage can be a compound having a carbonyl attached to two good leaving groups, such as N-linked heteroaryls, such as imidazole, pyridine, pyrimidine, purine, triazine, pyrazine, thiazine, thiazole, etc. In some embodiments, the activating agent is carbonyl diimidazole. The activating agent can be present in a molar excess over the polysaccharide by 20-fold to 50-fold, e.g., 20-fold to 25-fold, 25-fold to 30-fold, 30-fold to 35-fold, 35-fold to 40-fold, 40-fold to 45-fold, or 45-fold to 50-fold.

In some embodiments, a linker such as a dihydrazide linker is reacted with an activated polysaccharide, e.g., in a mole ratio of 0.3 to 1.0 relative to polysaccharide repeat units, such as 0.3 to 0.4, 0.4 to 0.5, 0.5 to 0.6, 0.6 to 0.7, 0.7 to 0.8, 0.8 to 0.9, or 0.9 to 1.0. In some embodiments, the dihydrazide linker is adipic acid dihydrazide. In some embodiments, the polysaccharide is derivatized with the linker such that it contains one linker per 10-100 repeat units, e.g., one linker per 10-20, 20-30, 30-40, 40-50, 50-60, 60-70, 70-80, 80-90, or 90-100 repeat units. In some embodiments, the polysaccharide is derivatized with the linker such that it contains one linker per 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 repeat units.

In some embodiments, a polysaccharide is activated by treatment with an oxidizer, such as a periodate, e.g., sodium metaperiodate (also known as sodium periodate). In some embodiments, the oxidizer reacts with the polysaccharide to form aldehydes. In some embodiments, the aldehydes are formed on side chains of the polysaccharide, e.g., for MenW-135 and MenY polysaccharides. In some embodiments, the aldehydes are formed by cleaving the polysaccharide backbone and are formed at termini, e.g., for MenC polysaccharides. The oxidizing treatment can be performed using the oxidizer at around 2 mM, e.g., 1.5 to 3 mM. The oxidizing treatment can be performed at 1.5, 1.6, 1.7, 1.8, 1.9, 2.0, 2.1, 2.2, 2.3, 2.4, 2.5, 2.6, 2.7, 2.8, 2.9, or 3.0 mM. The oxidizing treatment can be performed at a temperature and time sufficient to produce at least 20 nmol/mg polysaccharide, e.g., 20-30, 20-40, 20-50, 20-60, 20-70, 20-80, 20-90, 20-100, 20-150, 20-160, 20-170, 20-180, 20-190, or 20-200 nmol/mg. The oxidizing treatment can be performed at a temperature and time sufficient to produce at least 20, 30, 40, 50, 60, 70, 80, 90, 100, 110, 120, 130, 140, 150, 160, 170, 180, 190, or 200 nmol/mg polysaccharide. In some embodiments, the oxidizing treatment is at a pH ranging from 6.5 to 9.5, or has a pH of 6.0, 6.5, 7.0, 7.5, 8.0, 8.5, 9.0, or 9.5. In some embodiments, the oxidizing treatment is performed in a liquid solution below room temperature, e.g., less than 20° C., 15° C., 10° C., or 5° C.

Where conjugation is via reductive amination, Schiff bases can be reduced with a suitable reducing agent such as a cyanoborohydride (e.g., $NaCNBH_3$) or a borane such as pyridine borane or picoline borane.

Following conjugation, where unreacted aldehydes are present, the conjugate can be stabilized by reducing or aminating the aldehydes. A borohydride such as $NABH_4$ is a suitable reducing reagent. Ammonia, methylamine, glycine, alanine, and the like are suitable for aminating the unreacted aldehydes.

In some embodiments, the conjugation is purified. One method for purification, involving ultrafiltration in the presence of ammonium sulfate, is described in U.S. Pat. No. 6,146,902. Alternatively, conjugates can be purified away from unreacted protein and polysaccharide by any number of standard techniques including, inter alia, size exclusion chromatography, density gradient centrifugation, hydrophobic interaction chromatography, mixed mode resin chromatography, or ammonium sulfate fractionation. See, e.g., P. W. Anderson, et. al. (1986). J. Immunol. 137: 1181-1186. See also H. J. Jennings and C. Lugowski (1981) J. Immunol. 127: 1011-1018.

In some embodiments, hydrophobic interaction chromatography (HIC) is performed. A resin such as a phenyl, hexyl, heptyl, octyl, nonyl, or decyl resin can be used. A mixture can be loaded on the resin to purify conjugate away from free polysaccharide. In some embodiments, the mixture comprises a salt, such as ammonium sulfate. In some embodiments, the pH of the mixture being loaded is adjusted to bring the pH closer to neutral. In some embodiments, the pH of the mixture being loaded is or is adjusted to 5.5-8.5, 6-8, 6.5 to 7.5, or 7. The salt can be present at a concentration of, e.g., 0.5 M to 1.5 M, such as 0.5 M to 0.7 M, 0.7 M to 0.9 M, 0.9 M to 1.1 M, 1.1 M to 1.3 M, or 1.3 M to 1.5 M. After loading the resin can be washed with a salt solution, e.g., comprising ammonium sulfate, in which the salt concentration can be, e.g., as indicated in the previous sentence. In some embodiments, the resin is in a column and the wash is at least two, three, four, five, or six column volumes, e.g., up to 7, 8, 9, or 10 column volumes. In some embodiments, the resin is washed in batches of a salt solution, e.g., two or more batches with the cumulative volume of the batches having a volume at least 2, 3, 4, 5, 6, or 7 times the volume of the mixture prior to loading. The conjugate can interact more strongly with the resin, e.g., at high ionic strength, and the free polysaccharide can be washed out. The conjugate can be eluted from the resin following washing using a low ionic strength eluent, such as water, e.g., WFI. Alternatively, a low salt solution can be used, e.g., having a salt concentration (e.g., an acetate salt, such as sodium acetate) of less than or equal to 0.2, 0.1, 0.05, 0.02, 0.01, or 0.005 M. In some embodiments, the eluate comprises less than 20% free polysaccharide by weight, e.g., comprises less than 10% free polysaccharide by weight, less than 5% free polysaccharide by weight, or substantially lacks free polysaccharide.

In some embodiments, a method of producing a conjugate of a *Neisseria meningitidis* capsular polysaccharide to a carrier protein comprises
a) activating the polysaccharide with an activating agent that can form a carbamate linkage (e.g., carbonyl diimidazole) wherein the activating agent is present in a molar excess over the polysaccharide of 20-fold to 50-fold;
b) quenching the activating agent (e.g., using water) and derivatizing the activated polysaccharide with a dihydrazide linker added at a mole ratio of 0.3 to 1.0 relative to polysaccharide repeat units, wherein the polysaccharide is derivatized at a ratio of one dihydrazide linker per 10-100 saccharide repeat units;
c) conjugating the derivatized polysaccharide to the carrier protein by carbodiimide chemistry, wherein the polysaccharide is present at the beginning of the conjugation reaction at a weight-to-weight ratio of 3:1 to 5:1 relative to the carrier protein, thereby forming the conjugate.

In some embodiment, the method of producing a conjugate of a *Neisseria meningitidis* capsular polysaccharide to a carrier protein, comprises
a) partially de-O-acetylating the polysaccharide by alkaline hydrolysis;
b) activating the polysaccharide by periodate treatment, thereby converting diols to aldehydes to an extent of at least 10, 15, 20, 25, 30, 35, 40, or 50 nmol aldehyde per mg polysaccharide;
c) conjugating the activated polysaccharide to the carrier protein by reductive amination, wherein the polysaccharide is present in the conjugation reaction at a weight-to-weight ratio of 0.5-1 to 5:1 relative to the carrier protein, thereby forming the conjugate.

In some embodiments, a method of producing a conjugate of a *Neisseria meningitidis* capsular polysaccharide to a carrier protein comprises
a) activating the polysaccharide by periodate treatment, thereby converting diols to aldehydes to an extent of at least 25, 30, 35, 40, 45, 50, 55, 60, 65, 70, or 75 nmol aldehyde per mg polysaccharide; and
b) conjugating the activated polysaccharide to the carrier protein by reductive amination, wherein the polysaccharide is present in the conjugation reaction at a weight-to-weight ratio of 1:1 to 5:1 relative to the carrier protein, thereby forming the conjugate.

In some embodiments, the method of purifying further comprises purifying the conjugate by hydrophobic interaction chromatography (HIC).

A. Exemplary Vaccine Formulations

Formulation of the vaccine compositions of the present invention can be accomplished using art recognized methods. The vaccine compositions/formulations of the present invention may also contain one or more adjuvants. Adjuvants include, by way of example and not limitation, aluminum adjuvants, Freund's Adjuvant, BAY, DC-chol, pcpp, monophoshoryl lipid A, CpG, QS-21, cholera toxin and formyl methionyl peptide. See, e.g., Vaccine Design, the Subunit and Adjuvant Approach, 1995 (M. F. Powell and M. J. Newman, eds., Plenum Press, N.Y.). The adjuvant, if present, can be an aluminum adjuvant, such as aluminum hydroxide or aluminum phosphate. In some embodiments, the vaccine compositions and formulations, e.g., the MenACWY-TT vaccine, does not comprise adjuvant. In some embodiments, the vaccine compositions and formulations, e.g., the MenACWY-TT vaccine comprises adjuvant.

The vaccine compositions and formulations (e.g., conjugate vaccines/MenACWY-TT vaccine) of the present invention can be administered as a single dose or in a series (i.e., with a "booster" or "boosters"), or as a booster after earlier administration of a different *Neisseria meningitidis* vaccine, such as a *Neisseria meningitidis* capsular saccharide conjugate vaccine. For example, a child could receive a single dose early in life, then be administered a booster dose up to ten years later, as is currently recommended for other vaccines to prevent childhood diseases. In some embodiments, a dose of a vaccine described herein is administered two months to ten years after a previously administered *Neisseria meningitidis* capsular saccharide conjugate vaccine, such as two to four months, four to six months, six to twelve months, 1 year to 2 years, 2 years to 3 years, 3 years to 4 years, 4 years to 5 years, 5 years to 6 years, 6 years to 7 years, 7 years to 8 years, 8 years to 9 years, or 9 years to 10 years after the previously administered *Neisseria meningitidis* capsular saccharide conjugate vaccine.

The booster dose will generate antibodies from primed B-cells, i.e., an anamnestic response. That is, the vaccine compositions and formulations, e.g., the MenACWY-TT vaccine, elicits a high primary (i.e., following a single administration of vaccine) functional antibody response in younger and older populations, and is capable of eliciting an anamnestic response (i.e., following a booster administration), demonstrating that the protective immune response elicited by the vaccine compositions and formulations, e.g., the MenACWY-TT vaccine of the present invention is long-lived.

In some embodiments, the administration is intramuscular injection. In some embodiments, the administration is subcutaneous, intradermal, intraperitoneal, parenteral or intravenous. Compositions and formulations may be in admixture with a suitable carrier, diluent, or excipient such as a sodium acetate buffered saline solution, sterile water, physiological saline or the like. The compositions/formulations can also be lyophilized. The compositions/formulations can contain auxiliary substances such as wetting or emulsifying agents, pH buffering agents, gelling or viscosity enhancing additives, preservatives, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

In some embodiments, the vaccine composition/formulation is a liquid preparation. In some embodiments, the vaccine composition/formulation, e.g., MenACWY-TT vaccine, is a liquid composition to be administered by injection to animals, children, particularly small children, older adults, e.g., over 55, 60, 65, 70, 75, 80, or 90.

The choice of suitable carriers and other additives will depend on the exact route of administration and the nature of the particular dosage form.

In one embodiment, the vaccine compositions and formulations, e.g., the MenACYW-TT vaccine, comprises a pharmaceutically acceptable preservative, carrier, buffer excipient, or the like. In one embodiment, the pharmaceutically acceptable preservative, carrier, or excipient increases or extends the shelf life of the compositions. In some embodiments, the vaccine comprises a buffer. In some embodiments, the buffer is sodium acetate. In some embodiments, the buffer is sodium phosphate. In some embodiments, the buffer is present at a concentration ranging from 10 mM to 100 mM, for example, 10 mM to 70 mM, 15 mM to 45 mM, 20 mM to 40 mM, 40 mM to 60 mM, or 60 mM to 100 mM. In some embodiments, the buffer has a pH of 4.5 to 7.5, 4.5 to 7.0, 4.5 to 6.5, 4.5 to 6.0, 4.5 to 5.5, or 4.5 to 5.0. In some embodiments, the buffer has a pH ranging from 5.5 to 7.0, for example, 5.75 to 6.25, or 6.25 to 6.75. In some embodiments, the buffer has a pH of 5.5 to 6.5. In some embodiments, the buffer has a pH of 5 or 6. In some embodiments, the vaccine composition comprises a pharmaceutically acceptable salt. In some embodiments, the vaccine composition/formulation comprises saline. In some embodiments, the saline comprises or is NaCl. The NaCl may be present at a concentration of 0.45% to 0.9% w/v, such as 0.5% to 0.85% w/v, or 0.6% to 0.8% w/v, or 0.6%, 0.67%, 0.75%, 0.8%, 0.85%, or 0.9%.

In one embodiment, each component of the composition is chemically inert with respect to the *N. meningitidis* polysaccharide-protein carrier conjugates.

In some embodiments, the vaccine compositions and formulations, e.g., the MenACWY-TT vaccine, is formulated as a single unit dose. In some embodiments, the single unit dose comprises from 6 μg to 15 μg of each of the MenA, MenC, MenW-135, and MenY polysaccharides. In some embodiments, the single unit dose comprises 4, 5, 6, 7, 8, 9, 10, 11, 12, 13, 14, or 15 μg of each of the MenA, MenC, MenW-135, and MenY polysaccharides. In some embodiments, the carrier protein is present in an amount from 50 μg to 80 μg in the single unit dose. In some embodiments, the carrier protein is present in an amount from 45, 50, 55, 60, 65, 70, 75, or 80 μg in the single unit dose.

In some embodiments, the vaccine compositions and formulations, e.g., the MenACWY-TT vaccine is formulated as a 0.5 mL dose in sodium acetate, sodium acetate buffered saline or similar buffer. In some embodiments, the 0.5 mL dose comprises 2, 3, 4, 5, 6, 7, 8, 9, 10, 11, 12, 13, 14, or 15 μg each of serogroups A, C, Y, and W-135 conjugated to 50, 55, 60, 65, 70, 80, 85, or 90 μg of tetanus toxoid protein. In some embodiments, this 0.5 mL dose is administered intramuscularly.

B. Exemplary Methods and Uses

In some embodiments, a method of vaccinating a subject against *Neisseria meningitidis* is encompassed comprising administering the vaccine compositions or formulations, e.g., the MenACWY-TT vaccine, described herein. In some embodiments, the invention comprises a use of the vaccine composition or formulation described herein to immunize a subject against *Neisseria meningitidis*. In some embodiments, a use of the vaccine composition or formulation described herein for the manufacture of a medicament for immunizing a subject against *Neisseria meningitidis* is encompassed.

In some embodiments, the subject is 12 months old or older when vaccinated. In some embodiments, the subject is on older adult when vaccinated. In some embodiments, the older adult is age 50, 55, 60, 65, 70, 75, 80, 85, 90, or 100 when vaccinated.

In some embodiments, the subject is from age 6 weeks to 3 years when vaccinated. In some embodiments, the subject is 4, 5, 6, 7, 8, 9, or 10 weeks when vaccinated. In some embodiments, the subject is 2 months, 4 months, 6 months, 12 months and/or 15 months when vaccinated. In some embodiments, the subject is vaccinated based on age. In some embodiments, the subject is given three doses of the vaccine compositions or formulations, e.g., the MenACWY-TT vaccine, described herein at 6-8, 10-12, and 14-16 weeks.

In some embodiments, the subject is vaccinated more than once throughout a life. In some embodiments, the subject receives a booster dose 3 years or longer after the first dose. In some embodiments, the subject receives a booster dose 4 years or longer after the first dose. In some embodiments, the subject is vaccinated up to three times before their first birthday, and once around or after their first birthday. In some embodiments, the first vaccination is at 2, 3, 4, 5, 6, 7, 8, 9, or 10 weeks of age. In some embodiments, the first or second vaccination is at 3, 4, or 5 months of age. In some embodiments, the first, second, or third vaccination is at 5, 6, or 7 months of age. In some embodiments, the first, second, third, or fourth vaccination is at 11, 12, 13, 14, or 15 months of age. In some embodiments, the first, second, third, or fourth vaccination is at 14, 15, 16, 17, or 18 months of age. In some embodiments, the first vaccination is at 6, 7, 8, or 9 months and a second vaccination is given up to 24 months. In some embodiments, the subject is vaccinated as an older adult, regardless of whether or not they had previously received the MenACWY-TT or other vaccine against *Neisseria meningitidis*. In some embodiments, the subject is age 50 years or more, 55 years or more, 60 years or more, or 65 years or more when vaccinated with the vaccine compositions or formulations, e.g., the MenACWY-TT vaccine, described herein.

In some embodiments, the vaccine compositions or formulations, e.g., the MenACWY-TT vaccine, described herein are administered at the same time as other routine vaccines. In some embodiments, the routine vaccines include, for example, Pentacel® (DTaP5-IPV/Hib), Prevnar® (PCV7), Prevnar 130 (PCV13), RotaTeqe (RV5), ROTARIX® (RV1), ENGERIX-B® (HepB), RECOMBIVAX HB® (HepB), M-M-R® (MMR), M-M-R®$_{II}$ (MMR), and VARIVAX® (V) vaccines. In some embodiments, the routine vaccines include, for example, Adacel® (Tdap5) and Gardasil® (HPV4). In some embodiments, the routine vaccines include DTaP5-IPV/HibHepB, Other routine vaccines are known in the art and may be provided to the subject at the same time, before, or after, the vaccine compositions or formulations, e.g., the MenACWY-TT vaccine, described herein.

IV. Examples

The following are examples of methods, uses, and compositions disclosed herein. It is understood that various other embodiments may be practiced, given the general and detailed descriptions provided above. The following examples are given for the purpose of illustrating the present teachings and shall not be construed as being a limitation on the scope of the disclosure or claims.

1. Preparation of Group A Conjugates

Example 1A

Figures 1A, 1B:
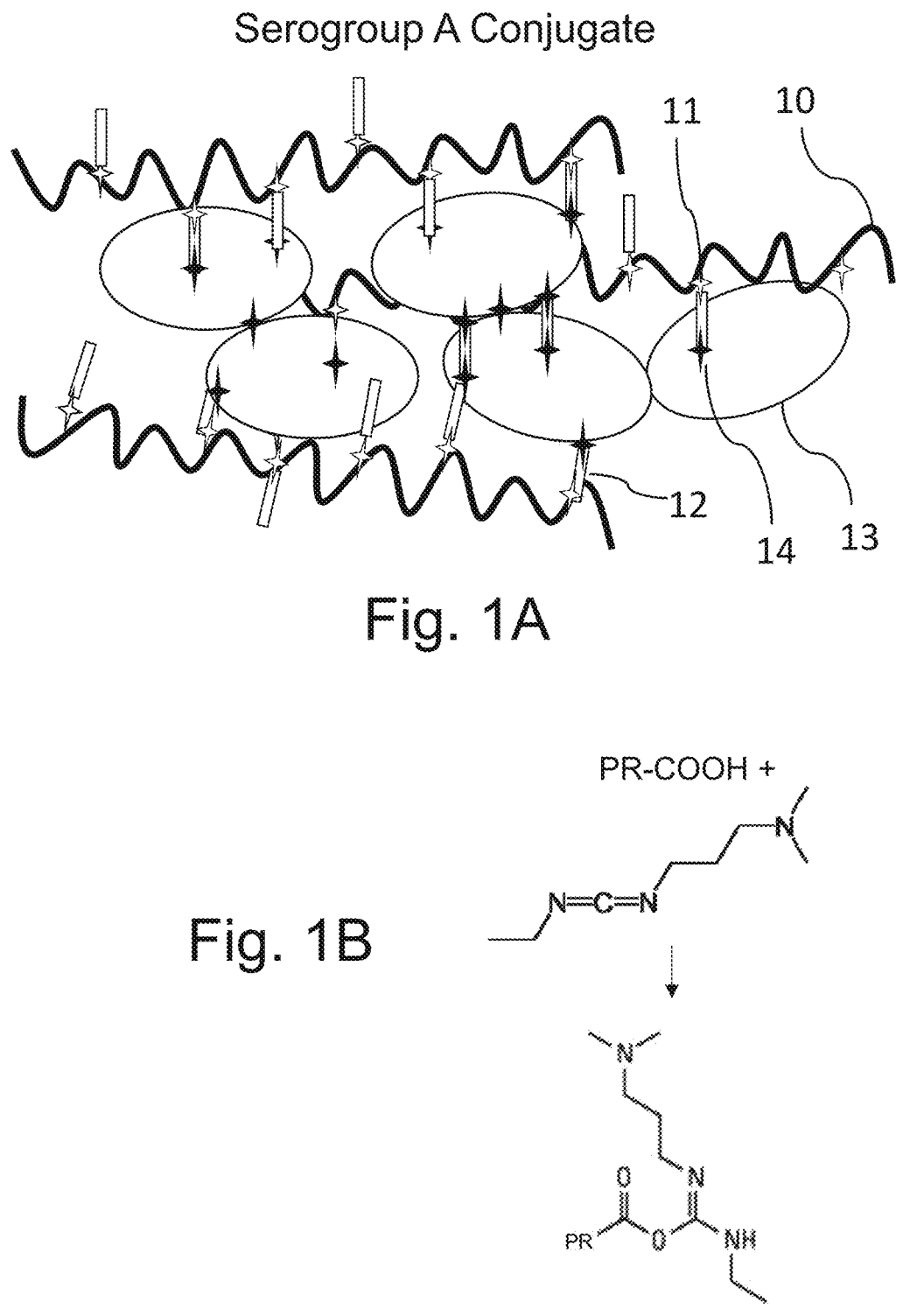
Figure 1C:
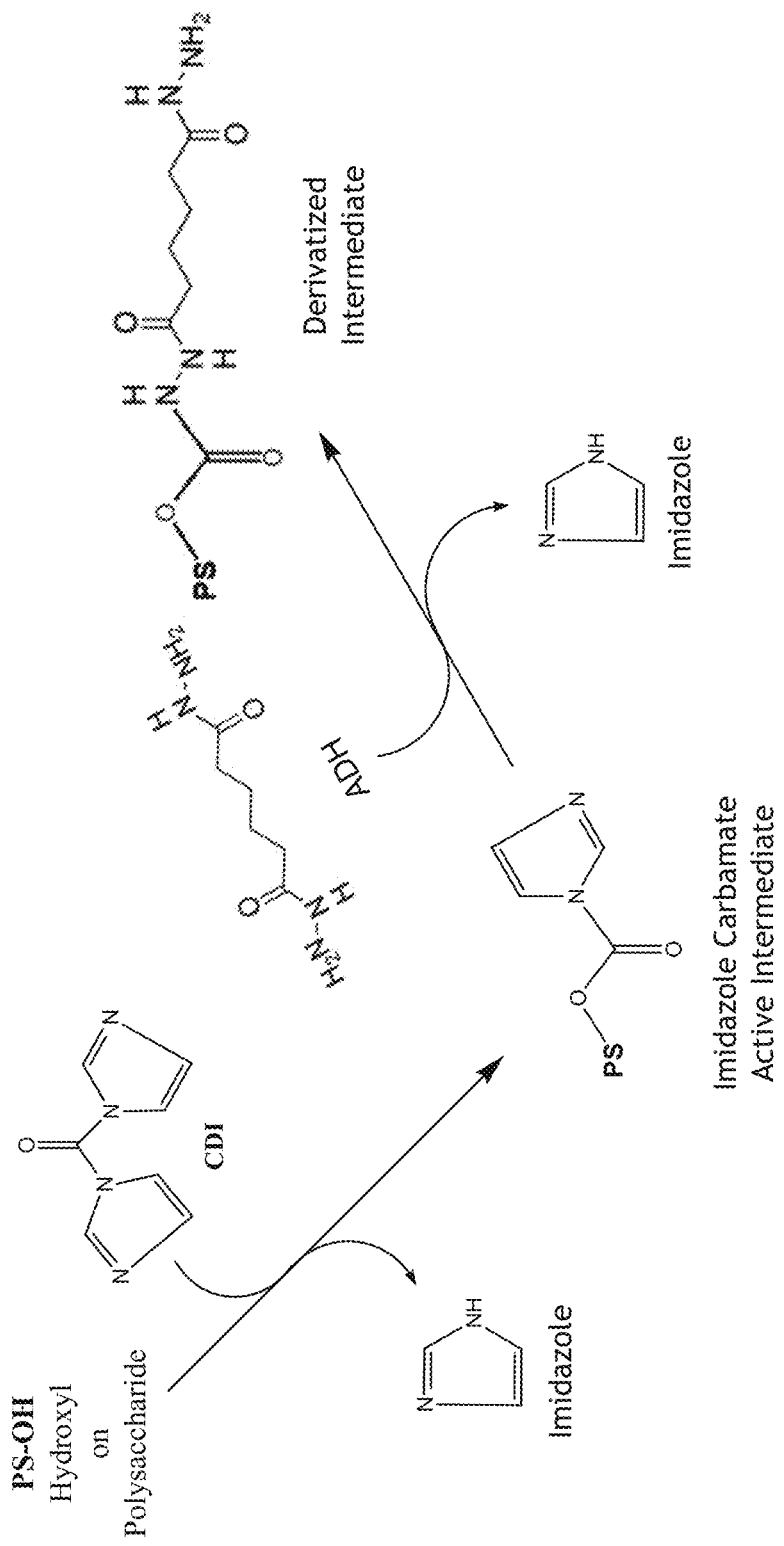
FIG. 1H shows the product of the reaction in FIG. 1F with the structure of the linked polysaccharide repeat unit (including ADH residue) drawn out.

Group A purified capsular polysaccharide is dissolved in 10% by weight tetrabutylammonium chloride (TBAC) in dimethylsulfoxide (DMSO) to a target concentration of 8 mg/mL. The solution is mixed until the polysaccharide is fully dissolved at 19-25° C. The dissolved polysaccharide is activated by addition of a target concentration of 35-45 molar excess of carbonyldiimidazole (CDI) per N-acetylmannosamine phosphate repeat unit (PS RU), and mixed for 50 to 70 minutes at 19-25° C. (FIG. 1C, first reaction; product shown in FIG. 1E). The polysaccharide solution is diluted 1:2 with WFI (50% v/v) to adjust the concentration of the activated polysaccharide to 4 mg/mL in 50% DMSO. The solution is derivatized by adding Adipic acid Dihydrazide (ADH) (1.0 mol ADH per 1-3 mol PS RU) (FIG. 1C, second reaction; product shown in FIG. 1F) and mixed overnight at room temperature. The reaction gives an amount of derivatization such that there is one bound ADH per 10 to 100 polysaccharide repeat units, e.g., one bound ADH per 20, 30, 40, 50, or 60 polysaccharide repeat units. The activated polysaccharide is concentrated by ultrafiltration on the 10 kDa MWCO PES membrane and then diafiltered against 12-18 volume exchanges of physiological saline. The target concentration is approximately 30 mg/mL. The activated polysaccharide is filtered and is stored at 1-5° C.

Figure 1D:
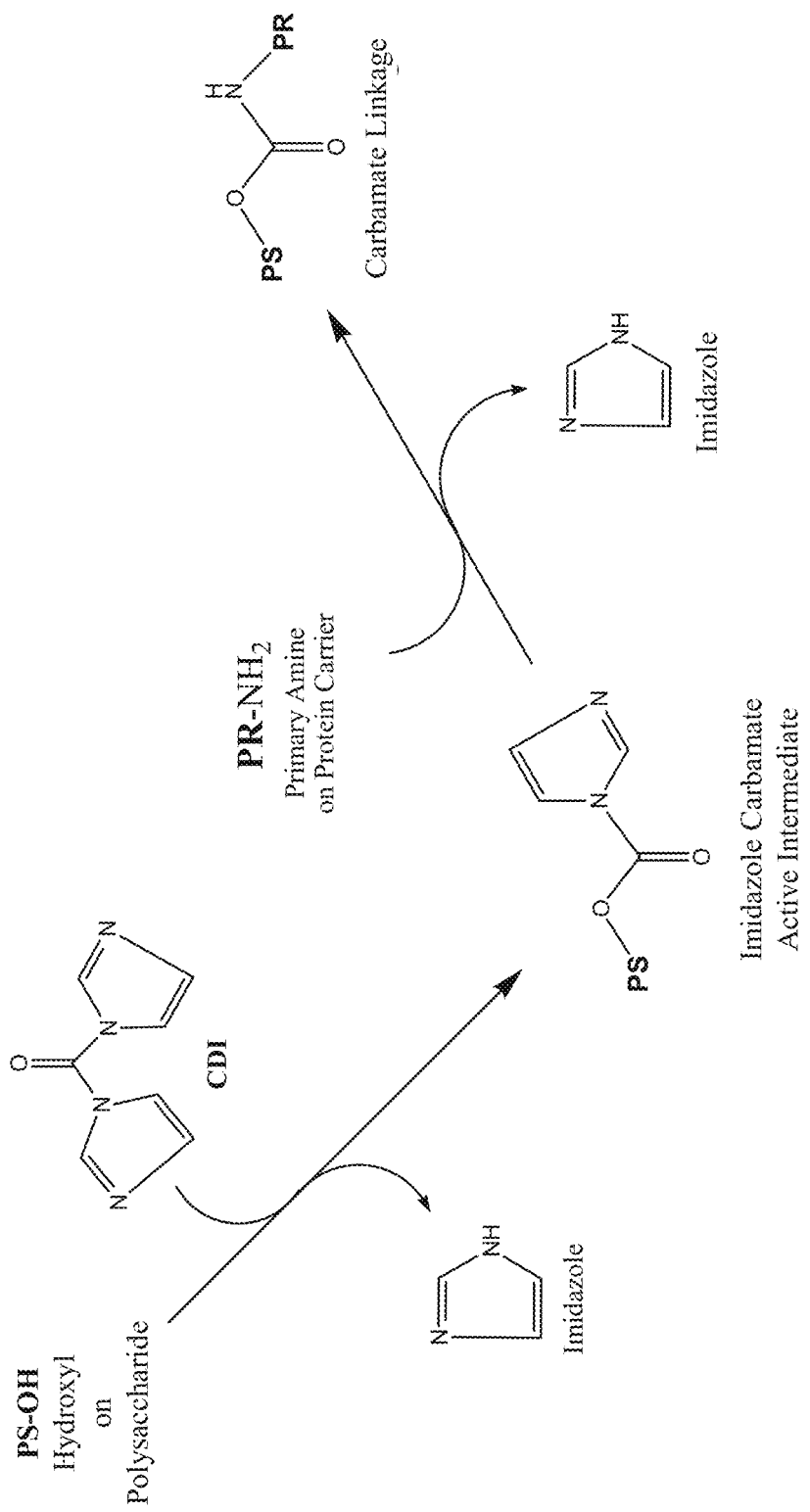
Figure 1E:
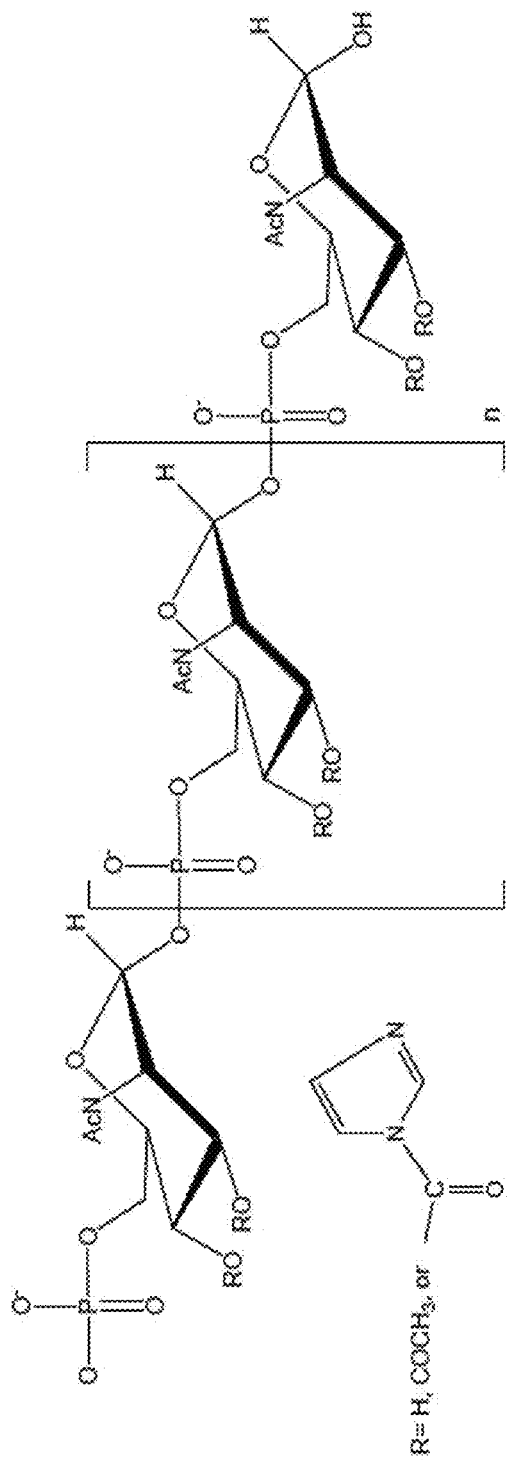
Figure 1F:
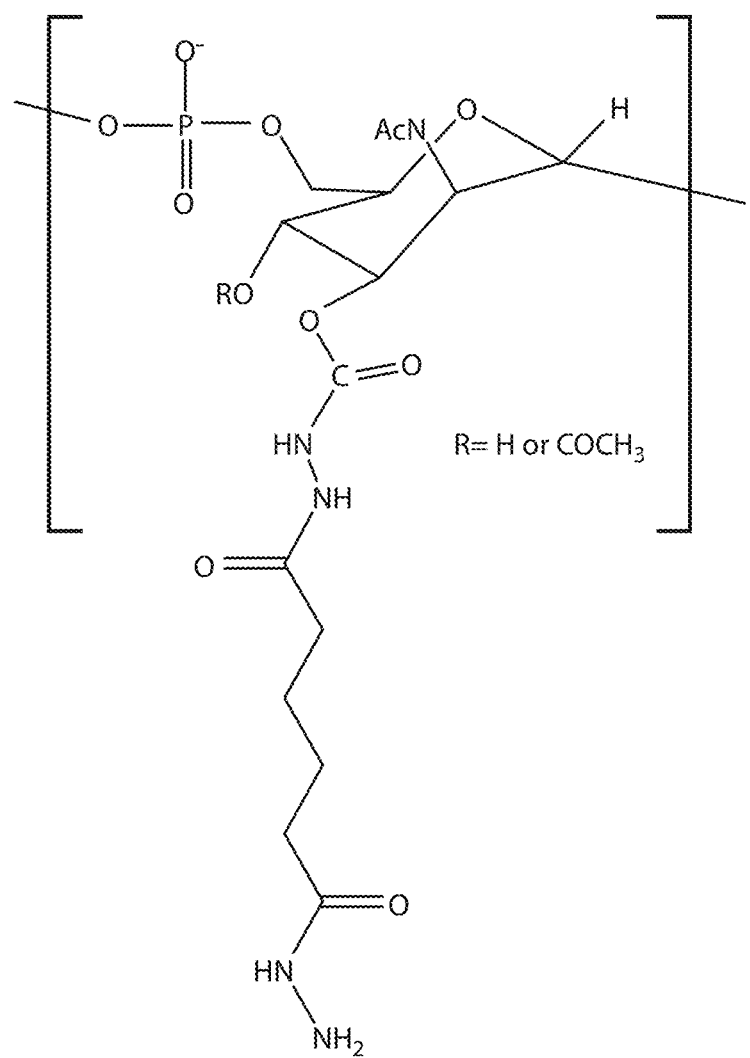
Figure 1G:
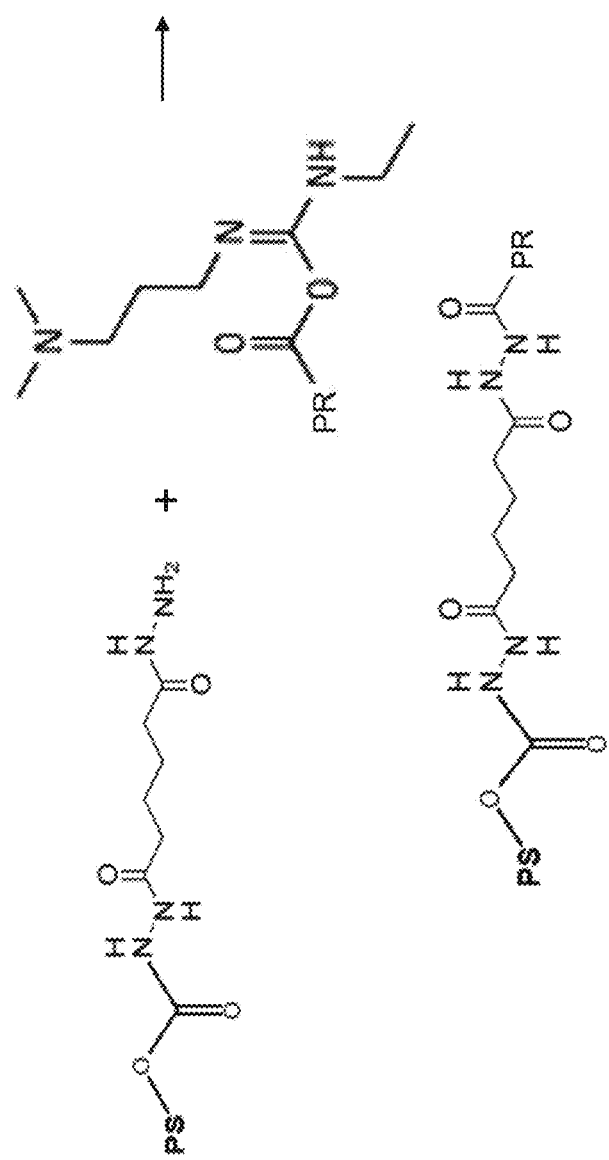
Figure 1H:
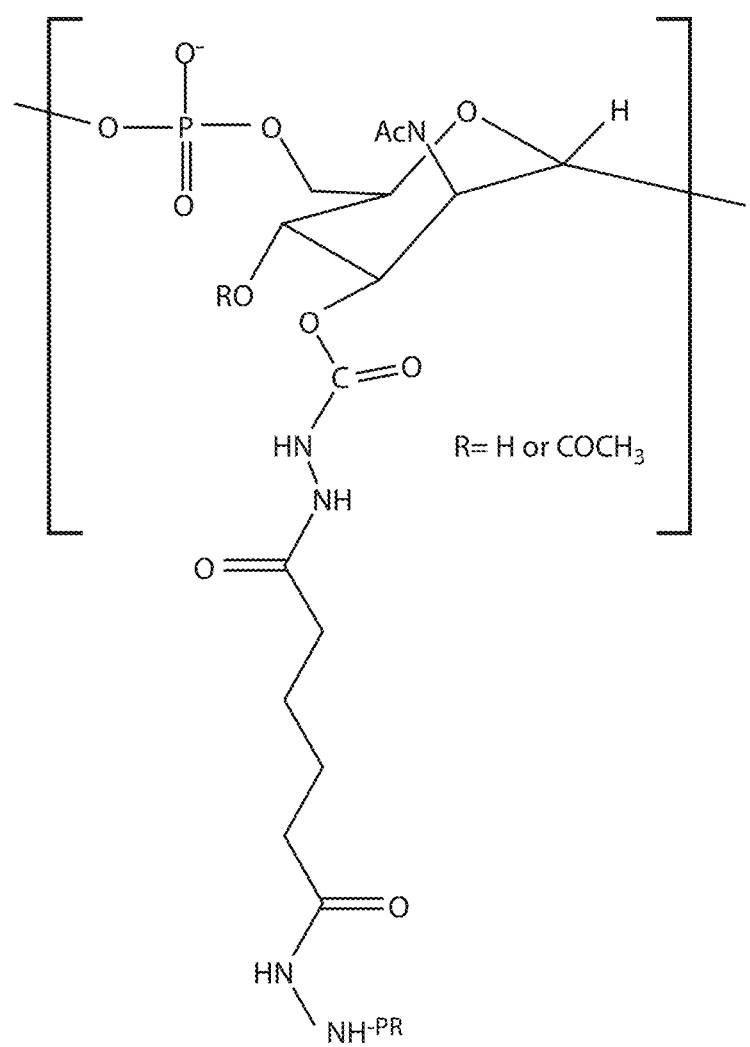

Purified Tetanus Toxoid protein (TT) is filtered through a 0.2 micron membrane and stored at 1-5° C. The derivatized polysaccharide and concentrated Tetanus protein are mixed together, in a ratio of 0.5:1, 1:1, 2:1, 3:1, 4:1, or 5:1. An aliquot of 100 mg/mL of the cross linking agent 1-ethyl-3-(dimethylaminopropyl) carbodiimide (EDAC) in 1.0 M MES buffer, pH 5.7 is added to the polysaccharide-protein mixture such that a final concentration of EDAC is 10 mg/mL and MES is 100 mM. Saline is added to give target concentrations of 16 mg/mL Polysaccharide and 4 mg/mL TT. The final pH is adjusted to 5.5-5.9 and the reaction is mixed at 15.6-23.9° C. for 16-24 hours. During this time, the EDAC and TT react to form an O-acylisourea intermediate (FIG. 1B). The O-acylisourea intermediate and the derivatized polysaccharide then form a conjugate (FIG. 1G; products shown in FIG. 1H and FIG. 1A).

Ammonium sulfate is added to the conjugate reaction to yield a 1 M ammonium sulfate concentration. The pH is adjusted to 7 and is mixed until dissolved at room temperature. The conjugate reaction mixture is applied to a HIC column packed with phenyl resin. The unconjugated polysaccharide is eluted with 2 to 7 column volumes of 1 M ammonium sulfate solution. The conjugate is eluted with WFI. In this and subsequent examples, the HIC purification of the conjugate can provide a product in which less than 20% of the polysaccharide by mass is free (unconjugated) polysaccharide. The conjugate eluate is diafiltered against 10 volume exchanges of 50 mM sodium acetate, pH 6.0, using a 100 kDa MWCO PES membrane. The final filtration of the purified conjugate is performed using a 0.2 micron membrane and the conjugate is stored at 1-5° C.

Example 1B

Group A purified capsular polysaccharide is dissolved in tetrabutylammonium chloride (TBAC)/dimethylsulfoxide (DMSO) by weight to a target concentration of 6 mg/mL. The solution is mixed for 16 to 24 hours at 19-25° C. The dissolved polysaccharide is activated by addition of a target concentration of 35-45 molar excess of carbonyldiimidazole (CDI) per N-acetylmannosamine phosphate repeat unit (PS RU), and mixed for 50 to 70 minutes at 19-25° C. (FIG. 1C, first reaction; product shown in FIG. 1E). The polysaccharide solution is diluted 1:2 with WFI (45-55% v/v) such that the activated polysaccharide is at a target concentration of 3 mg/mL in 50% DMSO.

Purified Tetanus Toxoid protein (TT) is filtered through a 0.2 micron membrane and stored at 1-5° C. The Tetanus protein is added to a final concentration of 1 mg/mL. During this time, the activated polysaccharide and TT react to form a conjugate with a carbamate linkage (FIG. 1D). The reaction proceeds overnight at room temperature.

Ammonium sulfate is added to the conjugate reaction to yield a 1 M ammonium sulfate concentration. The pH is adjusted to 7 and is mixed until dissolved at room temperature. The conjugate reaction mixture is applied to a HIC column packed with phenyl resin. The unconjugated polysaccharide is eluted with 2 to 7 column volumes of 1 M ammonium sulfate solution. The conjugate is eluted with WFI. In this and subsequent examples, the HIC purification of the conjugate can provide a product in which less than 20% of the polysaccharide by mass is free (unconjugated) polysaccharide. The conjugate eluate is diafiltered against 10 volume exchanges of 50 mM sodium acetate, pH 6.0, using a 100 kDa MWCO PES membrane. The final filtration of the purified conjugate is performed using a 0.2 micron membrane and the conjugate is stored at 1-5° C.

2. Preparation of Group C Conjugates

Example 2A

Group C purified capsular polysaccharide is dissolved in physiological saline to a target concentration of 10 mg/mL.

The solution is mixed until dissolved. The temperature of the polysaccharide solution is adjusted to 37° C. and sodium hydroxide (NaOH) is added to a target final concentration of 100 mM NaOH. The solution is mixed and incubated for 20 minutes, providing partial de-O-acetylation such that the polysaccharide in the final conjugate will have an O-acetylation level of 0.8 to 1.4 μmol OAc/mg polysaccharide and/or a reduction of 50% to 60% relative to the O-acetylation level of the starting material. Native MenC polysaccharide has two potential O-acetylation positions per monosaccharide repeat unit, and generally has an overall O-acetylation level of 40-45% for all possible O-acetylation sites. A 50% reduction in 0-acetyl groups relative to the starting material will give an overall O-acetylation level (of all possible O-acetylation sites) of less than 25%.

The pH is adjusted to 6 and the temperature is decreased to 15° C. The dissolved polysaccharide is activated by the addition of sodium meta periodate (FIG. 2B) such that the target concentration is 2 mM. The pH is adjusted to 6 and the solution is mixed at 15° C. The periodate oxidizes and cleaves at adjacent diol positions, giving aldehyde-terminated chains. The reaction is mixed until the mean molecular size is reduced to between 50,000 and 100,000 Dalton, as determined by HPSEC. The reducing activity (reflecting the amount of aldehydes) is 40 to 100 nmol/mg polysaccharide. The reaction is quenched by adding glycerol in an amount of 0.5 mL glycerol per gram of polysaccharide and mixing for a minimum of 5 minutes. The polysaccharide is initially concentrated by ultrafiltration using a 5 kDa MWCO regenerated cellulose filter and then diafiltered against 8-12 volume exchanges of 50 mM sodium acetate buffer, pH 6.0. The material is further concentrated to a target concentration of 50 mg/mL. The depolymerized/activated polysaccharide is filtered and stored.

Purified Tetanus Toxoid protein is concentrated on a 10 kDa MWCO PES membrane to a target final concentration of up to 100 mg/mL and then passed through a 0.2 micron filter. The filtered protein solution is stored at 1-5° C. The depolymerized/activated polysaccharide and concentrated Tetanus protein are mixed together, in a mass ratio of 0.5:1, 1:1, 2:1, 3:1, 4:1, or 5:1 (polysaccharide:protein). An aliquot of 100 mg/mL of sodium cyanoborohydride in 2.0 M phosphate buffer is added to the polysaccharide-protein mixture such that the sodium cyanoborohydride is 10 mg/mL and the phosphate buffer is 200 mM, pH 8.0. Saline is added to adjust concentrations, e.g., to a target of 15-50 mg/mL for polysaccharide. The reaction (FIG. 2C) is mixed at 37° C. for 16-30 hours. The reaction is diluted 1:2 with 6 mM phosphate buffered saline (PBS). An aliquot of 100 mg/mL sodium borohydride in 6 mM PBS is added to the reaction mixture to obtain a target 0.5 mg of sodium borohydride per mL of reaction volume. The reaction is mixed for a minimum of 15 minutes at room temperature. The sodium borohydride caps unreacted aldehydes by reducing them to alcohols, giving a terminal unlinked saccharide with a primary hydroxyl at the 7 position, or wherein the reducing end is modified with a (2-hydroxy)ethoxy. Products (terminal saccharides not shown) are illustrated in FIG. 2D and FIG. 2A. The conjugation solution is diafiltered against 10 volume exchanges of 6 mM PBS on a 50 kDa MWCO PES membrane. The solution is stored at 1-5° C.

Ammonium sulfate is added to the conjugate reaction to yield a 1 M ammonium sulfate concentration. The pH is adjusted to 7 and is mixed until dissolved at room temperature. The conjugate reaction mixture is applied to a HIC column packed with phenyl resin. The unconjugated polysaccharide is eluted with 2 to 7 column volumes of 1 M ammonium sulfate solution. The conjugate is eluted with WFI. In this and subsequent examples, the HIC purification of the conjugate can provide a product in which less than 20% of the polysaccharide by mass is free (unconjugated) polysaccharide. The conjugate eluate is diafiltered against 10 volume exchanges of 50 mM sodium acetate, pH 6.0, using a 100 kDa MWCO PES membrane. The final filtration of the purified conjugate is performed using a 0.2 micron membrane and the conjugate is stored at 1-5° C.

Example 2B

Group C purified capsular polysaccharide is dissolved in physiological saline to a target concentration of 10 mg/mL. The solution is mixed until dissolved. The pH is adjusted to 6.0 and the temperature is changed to 15° C. The dissolved polysaccharide is activated by the addition of sodium meta periodate (FIG. 2B) such that the target concentration is 2 mM. The reaction is mixed until the mean molecular size is between 50,000 and 100,000 Dalton, as determined by HPSEC. The reaction is quenched by adding glycerol in an amount of 0.5 mL glycerol per gram of polysaccharide and mixing for a minimum of 5 minutes. The polysaccharide is initially concentrated by ultrafiltration using a 5 kDa MWCO regenerated cellulose filter and then diafiltered against 8-12 volume exchanges of 50 mM sodium acetate buffer, pH 6.0. The material is further concentrated to a target concentration of 50 mg/mL. The depolymerized/activated polysaccharide is filtered and is stored at 1-5° C.

Purified Tetanus Toxoid protein is concentrated on a 10 kDa MWCO PES membrane to a target final concentration of up to 100 mg/mL and then passed through a 0.2 micron filter. The filtered protein solution is stored at 1-5° C. The depolymerized/activated polysaccharide and concentrated Tetanus protein are mixed together, in a mole ratio of 0.5:1, 1:1, 2:1, 3:1, 4:1, or 5:1 (polysaccharide:protein). An aliquot of 100 mg/mL of sodium cyanoborohydride in 2.0 M phosphate buffer is added to the polysaccharide-protein mixture such that the sodium cyanoborohydride is 10 mg/mL and the phosphate buffer is 200 mM, pH 8.0. Saline is added to adjust concentrations, e.g., to a target of 15-50 mg/mL for polysaccharide. The reaction (FIG. 2C) is mixed at 37° C. for 16-30 hours. The reaction is diluted 1:2 with 6 mM phosphate buffered saline (PBS). An aliquot of 100 mg/mL sodium borohydride in 6 mM PBS is added to the reaction mixture to obtain a target 0.5 mg of sodium borohydride per mL of reaction volume. The reaction is mixed for a minimum of 15 minutes at room temperature. The sodium borohydride caps unreacted aldehydes by reducing them to alcohols, giving a terminal unlinked saccharide with a primary hydroxyl at the 7 position, or wherein the reducing end is modified with a (2-hydroxy)ethoxy. Products (terminal saccharides not shown) are illustrated in FIG. 2D and FIG. 2A. The conjugation solution is diafiltered against 10 volume exchanges of 6 mM PBS on a 50 kDa MWCO PES membrane. The solution is stored at 1-5° C.

Ammonium sulfate is added to the conjugate reaction to yield a 1 M ammonium sulfate concentration. The pH is adjusted to 7 and is mixed until dissolved at room temperature. The conjugate reaction mixture is applied to a HIC column packed with phenyl resin. The unconjugated polysaccharide is eluted with 2 to 7 column volumes of 1 M ammonium sulfate solution. The conjugate is eluted with WFI. In this and subsequent examples, the HIC purification of the conjugate can provide a product in which less than 20% of the polysaccharide by mass is free (unconjugated) polysaccharide. The conjugate eluate is diafiltered against 10 volume exchanges of 50 mM sodium acetate, pH 6.0, using a 100 kDa MWCO PES membrane. The final filtration of the purified conjugate is performed using a 0.2 micron membrane and the conjugate is stored at 1-5° C.

3. Preparation of Group W-135 and Y Conjugates

Group W-135 purified capsular polysaccharide is dissolved in sodium acetate buffer to a target concentration of 10 mg/mL. The solution is mixed until dissolved. The polysaccharide solution is heated to 50-70° C. using a jacketed heat exchanger. The pH is adjusted to 4.5. The reaction (FIG. 4A, step 1) is allowed to mix until the mean molecular size is 150,000 Dalton, as determined by HPSEC. The reaction mixture is cooled to 1-5° C. Sodium meta periodate is added to the polysaccharide solution such that the target meta periodate concentration is 2 mM (FIG. 4A, step 2). The pH is adjusted to 6.0 and the solution is mixed for 60 minutes between 0 and 5° C. The periodate oxidizes and cleaves at adjacent diol positions, giving aldehydes, e.g., at the 7-position of a sialic acid residue as shown in FIG. 4A. The reducing activity (reflecting the amount of aldehydes) is 60 to 150 nmol/mg polysaccharide. The reaction is quenched by adding 0.5 mL of glycerol per gram of polysaccharide and mixing for a minimum of 5 minutes. The polysaccharide is concentrated by ultrafiltration using a 10 kDa MWCO regenerated cellulose filter and then diafiltered against 10 volume exchanges of 50 mM sodium acetate buffer, pH 6.0. The material is further concentrated to a target concentration of 50 mg/mL. The depolymerized/activated polysaccharide is filtered and stored at 1-5° C.

Purified Tetanus Toxoid protein is concentrated on a 10 kDa MWCO PES membrane to a target final concentration of up to 100 mg/mL and then passed through a 0.2 micron filter and is stored at 1-5° C. The depolymerized/activated polysaccharide and concentrated Tetanus protein are mixed together in a mass ratio of 0.5:1, 1:1, 2:1, 3:1, 4:1, or 5:1 (polysaccharide:protein). An aliquot of 100 mg/mL of sodium cyanoborohydride in 2.0 M phosphate buffer is added to the polysaccharide-protein mixture such that the sodium cyanoborohydride is 10 mg/mL and the phosphate buffer is 200 mM, pH 9.0. Saline is added to adjust target concentration, e.g., to a target of 15-50 mg/mL for polysaccharide. The reaction (FIG. 4B) is mixed at room temperature overnight.

The reaction is diluted 1:2 with 6 mM phosphate buffered saline (PBS). An aliquot of 100 mg/mL sodium borohydride in 6 mM PBS is added to the reaction mixture to obtain a target 0.5 mg of sodium borohydride per mL of reaction volume. The reaction is mixed for a minimum of 15 minutes at room temperature. The sodium borohydride caps unreacted aldehydes by reducing them to alcohols. Products are shown in FIG. 4C and FIG. 3.

Ammonium sulfate is added to the conjugate reaction to yield a 1 M ammonium sulfate concentration. The pH is adjusted to 7 and is mixed until dissolved at room temperature. The conjugate reaction mixture is applied to a HIC column packed with phenyl resin. The unconjugated polysaccharide is eluted with 2 to 7 column volumes of 1 M ammonium sulfate solution. The conjugate is eluted with WFI. The conjugate eluate is diafiltered against 10 volume exchanges of 50 mM sodium acetate, pH 6.0, using a 100 kDa MWCO PES membrane. The final filtration of the purified conjugate is performed using a 0.2 micron membrane and the conjugate is stored at 1-5° C. The same process can be used for Group Y purified capsular polysaccharide 4. Formulation of Quadrivalent Vaccines Example 4A A quadrivalent MenACYW-TT conjugate vaccine is formulated from the 4 monovalent PS-protein conjugates prepared as described in Examples 1A, 2A, and 3-4 and diluted in a sodium acetate buffered saline solution to final concentration of 10 µg PS/serogroup/0.5 mL. That is, a 0.5 mL dose of MenACYW conjugate vaccine contains 10 µg of each of the meningococcal PS serogroups A, C, Y, and W-135, conjugated to 45 to 80 µg total of tetanus toxoid protein (the actual quantity of tetanus toxoid protein is dependent on the particular PS-to-protein ratios of the monovalent bulk concentrate lots used in the formulations).

Each 0.5 mL dose of MenACYW conjugate vaccine is formulated in a 30 mM sodium acetate-buffered pH 6.0 saline solution.

Example 4B

A quadrivalent MenACYW-TT conjugate vaccine is formulated from the 4 monovalent PS-protein conjugates prepared as described in Examples 1A, 2B, and 3-4 and diluted in a sodium acetate buffered saline solution to final concentration of 10 µg PS/serogroup/0.5 mL. That is, a 0.5 mL dose of MenACYW conjugate vaccine contains 10 µg of each of the meningococcal PS serogroups A, C, Y, and W-135, conjugated to 45 to 80 µg total of tetanus toxoid protein (the actual quantity of tetanus toxoid protein is dependent on the particular PS-to-protein ratios of the monovalent bulk concentrate lots used in the formulations).

Each 0.5 mL dose of MenACYW conjugate vaccine is formulated in a 30 mM sodium acetate-buffered pH 6.0 saline solution.

Example 4C

A quadrivalent MenACYW-TT conjugate vaccine is formulated from the 4 monovalent PS-protein conjugates prepared as described in Examples 1B, 2B, and 3-4 and diluted in a sodium acetate buffered saline solution to final concentration of 10 µg PS/serogroup/0.5 mL. That is, a 0.5 mL dose of MenACYW conjugate vaccine contains 10 µg of each of the meningococcal PS serogroups A, C, Y, and W-135, conjugated to 45 to 80 µg total of tetanus toxoid protein (the actual quantity of tetanus toxoid protein is dependent on the particular PS-to-protein ratios of the monovalent bulk concentrate lots used in the formulations).

Each 0.5 mL dose of MenACYW conjugate vaccine is formulated in a 30 mM sodium acetate-buffered pH 6.0 saline solution.

5. Properties and Immunogenicity of Exemplary Conjugates

A MenA conjugate was prepared generally as described above without an ADH linker, except that the polysaccharide concentration used in the conjugation reaction with tetanus toxoid was 12 mg/ml. The conjugate had a 0.3 polysaccharide/protein (PS/PR) mass ratio. The O-acetylation level was determined to be 3.0 µmol/mg polysaccharide.

A MenA conjugate was prepared generally as described above with an ADH linker, except that the polysaccharide concentration used in the conjugation reaction with tetanus toxoid was 12 mg/ml. The conjugate had a 1.0 PS/PR mass ratio. The O-acetylation level determined to be 2.8 µmol/mg polysaccharide. Several additional batches of the MenA conjugate with an ADH linker were prepared in which the polysaccharide concentration used in the conjugation reaction with tetanus toxoid was either 12 mg/ml or 16 mg/ml. The measured values of PS/PR mass ratios for these batches were 1.0, 1.1, 1.2, and 1.3, and the measured values of O-acetylation levels in mol/mg polysaccharide were 2.5, 2.8, 2.9, and 3.0. Some values were observed more than once.

Each of the batches of MenA conjugate was confirmed to be immunogenic (i.e., elicited anti-MenA antibodies as measured by a serum bactericidal assay and/or ELISA) in at least a substantial and statistically significant fraction of recipients relative to pre-treatment samples and/or unimmunized controls) when administered in a quadrivalent formulation to MenA vaccine-naïve human, mouse, and/or guinea pig subjects.

A MenC conjugate was prepared generally as described above. The conjugate had a 0.6 polysaccharide/protein (PS/PR) mass ratio. The O-acetylation level was determined to be 2.4 µmol/mg polysaccharide. Several additional batches of the MenC conjugate were prepared. The measured values of PS/PR mass ratios for these batches were 0.4, 0.6, and 0.7, and the measured values of O-acetylation levels in mol/mg polysaccharide were 0.8, 1.2, 1.3, 1.4, 1.5, 2.2, and 2.3. Some values were observed more than once.

Each of the batches of MenC conjugate was confirmed to be immunogenic (i.e., elicited anti-MenC antibodies as measured by a serum bactericidal assay and/or ELISA in at least a substantial and statistically significant fraction of recipients relative to pre-treatment samples and/or unimmunized controls) when administered in a quadrivalent formulation to MenC vaccine-naïve human, mouse, and/or guinea pig subjects.

A MenW-135 conjugate was prepared generally as described above. The conjugate had a 0.9 polysaccharide/ protein (PS/PR) mass ratio. The O-acetylation level was determined to be 1.6 µmol/mg polysaccharide. Several additional batches of the MenW-135 conjugate were prepared. The measured values of PS/PR mass ratios for these batches were 0.6, 0.7, 0.8, 0.9, and 1.2, and the measured values of O-acetylation levels in mol/mg polysaccharide were 0.7, 0.8, and 1.3. Some values were observed more than once.

Each of the batches of MenW-135 conjugate was confirmed to be immunogenic (i.e., elicited anti-MenW-135 antibodies as measured by a serum bactericidal assay and/or ELISA in at least a substantial and statistically significant fraction of recipients relative to pre-treatment samples and/ or unimmunized controls) when administered in a quadrivalent formulation to MenW-135 vaccine-naïve human, mouse, and/or guinea pig subjects.

A MenY conjugate was prepared generally as described above. The conjugate had a 1.0 polysaccharide/protein (PS/PR) mass ratio. The O-acetylation level was determined to be 1.3 µmol/mg polysaccharide. Several additional batches of the MenY conjugate were prepared. The measured values of PS/PR mass ratios for these batches were 0.6, 0.7, 0.8, and 0.9, and the measured values of O-acetylation levels in mol/mg polysaccharide were 0.8, 0.9, 1.0, 1.1, and 1.3. Some values were observed more than once.

Each of the batches of MenY conjugate was confirmed to be immunogenic (i.e., elicited anti-MenY antibodies as measured by a serum bactericidal assay and/or ELISA in at least a substantial and statistically significant fraction of recipients relative to pre-treatment samples and/or unimmunized controls) when administered in a quadrivalent formulation to MenY vaccine-naïve human, mouse, and/or guinea pig subjects.

All conjugate batches described above were populations of conjugate molecules having a weight-average molecular weight in the range of 300 to 1500 kDa.

6. Clinical Trials

A quadrivalent MenACYW-TT conjugate as described herein was used in clinical studies to evaluate safety and immunogenicity of different vaccination schedules in infants and toddlers (6 weeks of age and older) and adults aged 56 years and older.

a) Phase I/II Clinical Trial 1—Safety and immunogenicity of various MenACYW-TT-like formulations administered to healthy meningococcal vaccine naïve toddlers (12 months+/−21 days)

This phase I/II study evaluated safety and immunogenicity of a single dose of various quadrivalent meningococcal polysaccharide-tetanus toxoid conjugate formulations related to MenACYW-TT administered intramuscularly to toddlers aged 12 months+/−21 days (groups 1-5). NeisVac-C® (fully de-O-acetylated Meningococcal Group C polysaccharide-tetanus toxoid conjugate, referred to herein as "MenC-TT", a licensed monovalent meningococcal conjugate vaccine, was administered to a control group (group 6).

Formulation 1A contained 4 µg polysaccharide of each of the four polysaccharides (i.e., MenACYW) and 22.1 µg TT per 0.5 mL dose. All had native O-acetylation levels and were conjugated via periodate activation and reductive amination (MenCYW) or using carbonyl diimidazole and adipic acid dihydrazide (MenA) essentially as described above.

Formulation 1B contained 10 µg of each of MenA and MenW polysaccharide and 4 µg of each of MenC and MenY polysaccharide and 36.6 µg TT per 0.5 mL dose. It was otherwise identical to formulation 1A.

Formulation 1C contained 10 µg of each of the four polysaccharides and 54.8 µg TT per 0.5 mL dose. It was otherwise identical to formulation 1A.

Formulation 2A contained 4 µg polysaccharide of each of the four polysaccharides and 33.9 µg TT per 0.5 mL dose. The MenC, Y, and W polysaccharides were partially de-O-acetylated by alkaline treatment, and were conjugated via periodate activation and reductive amination essentially as described above. The MenA polysaccharide had a native O-acetylation level and was made as a neoglycoconjugate using conjugation chemistry essentially as described in US2005/0002957 Example 5.

Formulation 2B contained 10 µg of each of the four polysaccharides and 84.8 µg TT per 0.5 mL dose. It was otherwise identical to formulation 2A.

All of the above formulations contained 0.67% NaCl and were buffered with sodium phosphate at pH 6.

The six study groups are summarized and characterized in Table 1.

TABLE 1

Study groups for Phase I/II clinical trial 1

| Group | n | Treatment | Per-protocol analysis population |
|---|---|---|---|
| 1 | 63 | Formulation 1A | 54 |
| 2 | 61 | Formulation 1B | 51 |
| 3 | 61 | Formulation 1C | 51 |

TABLE 1-continued

Study groups for Phase I/II clinical trial 1

| Group | n | Treatment | Per-protocol analysis population |
|---|---|---|---|
| 4 | 60 | Formulation 2A | 48 |
| 5 | 61 | Formulation 2B | 51 |
| 6 | 62 | MenC-TT | 51 |

Within treatment groups, the male-to-female ratios varied, with the extremes being 39.3% to 60.7% in Group 2, and 62.3% to 37.7% in Group 5. The age range in all groups was from 11.0 to 12.0 months; across groups, the mean ranged from 11.5 to 11.7 months.

Safety data as unsolicited adverse events (AEs) were collected up to 30-37 days after the vaccine dose. The interval for solicited AEs was between D0 and D7 (i.e., 0 to 7 days after administration). Collection of solicited reactogenicity included injection site tenderness, redness, and swelling, as well as fever, vomiting, loss of appetite, abnormal crying, drowsiness, and irritability.

All vaccinated subjects completed the study but 56 vaccinated subjects (all groups) were excluded from analysis for protocol deviations, with the most common reason being failure to provide the day 30-37 blood sample within the permitted time window.

Two subjects experienced immediate unsolicited AEs, one of which was considered related to vaccination (incidence of rash in a Group 1 subject).

Solicited Injection Site Reactions Between Day 0 and Day 7: The majority of subjects in all groups experienced solicited reactions. Overall, rates of solicited reactions were comparable between groups. The percentage of Group 1-5 recipients reporting an injection site reaction was similar to that seen with subjects who received the control vaccine (Group 6).

There was no apparent correlation between rates of injection site reactions and the amount of tetanus toxoid contained in each vaccine formulation.

The most common injection site reaction was tenderness, with rates ranging from 25.4% in Group 1 to 39.3% in Group 5; next was erythema, which ranged from 29.5% in Group 2 to 39.3% in Group 5; and the least common reaction was swelling, which ranged from 13.6% in Group 4 to 23.0% in Group 3. The majority of solicited injection site reactions were of Grade 1 intensity, began and resolved within 3 days of vaccination, and did not require any intervention. There were no group trends seen in terms of intensity, time of onset, duration, or action taken.

Solicited Systemic Reactions Between Day 0 and Day 7: As with injection site reactions, the overall rates of systemic reactions such as fever, vomiting, abnormal crying, drowsiness, lost appetite and irritability were comparable across groups 1-5 and similar to those seen with the control vaccine. The most common systemic reaction in all groups was irritability, ranging from 54.2% in Group 4 to 70.5% in both Group 2 and Group 5. The next most common (for all but Group 2) was abnormal crying, ranging from 34.4% in Group 2 to 48.4% in Group 6, followed by loss of appetite (which was the second most common reaction in Group 2), ranging from 27.9% in Group 6 to 46.8% in Group 6. Rates of vomiting ranged from 18.6% in Group 4 to 32.3% in Group 6; and fever was the least reported reaction, ranging from 11.1% in Group 1 to 25.8% in Group 6. The majority of solicited systemic reactions were of Grade 1 intensity, began and resolved within 3 days of vaccination, and did not require any intervention. There were no group trends seen in terms of intensity, time of onset, duration, or action taken.

Unsolicited Adverse Events Between Day 0 and Day 30: A total of 931 unsolicited AEs were reported in 327 subjects. A total of 107 unsolicited AEs were considered related to vaccination and were identified as adverse reactions (ARs). The most common ARs were in the SOCs of 1) general disorders and administration site conditions (25); 2) infections and infestations and skin and subcutaneous tissue disorders (20 each), and; and 3) gastrointestinal disorders and respiratory, thoracic and mediastinal disorders (16 each). There were no apparent associations between the number of ARs and the vaccine received. A total of 4 systemic ARs were reported as Grade 3 intensity: 1 each in Groups 1 and 4, and 2 in Group 5.

Serious AEs: No deaths occurred. A total of 7 SAEs occurred in 7 subjects during the study: 2 in Group 1 subjects, 1 in a Group 2 subject, 2 in Group 3 subjects, and 2 in Group 4 subjects. There were no SAEs reported in Groups 5 and 6. One of these SAEs, reactive arthritis experienced by one subject in Group 3, was deemed related to vaccination. The subject fully recovered 23 days later.

Conclusions regarding safety were that the single dose was well-tolerated in all groups and that there were no significant differences in the safety profile.

Functional antibodies to meningococcal serogroups A, C, Y, and W-135 were measured by serum bactericidal assay using human complement (SBA-HC) and baby rabbit complement (SBA-BR) to determine 1) Proportion of subjects with an SBA-HC titer 1:8 and 1:4, or an SBA-BR titer 1:8; 2) Geometric mean titers (GMTs); 3) Reverse cumulative distribution curves (RCDCs); and 4) Distribution of titers. Additionally, antibody titers to the tetanus toxoid present in the vaccines were assessed by ELISA. The assays were performed on blood samples taken pre-vaccination ("Pre" in Tables 2 and 3) and 30-37 days after vaccination ("Post" in Tables 2 and 3).

Tables 2 and 3 show the SBA-HC results. In Tables 2 and 3, 95% confidence intervals are percentages.

TABLE 2

Number and Percentage of Subjects with a Titer ≥ 1:8 at Baseline and Post-vaccination, SBA-HC Assay (Per-Protocol Population)

| Serogroup | Time point | Group 1 (N = 54) n/M; % 95% CI | Group 2 (N = 51) n/M; % 95% CI | Group 3 (N = 51) n/M; % 95% CI | Group 4 (N = 48) n/M; % 95% CI | Group 5 (N = 51) n/M; % 95% CI | Group 6 (N = 51) n/M; % 95% CI |
|---|---|---|---|---|---|---|---|
| A | Pre | 19/54; 35.2 (22.7; 49.4) | 11/51; 21.6 (11.3; 35.3) | 15/50; 30.0 (17.9; 44.6) | 9/48; 18.8 (8.9; 32.6) | 16/51; 31.4 (19.1; 45.9) | 13/51; 25.5 (14.3; 39.6) |
|   | Post | 47/54; 87.0 (75.1; 94.6) | 50/50); 100.0 | 45/51; 88.2 (76.1; 95.6) | 36/48; 75.0 (60.4; 86.4) | 47/51; 92.2 (81.1; 97.8) | 23/50; 46.0 (31.8; 60.7) |

TABLE 2-continued

Number and Percentage of Subjects with a Titer ≥ 1:8 at Baseline and Post-vaccination, SBA-HC Assay (Per-Protocol Population)

| Serogroup | Time point | Group 1 (N = 54) n/M; % 95% CI | Group 2 (N = 51) n/M; % 95% CI | Group 3 (N = 51) n/M; % 95% CI | Group 4 (N = 48) n/M; % 95% CI | Group 5 (N = 51) n/M; % 95% CI | Group 6 (N = 51) n/M; % 95% CI |
|---|---|---|---|---|---|---|---|
| | | (92.9; 100.0) | | | | | |
| C | Pre | 0/54; 0.0 (0.0; 6.6) | 0/51; 0.0 (0.0; 7.0) | 0/51; 0.0 (0.0; 7.0) | 1/48; 2.1 (0.1; 11.1) | 0/51; 0.0 (0.0; 7.0) | 0/51; 0.0 (0.0; 7.0) |
| | Post | 49/54; 90.7 (79.7; 96.9) | 44/51; 86.3 (73.7; 94.3) | 43/51; 84.3 (71.4; 93.0) | 45/48; 93.8 (82.8; 98.7) | 49/51; 96.1 (86.5; 99.5) | 51/51; 100.0 (93.0; 100.0) |
| Y | Pre | 1/54; 1.9 (0.0; 9.9) | 2/51; 3.9 (0.5; 13.5) | 1/51; 2.0 (0.0; 10.4) | 0/48; 0.0 (0.0; 7.4) | 0/51; 0.0 (0.0; 7.0) | 3/51; 5.9 (1.2; 16.2) |
| | Post | 36/54; 66.7 (52.5; 78.9) | 40/51; 78.4 (64.7; 88.7) | 40/51; 78.4 (64.7; 88.7) | 44/48; 91.7 (80.0; 97.7) | 42/51; 82.4 (69.1; 91.6) | 4/51; 7.8 (2.2; 18.9) |
| W-135 | Pre | 0/54; 0.0 (0.0; 6.6) | 0/51; 0.0 (0.0; 7.0) | 0/51; 0.0 (0.0; 7.0) | 0/48; 0.0 (0.0; 7.4) | 0/51; 0.0 (0.0; 7.0) | 0/51; 0.0 (0.0; 7.0) |
| | Post | 35/54; 64.8 (50.6; 77.3) | 35/50; 70.0 (55.4; 82.1) | 33/51; 64.7 (50.1; 77.6) | 30/48; 62.5 (47.4; 76.0) | 36/51; 70.6 (56.2; 82.5) | 1/50; 2.0 (0.1; 10.6) |

TABLE 3

Geometric Mean Titers (GMTs) at Baseline and Post-Vaccination, SBA-HC Assay (Per-Protocol Population)

| Antigen | Time point | Group 1 (N = 54) GMT (95% CI) | Group 2 (N = 51) GMT (95% CI) | Group 3 (N = 51) GMT (95% CI) | Group 4 (N = 48) GMT (95% CI) | Group 5 (N = 51) GMT (95% CI) | Group 6 (N = 51) GMT (95% CI) |
|---|---|---|---|---|---|---|---|
| A | Pre | 4.79 (3.75; 6.11) | 3.84 (3.12; 4.73) | 4.17 (3.35; 5.19) | 3.83 (3.07; 4.78) | 4.77 (3.59; 6.35) | 3.84 (3.11; 4.74) |
| | Post | 21.22 (14.85; 30.33) | 41.64 (30.30; 57.24) | 29.10 (20.18; 41.95) | 14.89 (10.54; 21.03) | 29.10 (21.30; 39.75) | 6.87 (5.10; 9.26) |
| C | Pre | 2.00 (2.00; 2.00) | 2.03 (1.97; 2.08) | 2.03 (1.97; 2.08) | 2.06 (1.94; 2.18) | 2.00 (2.00; 2.00) | 2.08 (1.99; 2.18) |
| | Post | 60.80 (37.71; 98.01) | 46.19 (29.29; 72.82) | 73.32 (42.18; 127.43) | 131.75 (80.90; 214.56) | 252.54 (170.84; 373.32) | 471.91 (373.90; 595.60) |
| Y | Pre | 2.08 (1.96; 2.20) | 2.14 (1.94; 2.36) | 2.20 (1.86; 2.60) | 2.00 (2.00; 2.00) | 2.00 (2.00; 2.00) | 2.32 (1.96; 2.76) |
| | Post | 13.89 (9.19; 21.00) | 17.36 (11.50; 26.21) | 23.73 (14.86; 37.90) | 26.52 (18.61; 37.79) | 26.46 (17.29; 40.49) | 2.42 (2.09; 2.80) |
| W-135 | Pre | 2.03 (1.97; 2.08) | 2.00 (2.00; 2.00) | 2.03 (1.97; 2.08) | 2.03 (1.97; 2.09) | 2.03 (1.97; 2.08) | 2.00 (2.00; 2.00) |
| | Post | 10.21 (7.32; 14.25) | 13.00 (8.59; 19.66) | 16.00 (9.74; 26.28) | 10.53 (7.10; 15.60) | 15.57 (10.56; 22.95) | 2.17 (2.01; 2.34) |

As can be seen from the tables, pre-vaccination titers were low for all serogroups. For serogroup A, the majority of subjects in all groups had titers of 8 or less; for the other three serogroups, virtually all subjects had values <4. In groups 1-5 post-vaccination, for serogroup A, the majority of titer values were between 8 and 128; for serogroup C, between 16 and 1024; for serogroup Y, between <4 and 128; and for serogroup W-135, between <4 and 64. For the control group, values for serogroups A, Y, and W-135 were mostly between <4 and 4, while for serogroup C, most values were between 256 and 1024. There was a trend toward higher antibody responses in the high-dose groups compared to the low-dose groups.

In the SBA-BR assays, pre-dose GMTs were comparable across treatment groups, ranging from 4.22 to 5.26 for serogroup A; from 4.00 to 6.26 for serogroup C; and from 6.01 to 8.45 for serogroup W-135. There was more variability seen in serogroup Y, whose values ranged from 17.36 (Group 5) to 35.92 (Group 1).

In groups 1-5, the post-vaccination values ranged from 336.91 (Group 1) to 759.35 (Group 5) for serogroup A; the value for the control group was 5.66. Values for serogroup C ranged from 145.53 (Group 1) to 636.37 (Group 5). The value for the control group was 1290.16. Values for serogroup Y ranged from 586.54 (Group 3) to 713.70 (Group 4). The value for the control group was 23.41. Values for serogroup W-135 ranged from 912.28 (Group 4) to 1518.71 (Group 5). The value for the control group was 8.57.

b) Phase II Clinical Trial 1—Safety and Immunogenicity of MenACYW-TT in Infants and Toddlers A Phase II, randomized, open-label, multicenter clinical trial was conducted in 580 children in the United States. The trial was designed to study the safety and immunogenicity profiles of the MenACYW-TT vaccine administered at different schedules and concomitantly with routine pediatric vaccinations. The study also aimed to describe the immunogenicity profiles of MenACYW-TT vaccine and selected licensed pediatric vaccines (Pentacel® (DTaP-IPV/Hib), Prevnar® (PCV7) or Prevnar® 13 (PCV13), M-M-R® II (MMR) Varivax® (V), ENGERIX-B® or RECOMBIVAX HB® (HepB), Rotarix® (RV1), and Rotateq® (RV5) when administered concomitantly with the MenACYW-TT vaccine.

Participants received either MenACYW-TT vaccine concomitantly with routine vaccines (investigational groups; Groups 1-5 from Table 1) or received routine pediatric vaccines alone (control groups; Groups 6-7).

Two-month-old infants were randomly assigned to 3 investigational groups (Groups 1-3) and 2 control groups (Groups 6 and 7), as shown in Table 1. Infants in the investigational Groups 1-3 received either 3 or 4 doses of MenACYW-TT vaccine (concomitantly with routine vaccines) as described in Table 4.

Table 4 provides a summary of the design of the clinical trial.

Six-month-old infants who received 2 doses of MenACYW-TT vaccine (concomitantly with routine vaccines) at 6 and 12 months of age (Group 4), and 12-month-olds who received 1 dose of MenACYW-TT vaccine (concomitantly with routine vaccines) at 12 months of age (Group 5) were also enrolled.

Serum bactericidal assays with human (hSBA) and baby rabbit (rSBA) complement were used to measure antibodies against meningococcal serogroups A, C, Y, and W at baseline and 30 days after the last infant and the toddler doses. The lower limit of quantification (LLOQ) of both assays was 1:4. See, e.g., Maslanka et al, Standardization and a Multilaboratory Comparison of *Neisseria meningitidis* Serogroup A and C Serum Bactericidal Assays, Clinical and Diagnostic Laboratory Immunology, March 1997, p. 156-167, and Goldschneider Gotschlich, and Artenstein, Immunity to Meningococcus, The Role of Humoral Antibodies, the Journal of Experimental Medicine, 1969.

TABLE 4

Study design and vaccines received in this clinical trial

| | Trial Schedule (Age) | | | | |
| --- | --- | --- | --- | --- | --- |
| Group | 2 months | 4 months | 6 months | 12 months | 15 months |
| 1 | MenACYW-TT, DTaP-IPV/Hib, PCV7 or PCV13, RV1 or RV5, HepB[1] | MenACYW-TT, DTaP-IPV/Hib, PCV7 or PCV13, RV1 or RV5 | MenACYW-TT, DTaP-IPV/Hib, PCV7 or PCV13, RV5[2], HepB | MenACYW-TT, MMR, V, PCV7 or PCV13 | |
| 2 | MenACYW-TT, DTaP-IPV/Hib, PCV7 or PCV13, RV1 or RV5, HepB[1] | MenACYW-TT, DTaP-IPV/Hib, PCV7 or PCV13, RV1 or RV5 | MenACYW-TT, DTaP-IPV/Hib, PCV7 or PCV13, RV5[2], HepB | MMR, V, PCV7 or PCV13 | MenACYW-TT, DTaP-IPV/Hib |
| 3 | MenACYW-TT, DTaP-IPV/Hib, PCV7 or PCV13, RV1 or RV5, HepB[1] | MenACYW-TT, DTaP-IPV/Hib, PCV7 or PCV13, RV1 or RV5 | DTaP-IPV/Hib, PCV7 or PCV13, RV5[2], HepB | MenACYW-TT, MMR, V, PCV7 or PCV13 | |
| 4 | | | MenACYW-TT, DTaP-IPV/Hib, PCV7 or PCV13, RV5[2], HepB | MenACYW-TT, MMR, V, PCV7 or PCV13 | |
| 5 | | | | MenACYW-TT, MMR, V, PCV7 or PCV13 | |
| 6 | DTaP-IPV/Hib, PCV7 or PCV13, RV1 or RV5, HepB[1] | DTaP-IPV/Hib, PCV7 or PCV13, RV1 or RV5 | DTaP-IPV/Hib, PCV7 or PCV13, RV5[2], HepB | MMR, V, PCV7 or PCV13 | |
| 7 | DTaP-IPV/Hib, PCV7 or PCV13, RV1 or RV5, HepB[1] | DTaP-IPV/Hib, PCV7 or PCV13, RV1 or RV5 | DTaP-IPV/Hib, PCV7 or PCV13, RV5[2], HepB | MMR, V, PCV7 or PCV13 | DTaP-IPV/Hib |

[1]If only one previous dose given;
[2]If previous vaccinations with RV5

Safety data were collected up to 6 months after last dose of vaccines. The interval for solicited adverse events (AEs) was between D0 and D7 (i.e., 0 to 7 days after administration). Collection of solicited reactogenicity included daily measurement of body temperature and injection site redness and swelling, as well as recording of the intensity for injection site pain, headache, myalgia and malaise. Unsolicited AEs and Serious Adverse Events (SAEs) were also collected throughout the study. All statistical analyses were descriptive.

Demographics were analyzed for the safety analysis set, which was defined as subjects who received at least one dose of study or control vaccine and for whom safety data were available. Mean age at study inclusion in Groups 1, 2, 3, 6, and 7 was 2.19, 2.20, 2.24, 2.18, and 2.20 months, respectively. The age range was 1.57 to 2.97 months in Group 1, 1.57 to 2.90 months in Group 2, 1.53 to 3.00 months in Group 3, 1.53 to 2.87 months in Group 6, and 1.70 to 2.97 months in Group 7 (inclusion criteria 2 months [42 to 89 days]). In Group 4, the mean age was 6.23 months and the age range was 5.63 months to 6.50 months (inclusion criteria 6 months [180 days±14 days]). In Group 5, the mean age was 12.4 months and the age range was 12.2 to 12.7 months (inclusion criteria 12 months [365 days+14 days]).

After completing the infant series and receiving an additional MenACYW-TT vaccine dose in the second year of life (Groups 1-4) most study participants achieved protective titers of 1:8 (91%-100% for human complement [hSBA] and 80%-100% for baby rabbit complement [rSBA]) for all 4 serogroups (ACYW) included in the MenACYW-TT vaccine, regardless of the number of doses received during the first year of life. For participants who received a single dose at 12 months of age (Group 5), ACYW protective titers of 1:8 were between 47.5%-90% (hSBA) and 62%-100% (rSBA). Thus, the MenACYW-TT conjugate vaccine demonstrates a robust immunogenic response after an additional dose in the second year of life, regardless of the primary schedule received in first year of life.

FIG. 6 provides percentage of subjects with hSBA levels greater than or equal to 1:8 for each of serotype A, C, Y, and W for Groups 1-4. FIG. 7 provides similar rSBA results for these same groups.

The immune responses to hSBA after a single dose of MenACYW-TT vaccine administered at 12 months of age (Group 5) were similar to the responses seen in the 3-dose series (Group 3) for serogroup C (90%) but lower for serogroups Y (47.5%), A (75%) and W-135 (54%). See Table 5, which shows hSBA and rSBA titers for subjects who received a single MenACYW-TT vaccine dose at 12-months-of-age (Group 5).

TABLE 5

Percentage of subjects achieving hSBA & rSBA titers ≥ 1:8 at D30 after MenACYW-TT vaccine (subjects who just received one dose in second year of life)

| | Percentage of Subjects achieving Serum Bactericidal Assay Titers ≥ 1:8 | |
|---|---|---|
| Serogroups | Human Complement (hSBA) % (9.5% CI) | Baby Rabbit Complement (rSBA) % (9.5% CI) |
| A | 74.6 (61.6; 85.0) | 62.1 (48.4; 74.5) |
| C | 90.2 (79.8; 96.3) | 91.4 (81.0; 97.1) |
| Y | 47.5 (34.6; 60.7) | 94.8 (85.6; 98.9) |
| W | 54.2 (40.8; 67.3) | 100.0 (93.8; 100.0) |

D: day; CI: confidence interval

There was no evidence of interference with the pediatric routine vaccines administered concomitantly with MenA-CYW-TT vaccine (data not shown).

The frequency of solicited injection site reactions did not increase with repeated vaccine doses. See, FIG. 8, which presents the cumulative percentage of participants who reported one or more solicited injection site reaction within 7 days of administration of MenACYW-TT vaccine. The cumulative percentage of participants who reported ≤1 solicited injection site reaction within 7 days following MenA-CYW-TT vaccine administration was highest in the groups that received 4 doses (Groups 1 and 2, 80.0%/–80.8%), followed by the groups that received 2 doses (Group 4, 75.3%) or 3 doses (Group 2, 74.0%) doses, and was lowest in the group that received 1 dose (Group 5, 57.4%).

FIG. 9 shows solicited systemic reactions within 7 days of administration of either MenACYW-TT vaccine plus routine vaccines or routine vaccines alone.

Mostly non-serious adverse events (NSAEs) were reported after vaccinations with either MenACYW-TT vaccine or routine vaccines, and each of the reported Grade 3 NSAEs were unrelated to the study vaccines. There were no vaccine-related serious adverse events.

Both the MenACYW-TT vaccine and the routine vaccines were immunogenic when given concomitantly (i.e., on the same day, as separate vaccines), as compared to when the routine vaccines were given without MenACYW-TT vaccine in the control groups, indicating that there was no negative interaction between the MenACYW-TT vaccine and routine vaccines.

In summary, the MenACYW-TT vaccine was safe and well tolerated in infants and toddlers regardless of the immunization schedule and the number of doses administered. The safety profile of MenACYW-TT vaccine is similar overall to that in the control groups, regardless of the immunization schedule and the number of doses administered.

Thus, the investigational MenACYW-TT vaccine was well tolerated and immunogenic. All vaccination schedules that included dose(s) in both the first and second year of life induced robust immune responses for all 4 vaccine *N. meningitidis* serogroups A, C, Y, and W, and were accompanied by an acceptable safety profile.

c) Phase II Clinical Trial 2—Safety and immunogenicity of MenACYW-TT administered to adults 56 years of age and older.

Age and underlying chronic illnesses are important risk factors for meningococcal disease, so older adults are at increased risk. A clinical study was performed to evaluate the safety and immunogenicity of the MenACYW-TT vaccine as compared to Menomune®-A/C/Y/W-135, a licensed quadrivalent meningococcal plain polysaccharide vaccine (MPSV4) in adults 56 years of age or older.

A Phase II, randomized, open-label, multicenter study was conducted in 301 healthy adults greater than or equal to 56 years of age in the United States. Participants at 12 study sites were randomly assigned to receive one dose of either MenACYW-TT or MPSV4 (Menomune®—A/C/Y/W-135). Patients were stratified according to age into 2 subsets: 1) 56 to 64 years and 2) greater than or equal to 65 years.

Four study groups were formed as follows. Group 1a (n=101, ages 56-64 years) and Group 1b (n=100, ≥65 years) received MenACYW-TT. Group 2a (n=50, ages 56-64 years) and Group 2b (n=50, ≥65 years) received the MPSV4 vaccine. "Group 1" will refer to Group 1a plus Group 1b. "Group 2" will refer to Group 2a plus Group 2b. The demographic results are summarized in Table 6.

TABLE 6

Study design and vaccines received in this clinical trial

| Study group (number of study participants) | Vaccine received (age range of study participants) |
|---|---|
| Group 1a (n = 101) | MenACYW-TT (56-64 years) |
| Group 1b (n = 100) | MenACYW-TT (≥65 years) |
| Group 2a (n = 50) | MPSV4 (56-64 years) |
| Group 2b (n = 50) | MPSV4 (≥65 years) |

Serum bactericidal assays (SBA) with human complement (hSBA) and baby rabbit complement (rSBA), as described in above, were used to measure antibodies against meningococcal serogroups A, C, Y, and W at baseline and 30 days after vaccine administration. The lower limit of quantification (LLOQ) for both assays was 1:4.

Safety data were collected up to 30 days after administration. The interval for solicited AEs was between D0 and D7 (i.e., 0 to 7 days after administration). Collection of solicited reactogenicity included daily measurement of body temperature and injection site redness and swelling, as well as recording of the intensity for injection site pain, headache, myalgia and malaise. Unsolicited AEs and Serious Adverse Events (SAEs) were also collected throughout the study. All statistical analyses were descriptive.

Demographics were analyzed for the safety analysis set, which was defined as subjects who received at least one dose of study or control vaccine and for whom safety data were available. At enrollment, the mean age of subjects was similar in both Group 1 and Group 2 (66.1±7.13 years, and 65.8±6.58 years, respectively). Additionally, ages were similar for the groups having subjects of 56-64 years and those having subjects of ≥65 years (60.3±2.52 years in Group 1a, 60.8±2.59 years in Group 2a, 71.9±5.28 years in Group 1b, and 70.8±5.45 years in Group 2b).

In both Group 1 and Group 2, there were slightly more female subjects (60.8% [121/199] and 55.0% [55/100], respectively) than male subjects (39.2% [78/199] and 45.0% [45/100], respectively). The same tendency was observed in the subsets, with the exception of Group 2b where there were equal numbers of female and male subjects (50.0% [25/50]).

The percentages of study participants with hSBA titers 1:8 against serogroups A, C, Y, and W-135 were markedly increased at Day 30 compared to baseline for all subgroups. In the two age substrata (56 to 64 years of age and 65 years of age) results were overall similar within each vaccination group as shown in Table 7.

TABLE 7

Percentage of subjects achieving hSBA titers ≥ 1:8 at D30

| Serogroups | Group 1a MenACYW-TT (56y-64y) (N = 98) % (95% CI) | Group 1b MenACYW-TT (≥6.5y) (N = 97) % (95% CI) | Group 2a MPSV4 (56y-64y) (N = 46) % (95% CI) | Group 2b MPSV4 (≥6.5y) (N = 48) % (95% CI) |
|---|---|---|---|---|
| A | 95.9 (89.9; 98.9) | 91.8 (84.4; 96.4) | 78.3 (63.6; 89.1) | 91.7 (80.0; 97.7) |
| C | 71.4 (61.4; 80.1) | 78.4 (68.8; 86.1) | 58.7 (43.2; 73.0) | 66.7 (51.6; 79.6) |
| Y | 81.6 (72.5; 88.7) | 79.4 (70.0; 86.9) | 60.9 (45.4; 74.9) | 58.3 (43.2; 72.4) |
| W | 77.6 (68.0; 85.4) | 81.4 (72.3; 88.6) | 58.7 (43.2; 73.0) | 62.5 (47.4; 76.0) |

D: day; CI: confidence interval

FIG. 10 provides the percentage of subjects achieving hSBA levels ≥1:8 at D30 for serogroup A, C, Y, and W using data from all patients (i.e., combined age groups). The percentage of individuals with hSBA titers ≥1:8 after MenACYW-TT administration was comparable to titers after MPSV4 administration for serogroups A and C. The percentage of individuals with hSBA titers ≥1:8 after MenACYW-TT administration was higher than titers after MPSV4 administration for serogroups Y and W.

FIG. 11 provides the geometric mean titers (GMTs) for different serogroups at D30 for both vaccines. GMTs with the MenACYW-TT were greater or equal to GMTs with MPSV4 for all serogroups.

Percentages of participants with rSBA titers greater than or equal to 1:8 were comparable between MenACYW-TT recipients and MPSV4 recipients for all four vaccine groups. See, FIG. 12.

Solicited injection site reactions (FIG. 13) and solicited systemic reactions (FIG. 14) within 7 days of administration of the MenACYW-TT were similar to those for the MPSV4 vaccine.

Overall, the reactogenicity profile for both the MenACYW-TT and the MPSV4 vaccine was similar. Most unsolicited adverse events were of Grade 1 or Grade 2 intensity. There were no immediate hypersensitivity reactions and no discontinuations due to AEs or SAEs. No increase in reactogenicity in older vaccine recipients was observed. No serious adverse events were reported.

MenACYW-TT was well-tolerated and immunogenic when administered to adults 56 years of age or older. Therefore, MenACYW-TT represents an alternative vaccine for the prevention of invasive meningococcal disease, including in areas of the world where only plain polysaccharide vaccines, such as MPSV4, are currently available for immunization of older adults.

d) Phase II Clinical Trial 3—Safety and Immunogenicity of MenACYW-TT Administered to Healthy Meningococcal Vaccine Naïve Toddlers (12-23 Months)

MenACYW-TT conjugate vaccine is intended for use in individuals 6 weeks of age and older. This study evaluated safety and immunogenicity of a single dose in toddlers using Nimenrix®, a licensed quadrivalent meningococcal conjugate vaccine (MCV4-TT) as control.

A Phase II, randomized, open-label study in 188 meningococcal vaccine-naïve toddlers (12-23 months of age) was conducted in Finland. Participants were randomly assigned to receive one dose of either MenACYW-TT vaccine or MCV4-TT. Serum bactericidal assays with human (hSBA) and baby rabbit (rSBA) complement were used to measure antibodies against meningococcal serogroups A, C, W and Y at baseline and 30 days after the dose. The LLOQ of both bactericidal assays was 1:4. Antibody responses against tetanus were also measured.

Safety data were collected up to 30 days after the dose. The interval for solicited adverse events (AEs) was between D0 and D7. Collection of solicited reactogenicity included daily measurement of body temperature and injection site redness and swelling, as well as recording of the intensity for injection site pain, headache, myalgia and malaise. Unsolicited AEs and serious adverse events (SAEs) were collected throughout the study. All analyses were descriptive.

Table 8 provides data on study design and subject disposition of the trial.

TABLE 8

Study design and subject disposition

| | MenACYW-TT Conjugate Vaccine, n (%) | MCV4-TT Control Vaccine, n (%) | All Subjects, n (%) |
|---|---|---|---|
| Planned Sample size | 100 | 100 | 200 |
| Enrolled Subjects | 94 (100%) | 94 (100%) | 188 (100%) |
| Randomized Subjects | 94 (100%) | 94 (100%) | 188 (100%) |
| Subjects who completed the study | 94 (100%) | 94 (100%) | 188 (100%) |
| Discontinued Subjects | 0 (0.0%) | 0 (0.0%) | 0 (0.0%) |
| Per Protocol Analysis Set | 91 (96.8%) | 86 (91.5%) | 177 (94.1%) |

A demographic analysis was done on the safety analysis set. The safety analysis set was defined as subjects who received at least one dose of study or control vaccine and for whom safety data were available. There were a total of 98 (52.1%) male subjects and 90 (47.9%) female subjects in the safety analysis set; the overall ratio of male/female subjects was 1.09. There were more males than females in MenACYW-TT Group (male/female ratio was 1.54). There were more females than males in the MCV4-TT Group (male/female ratio was 0.77). Subjects' ages were comparable across the 2 groups. The mean age of the subjects at enrollment was 1.44±0.302 years in the MenACYW-TT group and 1.47±0.314 years in the MCV4-TT group.

The percentage of subjects with hSBA vaccine seroresponse with MenACYW-TT vaccine was comparable to that with MCV4-TT for serogroups A, W and Y [range 96.7% to 98.9% (MenACYW-TT) and 91.9% to 98.8% (MCV4-TI)] (FIG. 15). hSBA vaccine seroresponse was defined as follows: if titer was <1:8 at baseline with post-vaccination titer ≥1:8 or if titer was 1:8 at baseline with a ≥4-fold increase at post-vaccination.

The percentage of subjects with seroresponse for serogroup C was higher with MenACYW-TT (100.0%) than with MCV4-TT (86.0%). The trend for serogroup C was similar using rSBA.

Data on the percentage of subjects achieving hSBA titers >=8 (>=1:8) at D30 after vaccine are presented in Table 9.

TABLE 9

Percentage of patients achieving hSBA titers of ≥ 8

| | Percentage of Subjects achieving Human Serum Bactericidal Assay Titers ≥ 8 % (95% CI) | |
|---|---|---|
| Serogroups | MenACYW-TT | MCV4-TT |
| A | 97.8 (92.3; 99.7) | 91.9 (83.9; 96.7) |
| C | 100.0 (96.0; 100.0) | 89.5 (81.1; 95.1) |

TABLE 9-continued

Percentage of patients achieving hSBA titers of ≥ 8

| | Percentage of Subjects achieving Human Serum Bactericidal Assay Titers ≥ 8 % (95% CI) | |
|---|---|---|
| Serogroups | MenACYW-TT | MCV4-TT |
| W | 98.9 (94.0; 100.0) | 96.5 (90.1; 99.3) |
| Y | 98.9 (94.0; 100.0) | 100.0 (95.8; 100.0) |

MenACYW-TT elicited comparable immune responses to serogroups A, W and Y and higher for serogroup C, when evaluated using hSBA geometric mean titers and percentage of subjects having post-vaccination hSBA titers 28 (1:8) (FIG. 16 and Table 10). FIG. 16 and Table 10 show the same data, except the data in Table 10 is converted to log 2 scale as shown in FIG. 16.

TABLE 10

| | Post-vaccination hSBA geometric mean titers | |
|---|---|---|
| | MenACYW-TT | MCV4-TT |
| A | 76.8 | 61.5 |
| C | 492.9 | 28.4 |
| W | 71.7 | 44.5 |
| Y | 96.6 | 76.4 |

Safety was also evaluated in the study. Reactogenicity profile was comparable between both vaccines. The percentages of subjects reporting at least 1 solicited injection site reaction were comparable between both vaccines (48.9% and 53.2%). Data on erythema, tenderness, and swelling at the injection site are shown in FIG. 17. The majority of reactions at the injection sites were of Grade 1 or 2 intensity, all started between D0 and D03, and most lasted 1 to 3 days.

Few subjects reported Grade 3 solicited injection site reactions: 3.2% of subjects in the MenACYW-TT Group and 4.3% of subjects in the MCV4-TT Group.

Solicited system reactions were also similar between the two groups (FIG. 18).

The percentages of subjects reporting at least 1 unsolicited non-serious AE were comparable between the study groups. Most unsolicited adverse events were of Grade 1 or Grade 2 intensity. There were no immediate unsolicited AEs reported in either of the groups. There were no immediate SAEs, including any anaphylactic or life-threatening events. Two serious adverse events reported were considered as unrelated.

The investigational MenACYW-TT vaccine was well tolerated and immunogenic. Single dose of the MenACYW-TT vaccine demonstrated excellent potential to be an alternative vaccine option for toddlers receiving meningococcal vaccination for the first time.

e) Phase II Clinical Trial 4—Safety and Immunogenicity of MenACYW-TT Administered to Healthy Meningococcal Vaccine Naïve Adolescents (10-18 Years)

This phase II study evaluated safety and immunogenicity of a single dose (10 µg polysaccharide per serogroup, conjugated to 65 µg TT total, in 0.67% NaCl/30 mM sodium acetate buffered at pH 6.0) of MenACYW-TT administered intramuscularly to adolescents aged 10-18 years. Menveo® (Meningococcal (Groups A, C, Y and W-135) Oligosaccharide Diphtheria CRM197 Conjugate Vaccine, referred to herein as "MenACYW-CRM$_{197}$", a licensed quadrivalent meningococcal conjugate vaccine, was administered to a control group (group 2). The effect of coadministering MenACYW-TT with Tdap/Adacel® and HPV/Gardasil® (group 3) was also compared to administration of Tdap/Adacel® and HPV/Gardasil® alone (group 4). The control vaccine and Tdap/Adacel® and HPV/Gardasil® vaccines were administered according to label instructions. The four study groups are summarized and characterized in Table 11.

TABLE 11

Study groups for clinical trial 4

| Group | n | Treatment | Males | Females | Mean, Median age (yrs) |
|---|---|---|---|---|---|
| 1 | 503 | MenACYW-TT | 243 | 260 | 11.4, 11.1 |
| 2 | 501 | MenACYW-CRM197 | 272 | 229 | 11.4, 11.2 |
| 3 | 392 | MenACYW-TT with Tdap/Adacel ® and HPV*/Gardasil ® | 201 | 191 | 11.3, 11.1 |
| 4 | 155 | Tdap/Adacel ® and HPV*/Gardasil ® | 155 | 141 | 11.4, 11.1 |

*First dose of HPV vaccine was given on D0; HPV Dose 2 and Dose 3 were given 2 and 6 months, respectively, after Dose 1.

A total of 74 subjects (4.3%) did not complete the trial: 10 (2.0%) in Group 1, 7 (1.4%) in Group 2, 27 (6.7%) in Group 3, and 30 (10.0%) in Group 4. The most frequently reported reasons for discontinuation were: voluntary withdrawal not due to an adverse event, lost to follow-up, and non-compliance with the protocol. There were no early terminations due to an SAE or other AE.

Serum bactericidal assays with human complement (hSBA) were used to measure antibodies against meningococcal serogroups A, C, W and Y at baseline and 30 days after the dose. The LLOQ of the bactericidal assays was 1:4. hSBA data were collected for 463 members of group 1, 464 members of group 2, and 360 members of group 3. hSBA results are in Table 12, in which % subjects indicate the percentage of subjects with a positive seroresponse, i.e., post vaccination hSBA 1:8 for subjects with pre-vaccination hSBA titers <1:8, or at least a 4-fold increase in hSBA titers from pre to post-vaccination for subjects with pre-vaccination titers 1:8. A greater percentage of subjects showed a positive seroresponse with MenACYW-TT than with MenACYW-CRM$_{197}$ for all four serogroups.

TABLE 12 hSBA Results for Phase II Clinical Trial 4

| | Group 1 (MenACYW-TT) (N = 463) | | Group 2 (MenACYW-CRM$_{197}$) (N = 464) | | Group 3 (MenACYW-TT + Tdap + HPV (N = 360) | |
|---|---|---|---|---|---|---|
| Serogroup | % subjects | 95% CI | % subjects | 95% CI | % subjects | 95% CI |
| A | 75.6 | 71.4; 79.4 | 66.4 | 61.9; 70.7 | 80.6 | 76.1; 84.5 |
| C | 97.2 | 95.2; 98.5 | 72.6 | 68.3; 76.6 | 97.2 | 95.0; 98.7 |
| Y | 97.0 | 95.0; 98.3 | 80.8 | 76.9; 84.3 | 95.6 | 92.9; 97.4 |
| W | 86.2 | 82.7; 89.2 | 66.6 | 62.1; 70.9 | 83.9 | 79.7; 87.5 |

The difference in seroresponse frequency between groups 1 and 2 is shown in Table 13 along with the 95% confidence interval thereof.

TABLE 13

Group 1-Group 2 differential seroresponse

| Serogroup | Difference (% subjects) | 95% CI |
|---|---|---|
| A | 9.2 | 3.4; 15.0 |
| C | 24.6 | 20.3; 29.0 |
| Y | 16.2 | 12.3; 20.2 |
| W | 19.6 | 14.2; 24.8 |

The difference in seroresponse frequency between groups 1 and 3 was not significant at 95% confidence, consistent with the conclusion that MenACYW-TT efficacy is not affected by coadministration with Tdap/Adacel® and HPV/Gardasil®.

Table 14 shows hSBA results expressed as geometric mean titers (GMT) at day 0 (D0) and day 30 (D30), along with 95% confidence intervals.

TABLE 14 hSBA Geometric Mean Titers

| Serogroup | | Group 1 (N = 463) | | Group 2 (N = 464) | | Group 3 (N = 360) | |
|---|---|---|---|---|---|---|---|
| | | GMT | 95% CI | GMT | 95% CI | GMT | 95% CI |
| A | D0 | 6.19 | 5.62; 6.83 | 5.75 | 5.24; 6.31 | 5.34 | 4.8; 5.94 |
| | D30 | 44.1 | 39.2; 49.6 | 35.2 | 30.3; 41.0 | 47.9 | 41.7; 55.0 |
| C | D0 | 3.36 | 3.12; 3.62 | 3.08 | 2.88; 3.30 | 3.38 | 3.13; 3.64 |
| | D30 | 387 | 329; 456 | 51.4 | 41.2; 64.2 | 335 | 280; 399 |
| Y | D0 | 2.33 | 2.23; 2.43 | 2.41 | 2.28; 2.54 | 2.46 | 2.32; 2.62 |
| | D30 | 75.7 | 66.2; 86.5 | 27.6 | 23.8; 32.1 | 77.3 | 66.5; 89.9 |
| W | D0 | 5.17 | 4.67; 5.73 | 5.35 | 4.82; 5.94 | 5.87 | 5.22; 6.60 |
| | D30 | 86.9 | 77.8; 97 | 36.0 | 31.5; 41.0 | 91 | 80.2; 103 |

Immune responses to diphtheria and tetanus were compared for all groups. Results are shown in Table 15, expressed as geometric mean concentration (GMC); % subjects with ≥0.1 IU/mL; and % subjects with ≥1.0 IU/mL of the anti-tetanus and anti-diphtheria antibody concentrations.

TABLE 15

Post-vaccination geometric means and titers for Diphtheria and Tetanus

| | Diphtheria | | | Tetanus | | |
|---|---|---|---|---|---|---|
| | GMC | ≥0.1 IU/mL (%) | ≥1.0 IU/mL (%) | GMC | ≥0.1 IU/mL (%) | ≥1.0 IU/mL (%) |
| Group 1 (N = 463) | 0.152 | 57.4 | 7.4 | 21.4 | 100 | 97.9 |
| Group 2 (N = 464) | 35.4 | 100 | 98.9 | 0.346 | 90.1 | 18.7 |
| Group 3 (N = 360) | 11.9 | 99.4 | 97.8 | 29.0 | 99.7 | 99.7 |
| Group 4 (N = 263) | 15.7 | 99.6 | 98.9 | 14.7 | 100 | 99.6 |

Results were consistent with the conclusion that coadministration of MenACYW-TT with Tdap/Adacel® as i group 3 did not interfere with the immunogenicity of the latter (cf. group 4 results).

Vaccine responses were also characterized with respect to the following antigens: pertussis toxin (PT), pertussis filamentous hemagglutinin (FHA), pertussis pertactin (PRN) and pertussis fimbrial antigen (FIM). See Table 16.

TABLE 16

Responses to PT, FHA, PRN and FIM antigens.

| | Group 3 (N = 360) | | | Group 4 (n = 263) | | |
|---|---|---|---|---|---|---|
| Ag | GMT/GMC | 95% CI | Vaccine Response (%) | GMT/GMC | 95% CI | Vaccine Response (%) |
| PT | 37.5 | 33.8; 41.7 | 67.3 | 44.4 | 39.5; 49.9 | 78.2 |
| FHA | 180 | 168; 194 | 92.1 | 242 | 218; 268 | 89.4 |
| PRN | 200 | 177; 225 | 94.7 | 265 | 231; 304 | 96.6 |
| FIM | 339 | 285; 403 | 92.2 | 499 | 414; 601 | 95.4 |

The following were observed with respect to safety: occurrence, nature, duration, intensity, and relationship to vaccination of any unsolicited systemic adverse events (AEs) reported in the 30 minutes after vaccination; occurrence, time to onset, number of days of occurrence, intensity, action taken, and whether the reaction led to early termination from the study, of solicited injection site reactions occurring up to 7 days after D0 vaccination(s); occurrence, time to onset, number of days of occurrence, intensity, action taken, and whether the reaction led to early termination from the study, of solicited systemic reactions occurring up to 7 days after D0 vaccination(s); occurrence, nature, time to onset, duration, intensity, action taken, relationship to vaccination (for systemic AEs only), and whether the event led to early termination from the study, of unsolicited AEs up to 23-37 days after D0 vaccination(s); and occurrence, nature, time to onset, duration, seriousness criteria, relationship to vaccination, outcome, and whether the serious adverse event (SAE) led to early termination from the study, of SAEs throughout the trial up to 180 days (Group 1 and Group 2) or 210 days (Group 3 and Group 4) after D0 vaccination(s). Solicited systemic reactions included fever, myalgia, and headache. Solicited injection site reactions included pain, erythema, and swelling.

The percentages of subjects reporting at least 1 solicited reaction between D0 and D07 were comparable between MenACYW-TT conjugate vaccine and MENVEO®: 63.5% (315/496) of subjects in Group 1 and 64.2% (316/492) in Group 2, respectively. The percentages of subjects reporting at least 1 solicited reaction were comparable between subjects who received MenACYW-TT conjugate vaccine concomitantly with Tdap and HPV versus Tdap and HPV alone: 88.9% (345/388) in Group 3 and 89.0% (258/290) in Group 4, respectively. The percentages of subjects who reported at least 1 solicited injection site reaction were comparable between Group 1, Group 2, and Group 3: 46.6% (231/496), 45.7% (225/492), and 49.0% (190/388), respectively. No increase in local reactogenicity for the MenACYW-TT conjugate vaccine was seen when MenACYW-TT conjugate vaccine was given concomitantly with Tdap and HPV (Group 3) versus when MenACYW-TT conjugate vaccine was given alone (Group 1).

The most frequently reported solicited injection site reaction was pain, reported by 45.2% (224/496) of subjects in Group 1, 42.5% (209/492) of subjects in Group 2, and 47.2% (183/388) of subjects in Group 3, followed by injection site erythema which was reported by 5.0% (25/496) of subjects in Group 1, 7.5% (37/491) of subjects in Group 2, and 3.9% (15/388) of subjects in Group 3, and injection site swelling which was reported by 5.4% (27/496) of subjects in Group 1, 6.5% (32/491) of subjects in Group 2, and 4.4% (17/388) of subjects in Group 3. The majority of reactions at the MenACYW-TT conjugate vaccine or MENVEO® injection sites were of Grade 1 or 2 intensity, started between D0 and D03, and lasted 1 to 3 days. The percentages of subjects with any Grade 3 injection site reaction at the MenACYW-TT conjugate vaccine or MENVEO® injection site were 1.8% (9/496) in Group 1, 2.2% (11/492) in Group 2, and 2.8% (11/388) in Group 3. The percentages of subjects with Grade 3 pain at the MenACYW-TT conjugate vaccine or MENVEO® injection site were 1.4% (7/496) in Group 1, 1.0% (5/492) in Group 2, and 2.3% (9/388) in Group 3. The percentages of subjects with Grade 3 erythema were 0.4% (2/496) in Group 1, 1.2% (6/491) in Group 2, and 0.5% (2/388) in Group 3. The percentages of subjects with Grade 3 swelling were 0.2% (1/496) in Group 1, 0.4% (2/491) in Group 2, and 0.3% (1/388) in Group 3. Intensity grades generally have the following meanings. Grade 1: No interference with activity. Grade 2: Some interference with activity. Grade 3: Significant; prevents daily activity.

The percentages of subjects reporting at least 1 solicited systemic reaction after vaccination were comparable between Group 1 (52.0% [258/496]) and Group 2 (51.0% [251/492]). Myalgia was the most commonly reported solicited systemic reaction followed by headache and malaise with very few reports of fever. Myalgia was reported in 35.3% (175/496) of subjects in Group 1 and 35.2% (173/492) of subjects in Group 2. Headache was reported in 30.2% (150/496) of subjects in Group 1 and 30.9% (152/492) of subjects in Group 2. Malaise was reported in 26.0% (129/496) of subjects in Group 1 and 26.4% (130/492) of subjects in Group 2. Fever was reported in 1.4% (7/494) of subjects in Group 1 and 1.2% (6/488) of subjects in Group 2.

The percentages of subjects with at least 1 solicited systemic reaction after vaccination were comparable between Group 3 (70.6% [274/388]) and Group 4 (65.9% [191/290]). Myalgia was the most commonly reported solicited systemic reaction: 61.3% (238/388) of subjects in Group 3 and 55.4% (160/289) of subjects in Group 4. Headache was reported in 33.8% (131/388) of subjects in Group 3, and 29.0% (84/290) of subjects in Group 4. Malaise was reported in 29.1% (113/388) of subjects in Group 3, and 27.9% (81/290) of subjects in Group 4. Fever was reported in 1.6% (6/387) of subjects in Group 3, and 0.7% (2/286) of subjects in Group 4. Overall, most solicited systemic reactions were of Grade 1 or Grade 2 intensity, started between D0 and D03, and lasted 1 to 3 days.

Overall, the percentages of subjects who reported Grade 3 solicited systemic reactions were comparable between Group 1 (3.8% [19/496]) and Group 2 (4.3% [21/492]). The percentages of subjects who reported Grade 3 solicited systemic reactions were comparable between Group 3 (7.5% [29/388]) and Group 4 (5.5% [16/290]). The most frequently reported Grade 3 solicited systemic reaction was myalgia followed by malaise and headache. The percentages of subjects who reported Grade 3 myalgia were comparable between Group 1 (1.6% [8/496]) and Group 2 (1.8% [9/492]) and between Group 3 (4.6% [18/388]) and Group 4 (3.8% [11/289]). The percentages of subjects who reported Grade 3 malaise were comparable between Group 1 (2.2% [111/496]) and Group 2 (2.8% [14/492]). Malaise was reported more frequently in Group 3 (2.6% [10/388]) than in Group 4 (1.7% [5/290]). The percentages of subjects who reported Grade 3 headache were the same for both Group 1 (1.8% [9/496]) and Group 2 (1.8% [9/492]). Headache was reported more frequently in Group 3 (2.8% [11/388]) than in Group 4 (1.7% [5/290]).

Overall, the percentages of subjects reporting at least 1 unsolicited AE between D0 and D30 were comparable across the 4 study groups: 22.9% (115/503) of subjects in Group 1 and 25.7% (129/501) in Group 2; 26.0% (102/392) in Group 3 and 22.6% (67/296) in Group 4. Few subjects reported immediate unsolicited AEs: 0.6% (3/503) of subjects in Group 1, 0.2% (1/501) of subjects in Group 2, 0.8% (3/392) of subjects in Group 3, and 0.7% (2/296) of subjects in Group 4. There were no immediate SAEs, including any anaphylactic or life-threatening events. Twelve immediate unsolicited AEs were reported in 9 subjects at 23-37 days. One subject reported 1 immediate unsolicited AE at six months after D0 vaccination(s).

The percentages of subjects who reported at least 1 unsolicited non-serious injection site AR after D0 vaccination(s) were comparable between Group 1 and Group 2: 1.4% (7/503) and 1.6% (8/501), respectively; there was a numerically higher percentage of subjects who reported at least 1 unsolicited non-serious injection site AR in Group 3 than in Group 4: 4.3% (17/392) and 2.0% (6/296), respectively. The most commonly reported unsolicited injection site reaction was pruritus, reported in 14 subjects, followed by bruising, reported in 13 subjects. These unsolicited injection site reactions may occur after any vaccination in general.

The percentages of subjects who reported at least 1 unsolicited non-serious injection site AR at the MenACYW-TT conjugate vaccine or MENVEO® injection sites were comparable: 1.4% (7/503) in Group 1, 1.6% (8/501) in Group 2, and 1.8% (7/392) in Group 3. One subject in Group 2 reported 1 Grade 3 unsolicited non-serious injection site AR of injection site warmth which started on D01, lasted 4 days, and resolved spontaneously. No action was taken. No Grade 3 unsolicited non-serious injection site ARs were reported in Group 1 or at the MenACYW-TT conjugate vaccine injection site in Group 3.

The percentages of subjects reporting at least 1 unsolicited non-serious AE within 30 days were comparable across the 4 study groups: 22.7% (114/503) of subjects in Group 1, 25.5% (128/501) of subjects in Group 2, 26.0% (102/392) of subjects in Group 3, and 22.3% (66/296) of subjects in Group 4. Most frequently reported were infections and infestations (7.2% [36/503] of subjects in Group 1, 8.0% [40/501] of subjects in Group 2, 8.2% [32/392] of subjects in Group 3, 6.1% [18/296] of subjects in Group 4); the most common type was upper respiratory tract infection.

Sixteen subjects reported SAEs during the trial period; 4 subjects reported SAEs within 30 days of vaccination on D0. None were considered as related to the vaccine, and none led to discontinuation from the study. All subjects recovered. No deaths were reported during the study period.

Vaccination with MenACYW-TT conjugate vaccine among adolescents was found to be safe, with no safety concerns identified when given alone or concomitantly with Tdap and HPV vaccines. The safety profile of MenACYW-TT conjugate vaccine was comparable to that of the licensed MENVEO® vaccine.

f) Phase III Clinical Trial 1—Immunogenicity and Safety of a Booster Dose of MenACYW-TT in Adolescents and Adults This study evaluated safety and immunogenicity of a single dose (10 µg polysaccharide per serogroup, conjugated to 65 µg TT total, in 0.67% NaCl/30 mM sodium acetate buffered at pH 6.0) of MenACYW-TT administered intramuscularly to adolescents (≥15 to <18 years) and adults (18-59 years). Subjects had been given one dose of a quadrivalent meningococcal conjugate vaccine ("priming vaccine") 4-10 years before administration of MenACYW-TT (group 1; n=402).

Menactra® (Meningococcal (Groups A, C, Y and W-135) Capsular Saccharide Diphtheria Toxoid Conjugate Vaccine, referred to herein as "MenACYW-DT", a licensed quadrivalent meningococcal conjugate vaccine, was administered to a control group (group 2; n=407). Subjects in group 2 had also been given one dose of a priming vaccine 4-10 years earlier.

In both groups, the priming vaccine was MenACYW-DT (86.3% of all subjects), MenACYW-CRM$_{197}$ (11.25% of all subjects; MenACYW-CRM$_{197}$ is discussed above with respect to clinical trial 4), or unknown (2.45% of all subjects; 9 in group 1 and 10 in group 2). Study group demographics were as in Table 17.

hSBA and baby rabbit serum bactericidal (rSBA) assays were performed at 30 days after treatment. hSBA assays were also performed at day 6. The percentage of subjects that showed a positive seroresponse is given in Table 18. For the hSBA results, a positive seroresponse was either a post-vaccination titer ≥1:16 when the baseline titer was <1:8, or a four-fold increase post-vaccination when the baseline titer was ≥1:8. 384 group 1 subjects and 389 group 2 subjects had valid hSBA results at day 30. For the rSBA results, a positive seroresponse was either a post-vaccination titer ≥1:32 when the baseline titer was <1:8, or a four-fold increase post-vaccination when the baseline titer was ≥1:8.

TABLE 18 hSBA and rSBA Results at for Clinical Trial 5

| Serogroup | Group 1 (MenACYW-TT) | | Group 2 (MenACYW-DT) | |
| --- | --- | --- | --- | --- |
| | % subjects | 95% CI | % subjects | 95% CI |
| hSBA, day 30 | | | | |
| A | 92.2 | (89.0; 94.7) | 87.1 | (83.4; 90.3) |
| C | 97.1 | (94.9; 98.6) | 91.8 | (88.6; 94.3) |
| Y | 97.4 | (95.3; 98.7) | 95.6 | (93.1; 97.4) |
| W | 98.2 | (96.3; 99.3) | 90.7 | (87.4; 93.4) |
| hSBA, day 6 | | | | |
| A | 72.7 | (59.0; 83.9) | 66.1 | (53.0; 77.7) |
| C | 83.6 | (71.2; 92.2) | 87.1 | (76.1; 94.3) |
| Y | 90.9 | (80.0; 97.0) | 83.9 | (72.3; 92.0) |
| W | 94.5 | (84.9; 98.9) | 83.9 | (72.3; 92.0) |
| rSBA, day 30 | | | | |
| A | 80.2 | (70.6; 87.8) | 71 | (61.1; 79.6) |
| C | 98.9 | (94.0; 100.0) | 96 | (90.1; 98.9) |
| Y | 95.6 | (89.1; 98.8) | 87 | (78.8; 92.9) |
| W | 94.5 | (87.6; 98.2) | 95 | (88.7; 98.4) |

The percentage of subjects that showed an SBA titer≥1:8 at day 30 was ≥99% for all serogroups and did not vary significantly with the identity of the previously administered vaccine (data not shown).

Table 19 shows Geometric Mean Titers (GMT) at day 0 (pre-treatment) and day 30 as measured by SBA and rSBA. For day 30, SBA results are presented for the groups as a whole and the subgroups that had been previously given MenACYW-DT and MenACYW-CRM$_{197}$.

TABLE 17

Study groups for Phase III Clinical Trial 1

| Group | n | Treatment | Males | Females | Mean, Median age (yrs) | Priming vaccine MenACYW-DT | Priming vaccine MenACYW-CRM$_{197}$ |
| --- | --- | --- | --- | --- | --- | --- | --- |
| 1 | 402 | MenACYW-TT | 195 | 207 | 22.0, 16.5 | 327 | 48 |
| 2 | 407 | MenACYW-DT | 207 | 200 | 22.5, 16.4 | 340 | 39 |

TABLE 19

Geometric Mean Titers hSBA

| Serogroup | | Group 1 (all) GMT | 95% CI | Group 2 (all) GMT | 95% CI | Group 1/Group 2 GMT Ratio | |
|---|---|---|---|---|---|---|---|
| A | D0 | 13.7 | (12.2; 15.5) | 15.1 | (13.5; 16.9) | | |
|   | D30 | 497 | (436; 568) | 296 | (256; 343) | 1.68 | (1.38; 2.05) |
| C | D0 | 11.0 | (9.32; 13.1) | 10.6 | (9.10; 12.4) | | |
|   | D30 | 2618 | (2227; 3078) | 599 | (504; 71) | 4.37 | (3.45; 5.53) |
| Y | D0 | 7.7 | (6.56; 9.04) | 7.27 | (6.21; 8.50) | | |
|   | D30 | 2070 | (1807; 2371) | 811 | (699; 941) | 2.55 | (2.09; 3.12) |
| W | D0 | 9.76 | (8.46; 11.2) | 10.6 | (9.21; 12.2) | | |
|   | D30 | 1747 | (1508; 2025) | 723 | (614; 853) | 2.42 | (1.94; 3.01) | hSBA

| Serogroup | | Group 1 (previously given MenACYW-DT) GMT | 95% CI | Group 2 (previously given MenACYW-DT) GMT | 95% CI | Group 1/Group 2 GMT Ratio | |
|---|---|---|---|---|---|---|---|
| A | D30 | 490 | (424; 565) | 298 | (255; 349) | 1.64 | (1.33; 2.03) |
| C | D30 | 2505 | (2096; 2993) | 575 | (478; 691) | 4.36 | (3.37; 5.63) |
| Y | D30 | 2009 | (1737; 2324) | 771 | (660; 902) | 2.61 | (2.10; 3.23) |
| W | D30 | 1758 | (1497; 2065) | 671 | (563; 800) | 2.62 | (2.06; 3.32) | hSBA

| Serogroup | | Group 1 (previously given MenACYW-$CRM_{197}$) GMT | 95% CI | Group 2 (previously given MenACYW-$CRM_{197}$) GMT | 95% CI | Group 1/Group 2 GMT Ratio | |
|---|---|---|---|---|---|---|---|
| A | D30 | 636 | (439; 920) | 238 | (148; 384) | 2.67 | (1.49; 4.79) |
| C | D30 | 4096 | (2745; 6113) | 771 | (439; 1351) | 5.31 | (2.74; 10.3) |
| Y | D30 | 2981 | (2011; 4420) | 1245 | (738; 2101) | 2.39 | (1.27; 4.51) |
| W | D30 | 1773 | (1185; 2651) | 1202 | (697; 2071) | 1.48 | (0.768; 2.83) | rSBA

| Serogroup | | Group 1 GMT | 95% CI | Group 2 GMT | 95% CI |
|---|---|---|---|---|---|
| A | D0 | 1097 | (724:1662) | 1144 | (812; 1613) |
|   | D30 | 10859 | (8844; 13333) | 6608 | (5410; 8071) |
| C | D0 | 15.2 | (9.38; 24.5) | 9.1 | (5.90; 14.1) |
|   | D30 | 11898 | (9425; 15021) | 2665 | (1934; 3672) |
| Y | D0 | 84.2 | (45.7; 155) | 52.7 | (29.0; 95.9) |
|   | D30 | 9468 | (7447; 12037) | 3848 | (2778; 5331) |
| W | D0 | 141 | (74.3; 269) | 145 | (85.0; 247) |
|   | D30 | 21227 | (17199; 26200) | 9410 | (7203; 12294) |

The results presented above show that the percentage of subjects who demonstrated seroresponse following administration of MenACYW-TT was greater than MenACYW-DT for all 4 serogroups at day 30 post-booster using the hSBA assay. Post-vaccination GMTs according to hSBA were also numerically higher for MenACYW-TT vaccine versus MenACYW-DT for all 4 serogroups.

Furthermore, administration of a single dose of MenACYW-TT in adults and adolescents that had received a single dose of a MenACYW-DT or MenACYW-$CRM_{197}$ 4-10 years ago), was well tolerated and did not generate any new safety concerns or safety signals. The following were observed with respect to safety: occurrence, nature, duration, intensity, and relationship to vaccination of any unsolicited systemic AEs reported in the 30 minutes after vaccination; occurrence, time to onset, number of days of occurrence, intensity, action taken, and whether the reaction led to early termination from the study, of solicited injection site reactions occurring up to 7 days after vaccination; occurrence, time to onset, number of days of occurrence, intensity, action taken, and whether the reaction led to early termination from the study, of solicited systemic reactions occurring up to 7 days after vaccination; occurrence, nature, time to onset, duration, intensity, action taken, relationship to vaccination (for systemic AEs only), and whether the event led to early termination from the study, of unsolicited AEs occurring up to D30 (+14 days); and occurrence, nature, time to onset, duration, seriousness criteria, relationship to vaccination, outcome, and whether the SAE led to early termination from the study, of SAEs throughout the trial. Solicited AEs were essentially as described above for Phase II Clinical Trial 4.

Overall, the percentages of subjects reporting at least 1 solicited reaction were comparable between Group 1 and Group 2: 64.3% (256/398) of subjects in Group 1 and 65.4% (263/402) of subjects in Group 2, respectively. The percentages of subjects reporting at least 1 Grade 3 solicited reaction were comparable between Group 1 and Group 2: 5.0% (20/398) of subjects in Group 1 and 5.5% (22/402) of subjects in Group 2, respectively. The percentages of subjects reporting at least 1 solicited injection site reaction were comparable between Group 1 and Group 2: 46.5% (185/398) of subjects in Group 1 and 49.3% (198/402) of subjects in Group 2, respectively. The most frequently reported solicited injection site reaction was pain reported by 44.7% (178/398) of subjects in Group 1 and 48.8% (196/402) of subjects in Group 2. Erythema and swelling were reported less frequently. Erythema and swelling were reported at a higher frequency in Group 1 (5.0% [20/398] and 4.0% [16/398], respectively) than in Group 2 (1.5% [6/402] and 0.7% [3/402], respectively). Most were of Grade 1 intensity; the percentages of subjects that reported Grade 2 erythema and swelling were comparable between Group 1 (0.5% [2/398] and 0.8% [3/398], respectively) and Group 2 (0.2% [1/402] and 0.5% [2/402], respectively). No Grade 3 erythema or swelling was reported in either group. The majority of reactions at the MenACYW conjugate vaccine or Menactra® injection sites were of Grade 1 or 2 intensity, most started between D0 and D03, and most lasted 1 to 3 days. Few subjects reported Grade 3 solicited injection site reactions: 1.0% (4/398) of subjects in Group 1 and 2.0% (8/402) of subjects in Group 2 reported Grade 3 pain. No subjects in either group reported Grade 3 erythema or swelling.

The percentages of subjects who reported at least 1 solicited systemic reaction were comparable between Group 1 and Group 2: 55.3% (220/398) of subjects in Group 1 and 54.2% (218/402) of subjects in Group 2, respectively. Myalgia and headache were the most frequently reported solicited systemic reactions: myalgia was reported by 36.7% (146/398) of subjects in Group 1 and by 38.8% (156/402) of subjects in Group 2; headache was reported by 37.9% (151/398) of subjects in Group 1 and 33.3% (134/402) of subjects in Group 2. Malaise was reported by 27.6% (110/398) of subjects in Group 1 and by 26.9% (108/402) of subjects in Group 2. Fever was not reported in Group 1 (0.0% [0/390]) and was reported in 0.5% (2/395) of subjects in Group 2. Overall, most solicited systemic reactions were of Grade 1 or Grade 2 intensity, started between D0 and D30, and lasted 1 to 3 days. Few subjects reported Grade 3 solicited systemic reactions. The percentages of subjects reporting a Grade 3 solicited systemic reaction were similar between Group 1 and Group 2 for fever (0.0% [0/390] and 0.3% [1/395], respectively), headache (2.3% [9/398] and 3.5% [14/402], respectively), malaise (2.8% [11/398] and 3.5% [14/402], respectively), and myalgia (2.0% [8/398] and 2.2% [9/402], respectively).

The percentages of subjects reporting at least 1 unsolicited non-serious AE between D0 and D30 were comparable between Group 1 (26.1% [105/402]) and Group 2 (25.3% [103/407]). The number of unsolicited non-serious AEs was the same in Group 1 (n=164 AEs) and in Group 2 (n=164 AEs). A small and comparable percentage of unsolicited non-serious AEs were considered related to the vaccine given on D0: 3.0% (12/402) of subjects in Group 1 and 2.9% (12/407) of subjects in Group 2. Most of these events were of Grade 1 or Grade 2 intensity.

Two subjects (0.5%) in Group 1 and no subjects (0.0%) in Group 2 reported at least 1 immediate unsolicited AE (dizziness in both subjects).

A total of 5 subjects (1.2%) in Group 1 and 6 subjects (1.5%) in Group 2 reported at least 1 unsolicited non-serious injection site AR. Injection site bruising was reported in 2 subjects (0.5%) in Group 1 and in 3 subjects (0.7%) in Group 2. Injection site pruritus was reported in 2 subjects (0.5%) in Group 1 and 1 subject (0.2%) in Group 2. Injection site warmth was reported in 1 subject (0.2%) in Group 1. Injection site discoloration and injection site urticaria were reported in 1 subject each (0.2%) in Group 2. Injection site discoloration was Grade 3 and was ongoing at the end of the study.

Infections and infestations were the most frequently reported unsolicited non-serious systemic AEs (7.5% [30/402] of subjects in Group 1 and 6.6% [27/407] of subjects in Group 2). Frequently reported type of infections or infestations were nasopharyngitis, reported by 1.7% (7/402) of subjects in Group 1 and 1.7% (7/407) of subjects in Group 2; and upper respiratory tract infection, reported by 1.0% (4/402) of subjects in Group 1 and 1.7% (7/407) of subjects in Group 2. Also frequently reported were reported in the SOC of respiratory, thoracic and mediastinal disorders: 6.0% (24/402) of subjects in Group 1 and 6.6% (27/407) of subjects in Group 2, including cough and oropharyngeal pain. Most unsolicited non-serious AEs within 30 days of vaccine injection were of Grade 1 or Grade 2 intensity. The percentages of subjects who reported at least 1 Grade 3 unsolicited non-serious systemic AE were comparable between both groups: 3.7% (15/402) of subjects in Group 1 and 4.2% (17/407) of subjects in Group 2.

Unsolicited non-serious systemic ARs were most frequently reported in the classification of General disorders and administration site conditions, reported by 2.2% (9/402) of subjects in Group 1 and 1.7% (7/407) of subjects in Group 2. The most frequently reported unsolicited non-serious systemic AR in this classification was fatigue, reported by 0.5% (2/402) of subjects in Group 1 and 0.2% (1/407) of subjects in Group 2. Only 1 subject in Group 2 reported 2 Grade 3 unsolicited non-serious systemic ARs: Grade 3 nausea in the SOC of Gastrointestinal disorders and Grade 3 fatigue in the classification of General disorders and administration site conditions. Both started on D0 and lasted for 2 days. Medication was taken for the nausea; no action was taken for the fatigue.

There were no AEs or ARs that led to discontinuation from the study in either group. Three subjects experienced SAEs within the first 30 days after vaccination: bilateral pulmonary embolism in 1 subject in Group 1 and major depressive disorder and chest pain in 1 subject each in Group 2. None of these SAEs were considered as related to the vaccine by the Investigator and none led to discontinuation from the study.

Six subjects (4 in Group 1 and 2 in Group 2) experienced a total of 6 SAEs after D30 through the 6-month followup: 4 subjects (1.0%) in Group 1 experienced 4 SAEs and 2 subjects (0.5%) in Group 2 experienced 2 SAEs. None of the SAEs were considered as related to the vaccine and none led to discontinuation from the study. No deaths were reported during the study.

Vaccination with a booster dose of MenACYW conjugate vaccine in quadrivalent meningococcal conjugate vaccine-primed adolescents and adults aged at least 15 years was found to be safe, with no safety concerns identified. Overall, the safety profile of MenACYW conjugate vaccine was comparable to that of the licensed vaccine, Menactra®.

7. MenACYW-TT Liquid Formulation Stability

Some or all components of existing meningococcal polysaccharide conjugate vaccines such as MenACWY-CRM$_{197}$/

Menveo® (a quadrivalent conjugate to CRM197, in which the MenA conjugate is lyophilized) and MCV4-TT/Nimenrix® (an entirely lyophilized quadrivalent conjugate to T) are not stored long-term as liquid formulations. Menactra® (a quadrivalent conjugate to TI) is stored as a liquid formulation but its shelf-life is 24 months. In a recent publication, Beresford et al. characterized the stability of various existing vaccines and observed depolymerization and loss of immunogenicity under certain conditions, leading them to recommend that for "any newly developing MenACWY saccharide-protein conjugate vaccines, a key recommendation would be to consider the lyophilization of final product to prevent deleterious degradation that would affect immunogenicity." Beresford et al., Vaccine 2017 Jun. 16; 35(28): 3598-3606 at Abstract.

Liquid formulations are advantageous at least because they do not require a lyophilization step during manufacturing, do not require a reconstitution step before administration, and avoid the risk of possible errors associated with reconstitution. Of course, these advantages are irrelevant if the product itself undergoes degradation that compromises immunogenicity. Accordingly, it would be desirable for a MenACYW conjugate vaccine to be stable as a liquid formulation for more than 24 months. The stability of MenACYW-TT according to the present disclosure was characterized as follows.

MenACYW-TT was stored in 0.67% NaCl/30 mM sodium acetate buffered at pH 6.0 for 54 months at 2° C.-8° C. and tested for stability at time points selected from 0, 1, 3, 6, 9, 12, 18, 24, 30, 36, 42, 48, and 54 months (see Table 20). Parameters measured included visual appearance, sterility, absence of abnormal toxicity, total polysaccharide of each serogroup, % free polysaccharide, molecular weight, polydispersity, pH, and immunogenicity.

Accelerated stability testing of MenACYW-TT was also performed by storing the formulation at 23° C.-27° C. Tests were performed at one or more of 1 week, 3 months, and 6 months (see Table 21).

Regarding visual appearance, the solution remained clear for the entire periods of 54 months at 2° C.-8° C. and 6 months at 23° C.-27° C. and no defects were noted (all time points listed above were tested).

Absence of abnormal toxicity was determined by observing rodents (mice or guinea pigs) following administration of a dose of MenACYW-TT. In all tests, all animals survived the test period of 28 days following administration; there were no non-specific or unexpected responses; and the animals did not lose weight during the test period. Abnormal toxicity testing was performed at the 0, 12, 24, 36, 42, 48, and 54-month time points.

The pH was 6.1 at 0 months and all measurements were in the range of 6.1 to 6.3 throughout the time courses (time points for pH were 0, 1, 6, 12, 24, 36, 42, 48, and 54 months at 2° C.-8° C. and 6 months at 23° C.-27° C.). No growth was observed at any of the tested time points including 54 months (time points for sterility were 0, 12, 24, 36, 42, 48, and 54 months at 2° C.-8° C. and 6 months at 23° C.-27° C.).

Total polysaccharide was measured by Dionex™ chromatography. The % free polysaccharide was measured by Dionex™ chromatography and deoxycholate precipitation. Molecular weight and polydispersity were measured by size exclusion chromatography/multi-angle light scattering (SEC/MALS).

Results for 2° C.-8° C. are in Table 20 and results for 23° C.-27° C. are in Table 21.

TABLE 20

Stability Test Results for Storage at 2° C. to 8° C.

| Test | Serogroup | Time 0 | 1 Month | 3 Months | 6 Months | 9 Months | 12 Months | 18 Months |
|---|---|---|---|---|---|---|---|---|
| Total | A | 20.2 | 19.3 | 16.6 | 18.2 | 18.8 | 21.3 | 21.9 |
| Polysaccharide | C | 19.4 | 20.8 | 15.0 | 14.5 | 16.2 | 18.3 | 20.4 |
| (µg/mL) | Y | 16.7 | 16.2 | 20.7 | 16.8 | 16.9 | 17.2 | 16.4 |
|  | W-135 | 15.9 | 15.6 | 12.4 | 15.9 | 15.5 | 16.3 | 17.5 |
| % Free | A | <15% | <16% | <18% | <17% | <16% | <14% | <14% |
| Polysaccharide | C | <16% | <14% | <20% | <21% | <19% | <16% | <15% |
|  | Y | <18% | 19% | <15% | <18% | <18% | 18% | <18% |
|  | W-135 | <19% | <19% | <24% | <19% | <19% | <18% | <17% |
| Molecular Weight | All | 9.122E5 | 5.095E5 | 7.679E5 | 7.713E5 | 1.533E6 | 8.348E5 | 9.958E5 |
| Polydispersity | All | 1.381 | 1.359 | 1.298 | 1.311 | 1.862 | 1.256 | 1.581 |

| Test | Serogroup | Time 0 | 24 Months | 30 Months | 36 Months | 42 Months | 48 Months | 54 Months |
|---|---|---|---|---|---|---|---|---|
| Total | A | 20.2 | 19.4 | 19.4 | 18.4 | 19.2 | 18.6 | 18.8 |
| Polysaccharide | C | 19.4 | 17.7 | 18.2 | 18.2 | 22.4 | 21.6 | 20.0 |
| (µg/mL) | Y | 16.7 | 13.5 | 14.6 | 14.7 | 18.5 | 14.8 | 14.2 |
|  | W-135 | 15.9 | 14.6 | 13.3 | 13.5 | 15.3 | 15.5 | 14.5 |
| % Free | A | <15% | <15% | <15% | <16% | <16% | 17 | 17 |
| Polysaccharide | C | <16% | <17% | <16% | <16% | <13% | <14 | <15 |
|  | Y | <18% | <22% | <20% | <20% | 21% | <20 | <21 |
|  | W-135 | <19% | <21% | <23% | <22% | <20% | <19 | <21 |
| Molecular Weight | All | 9.122E5 | 9.958E5 | 1.192E6 | 5.419E5 | 8.286E5 | 7.700E5 | 8.092E5 |
| Polydispersity | All | 1.381 | 1.581 | 1.432 | 1.288 | 1.485 | 1.572 | 1.495 |

NS: not scheduled.

†: Sera samples were held at <−20° C. for about 6-7 months, where they were considered stable, before testing.

TABLE 21

Stability Test Results for Storage at 23° C. to 27° C.

| Test | Serogroup | 1 Week | 3 Months | 6 Months |
|---|---|---|---|---|
| Total Polysaccharide (μg/mL) | A | 19.4 | 22.0 | 22.0 |
| | C | 14.1 | 20.5 | 19.9 |
| | Y | 13.9 | 17.0 | 15.9 |
| | W-135 | 15.5 | 17.3 | 16.2 |
| % Free Polysaccharide | A | <15% | 27% | 31% |
| | C | <21% | 25% | 18% |
| | Y | <22% | <18% | 30% |
| | W-135 | <19% | 17% | 28% |
| Molecular Weight | All | 8.212E5 | 8.285E5 | 6.209E5 |
| Polydispersity | All | 1.335 | 1.361 | 1.474 |

NS: not scheduled.

The results indicated good stability over the entire periods of 54 months at 2° C.-8° C. and 6 months at 23° C.-27° C. In particular, at 2° C.-8° C., for all four serogroups there was minimal loss of conjugation of polysaccharide to TT (0-3% increase in % free polysaccharide) and immunogenicity was substantially maintained at all time points except for 24 months, in which the low values appear to be outliers and/or to have resulted from a technical issue based on the observations at 36 months and later, which are more similar to the 0 and 12 month measurements. At 23° C.-27° C., there was an increase in free polysaccharide for MenA, MenY, and MenW by six months, but the levels remained below the acceptable limit of 40%. Immunogenicity was still present at six months.

From these results, one can conclude that MenACYW-TT can be maintained long-term as a liquid formulation under refrigeration, e.g., during packaging, distribution, and storage, and that lyophilization or other measures for preservation are unnecessary.

Although the foregoing invention has been described in some detail by way of illustration and example for purposes of clarity of understanding, the descriptions and examples should not be construed as limiting the scope of the invention.

What is claimed is:

1. A method of vaccinating a subject against *Neisseria meningitidis* comprising administering a dose of a *Neisseria meningitidis* vaccine composition to the subject, wherein the *Neisseria meningitidis* vaccine composition comprises:
    a) a first conjugate of MenA capsular polysaccharide to a carrier protein;
    b) a second conjugate of MenC capsular polysaccharide to a carrier protein;
    c) a third conjugate of MenW-135 capsular polysaccharide to a carrier protein; and
    d) a fourth conjugate of MenY capsular polysaccharide to a carrier protein;
    wherein:
        (i) the second conjugate is a population comprising double-end-linked conjugated polysaccharides and single-end-linked conjugated polysaccharides, wherein the polysaccharides of the second conjugate have an O-acetylation level of 0.3 μmol/mg polysaccharide to 1.6 μmol/mg polysaccharide;
        (ii) the MenA capsular polysaccharide is attached to the carrier protein through a linker comprising a carbamate, a spacer, and an amide, wherein the spacer is between the carbamate and the amide and comprises 2-10 linear carbons, and the first conjugate has a polysaccharide to carrier protein mass ratio of 0.3 to 1.5;
        (iii) the MenC, MenW-135, and MenY capsular polysaccharides are directly attached to the carrier protein through a secondary amine and at least one of the conjugates has a weight average molecular weight ranging from 300 kDa to 1500 kDa;
        (iv) the carrier protein is tetanus toxoid; and
    the composition comprises less than 20% free polysaccharide by weight relative to total polysaccharide.

2. A method of vaccinating a subject against *Neisseria meningitidis* comprising administering a dose of a *Neisseria meningitidis* vaccine composition to the subject, wherein the *Neisseria meningitidis* vaccine composition comprises a conjugate of MenC capsular polysaccharide to a carrier protein, wherein the conjugate is a population comprising double-end-linked conjugated polysaccharides and single-end-linked conjugated polysaccharides which are both directly attached to the carrier protein through a secondary amine, and the polysaccharides of the conjugate of MenC capsular polysaccharide to the carrier protein have an O-acetylation level ranging from 0.3 μmol/mg polysaccharide to 1.6 μmol/mg polysaccharide.

3. The method of claim 2, wherein the carrier protein is tetanus toxoid.

4. The method of claim 2, wherein the *Neisseria meningitidis* vaccine composition comprises:
    a) a first conjugate of MenA capsular polysaccharide to a carrier protein;
    b) the conjugate of MenC capsular polysaccharide to the carrier protein;
    c) a third conjugate of MenW-135 capsular polysaccharide to a carrier protein; and
    d) a fourth conjugate of MenY capsular polysaccharide to a carrier protein;
    wherein:
        (i) the MenA capsular polysaccharide is attached to the carrier protein through a linker comprising a carbamate, a spacer, and an amide, wherein the spacer is between the carbamate and the amide and comprises 2-10 linear carbons, and the first conjugate has a polysaccharide to carrier protein mass ratio of 0.3 to 1.5;
        (ii) the MenC, MenW-135, and MenY capsular polysaccharides are directly attached to the carrier protein through a secondary amine and at least one of the conjugates has a weight average molecular weight ranging from 300 kDa to 1500 kDa; and
    the composition comprises less than 20% free polysaccharide by weight relative to total polysaccharide.

5. A method of vaccinating a subject against *Neisseria meningitidis* comprising administering a dose of a *Neisseria meningitidis* vaccine composition to the subject, wherein the *Neisseria meningitidis* vaccine composition comprises:
    a) a first conjugate of MenA capsular polysaccharide to tetanus toxoid carrier protein, wherein the MenA capsular polysaccharide is attached to the tetanus toxoid carrier protein through a linker of formula (I):

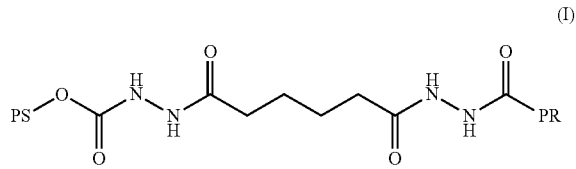

(I)

wherein PS indicates attachment to the polysaccharide and PR indicates attachment to the carrier protein,
and wherein the MenA capsular polysaccharide to tetanus toxoid carrier protein mass ratio is 0.5 to 1.5;
  b) a second conjugate of MenC capsular polysaccharide directly attached to tetanus toxoid carrier protein, wherein the second conjugate is a population comprising double-end-linked conjugated polysaccharides and single-end-linked conjugated polysaccharides, wherein the polysaccharides have an O-acetylation level of 0.3 μmol/mg polysaccharide to 1.6 μmol/mg polysaccharide, wherein the second conjugate has a weight average molecular weight ranging from 300 kDa to 1500 kDa, wherein the MenC polysaccharide is reduced in size by 3×-8× relative to native MenC polysaccharide, and wherein the MenC capsular polysaccharide to tetanus toxoid carrier protein mass ratio is 0.3 to 1.1;
  c) a third conjugate of MenW-135 capsular polysaccharide directly attached to tetanus toxoid carrier protein, wherein the MenW-135 capsular polysaccharide to tetanus toxoid carrier protein mass ratio is 0.3 to 1.3;
  d) a fourth conjugate of MenY capsular polysaccharide directly attached to tetanus toxoid carrier protein, wherein the MenY capsular polysaccharide to tetanus toxoid carrier protein mass ratio is 0.5 to 1.3; and
  the composition comprises less than 20% free polysaccharide by weight relative to total polysaccharide.

6. The method of claim 5, wherein the *Neisseria meningitidis* vaccine composition is administered intramuscularly.

7. The method of claim 5, wherein the subject is age 6 weeks to 3 years.

8. The method of claim 5, wherein the subject is at least 15 years of age.

9. The method of claim 5, wherein the subject is age 50 years or more.

10. The method of claim 5, further comprising administering a vaccine that is not directed to *Neisseria meningitidis* at the same time as, but not in the same injection as, the *Neisseria meningitidis* vaccine composition.

11. The method of claim 10, wherein the vaccine that is not directed to *Neisseria meningitidis* is a vaccine that is directed to preventing varicella, diphtheria, Hib, hepatitis b, measles, mumps, pertussis, polio, pneumococcus, rotavirus, rubella, or tetanus infections.

12. The method of claim 1, wherein the subject previously received a *Neisseria meningitidis* capsular saccharide conjugate vaccine.

13. The method of claim 12, wherein the subject received the *Neisseria meningitidis* capsular saccharide conjugate vaccine four months to ten years earlier.

14. The method of claim 1, wherein the subject did not previously receive a *Neisseria meningitidis* capsular saccharide conjugate vaccine.

15. The method of claim 1, wherein the *Neisseria meningitidis* vaccine composition is administered as a single dose.

16. The method of claim 1, wherein the *Neisseria meningitidis* vaccine composition is administered as a series.

17. The method of claim 16, wherein the *Neisseria meningitidis* vaccine composition is administered two to four months after a previously administered *Neisseria meningitidis* capsular saccharide conjugate vaccine.

18. The method of claim 16, wherein the *Neisseria meningitidis* vaccine composition is administered six to twelve months after a previously administered *Neisseria meningitidis* capsular saccharide conjugate vaccine.

19. The method of claim 16, wherein the *Neisseria meningitidis* vaccine composition is administered 1 year to 2 years after a previously administered *Neisseria meningitidis* capsular saccharide conjugate vaccine.

20. The method of claim 1, wherein the subject is vaccinated up to three times before their first birthday, and once around or after their first birthday.

21. The method of claim 16, wherein the first vaccination is at 7-10 weeks of age.

22. The method of claim 16, wherein the second vaccination is at 4 or 5 months of age.

23. The method of claim 16, wherein the first vaccination is at 6 months and a second vaccination is given up to 24 months.

24. The method of claim 16, wherein the subject is vaccinated at about age 2 months, 4 months, 6 months, and 12-15 months.

25. The method of claim 16, wherein the subject is vaccinated at about age 6 months and 12 months.

* * * * *

UNITED STATES PATENT AND TRADEMARK OFFICE
CERTIFICATE OF CORRECTION

| | | |
|---|---|---|
| PATENT NO. | : 11,707,514 B2 | Page 1 of 1 |
| APPLICATION NO. | : 17/468989 | |
| DATED | : July 25, 2023 | |
| INVENTOR(S) | : Richard David Kensinger et al. | |

It is certified that error appears in the above-identified patent and that said Letters Patent is hereby corrected as shown below:

In the Claims

In Claim 23, Column 64, Lines 36-37, "is at 6 months and a second vaccination is given up to 24 months." should read --is at 6 months of age and a second vaccination is given up to 24 months of age.--

Signed and Sealed this
Twenty-sixth Day of September, 2023

Katherine Kelly Vidal
*Director of the United States Patent and Trademark Office*